US008802365B2

(12) United States Patent
Reddien et al.

(10) Patent No.: US 8,802,365 B2
(45) Date of Patent: Aug. 12, 2014

(54) METHODS FOR IDENTIFYING CANDIDATE MODULATORS OF NOTUM ACTIVITY

(75) Inventors: Peter Reddien, Cambridge, MA (US); Christian Petersen, Evanston, IL (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 13/427,660

(22) Filed: Mar. 22, 2012

(65) Prior Publication Data

US 2012/0269798 A1 Oct. 25, 2012

Related U.S. Application Data

(60) Provisional application No. 61/466,388, filed on Mar. 22, 2011.

(51) Int. Cl.
*C12Q 1/00* (2006.01)
*C12Q 1/66* (2006.01)
*C12N 11/00* (2006.01)

(52) U.S. Cl.
USPC ................................... 435/4; 435/8; 435/174

(58) Field of Classification Search
None
See application file for complete search history.

(56) References Cited

FOREIGN PATENT DOCUMENTS

| WO | WO/03/062410 | | 7/2003 | | |
|----|--------------|---|--------|---|---|
| WO | WO 2012/027723 | * | 3/2012 | ........... | A61K 39/395 |
| WO | WO 2012/071381 | * | 5/2012 | ........... | A61K 39/395 |

OTHER PUBLICATIONS

Giraldez et al 2002. Dev. Cell 2:667-676.*
Reddien, Peter W., Abstract "*Stem Cell and Regeneration Regulatory Genes in Planarians*" National Institutes of Health Grant No. 5R01GM080639-05 (Funding Start Date 2008).
Printout from database NCBI GEO accession No. NP_848588 [Online], date Dec. 17, 2012.
Printout from database NCBI GEO accession No. NP_780472 [Online], date Dec. 17, 2012.
Printout from database NCBI GEO accession No. NM_002081 [Online], date Dec. 17, 2012.
Printout from database NCBI GEO accession No. NP_002072 [Online], date Dec. 17, 2012.
Printout from database NCBI GEO accession No. NM_152742 [Online], date Dec. 17, 2012.
Printout from database NCBI GEO accession No. NP_689955 [Online], date Dec. 17, 2012.
Printout from database NCBI GEO accession No. NM_001164617 [Online], date Dec. 17, 2012.
Printout from database NCBI GEO accession No. NP_001158089 [Online], date Dec. 17, 2012.
Printout from database NCBI GEO accession No. NP_004484 [Online], date Dec. 17, 2012.
Printout from database NCBI GEO accession No. NP_004475 [Online], date Dec. 17, 2012.
Printout from database NCBI GEO accession No. NM_001164618 [Online], date Dec. 17, 2012.
Printout from database NCBI GEO accession No. NP_001158090 [Online], date Dec. 17, 2012.
Printout from database NCBI GEO accession No. NM_001164619 [Online], date Dec. 17, 2012.
Printout from database NCBI GEO accession No. NP_001158091 [Online], date Dec. 17, 2012.
Printout from database NCBI GEO accession No. NM_001448 [Online], date Dec. 17, 2012.
Printout from database NCBI GEO accession No. NP_001439 [Online], date Dec. 17, 2012.
Printout from database NCBI GEO accession No. NM_004466 [Online], date Dec. 17, 2012.
Printout from database NCBI GEO accession No. NP_004457 [Online], date Dec. 17, 2012.
Printout from database NCBI GEO accession No. NM_005708 [Online], date Dec. 17, 2012.
Printout from database NCBI GEO accession No. NP_005699 [Online], date Dec. 17, 2012.
Adell, et al., "Smed-Evi/Wntless is required for β-catenin-dependent and independent processes during planarian regeneration", *Development*, 136: 905-910 (2009).
Ayers, et al., "The Long-Range Activity of Hedgehog is Regulated in the Apical Extracellular Space by the Glypican Dallay and the Hydrolase Notum", *Developmental Cell*, 18: 605-320 (2010).
Capurro, et al., "Glypican-3 Promotes the Growth of Hepatocellular Carcinoma by Stimulating Canonical Wnt Signaling", *Cancer Res*, 65(14): 6245-54 (2005).
Filmus, et al., "Glypicans", *Genome Biology*. 9:224 (2008.
Gerlitz, et al., "Wingful, an extracellular feedback inhibitor of Wingless", *Genes & Development*, 16: 1055-1059 (2002).
Giraldez, et al., "HSPG Modification by the Secreted Enzyme Notum Shapes the Wingless Morphogen Gradient", *Developmental Cell*, 2: 667-676 (2002).
Goessling, et al., "APC mutant zebrafish uncover a changing temporal requirement for wnt signaling in liver development", *Developmental Biology*, 320: 161-174 (2008).
Gurley, et al., "β-Catenin Defines Head Versus Tail Identity During Planarian Regeneration and Homeostasis", *Science*, 319: 323-319 (2008).
Gurley, et al., "Expression of secreted Wnt pathway components reveals unexpected complexity of the planarian amputation response", *Developmental Biology*, 347: 24-39 (2010).
Han, et al., "*Drosophilia* glypicans Dally and Dally-like shape the extracellular Wingless morphogen gradient in the wing disc", *Development*, 132: 667-679 (2004).
Kim, et al., "Bone Regeneration is Regulated by Wnt Signaling", *Journal of Bone and Mineral Research*, 22: 1913-1923 (2007).
Kinoshita, et al., "Biosynthesis. Remodelling and Functions of Mammalian GPI-anchored Proteins: Recent Progress", *J. Biochem*. 144: 287-294 (2008).

(Continued)

*Primary Examiner* — Shulamith H Shafer
(74) *Attorney, Agent, or Firm* — Lisa M. Treannie, Esq.; Morse, Barnes-Brown & Pendleton, P.C.

(57) ABSTRACT

The invention provides compositions and methods of use for identifying modulators of NOTUM, e.g., NOTUM inhibitors. In some aspects, identified compounds are useful for modulating Wnt signaling at sites of tissue damage. The invention further provides methods of promoting regeneration by inhibiting NOTUM.

18 Claims, 15 Drawing Sheets

(56) References Cited

OTHER PUBLICATIONS

Kirkpatrick et al., "Spatial Regulation of Wingless Morphogen Distribution and Signaling by Dally-like Protein", *Developmental Cell*, 7: 513-523 (2004).
Kondoh, et al., "Angiotensin-converting enzyme is a GPI-anchored protein releasing factor crucial for fertilization", *Nature Medicine*, 11(2): 160-166 (2005).
Kreuger, et al., "Opposing Activities of Dally-like Glypican at High and Low Levels of Wingless Morphogen Activity", *Developmental Cell*, 7: 503-512 (2004).
Lin, et al., "Requirement for Wnt and FGF signaling in *Xenopus* tadpole tail egeneration", *Developmental Biology*, 316: 323-335 (2008).
Mann, et al., "Effect of glycosylphosphatidylinositol (GPI)-phospholipase D overexpression on GPI metabolism", *Biochem. J.*, 378, 641-648 (2004).
Minear, et al., "Wnt Proteins Promote Bone Regeneration" *Sci Transl Med* 2, 29ra30 (2010).
Orlean, et al., GPI anchoring of protein in yeast and mammalian cells, or: how we learned to stop worrying and love glycophospholipids, *J. Lipid, Res.*, 48: 993-1011 (2007).
Paulick, et al, "The GPI Anchor", *Biochemistry*, 47, 6991-7000 (2008).
Paulick, et al., "Synthetic Analogues of Glycosylphosphatidylinositol-Anchored Proteins and Their Behavior in Supported Lipid Bilayers", *J. Am. Chem. Soc.*, 129:11543-11550 (2007).
Petersen, et al., "*Smed*-βcatenin-*1* is Required for Anteroposterior Blastema Polarity in Planarian Regeneration", *Science*, 319: 327-330 (2008).
Petersen, et al., "A wound-induced Wnt expression program controls planarian regeneration polarity", *Proceedings of the National Academy of Sciences*, 106(40): 17061-17066 (2009).
Petersen, et al., "Wnt Signaling and the Polarity of the Primary Body Axis", *Cell*, 139: 1056-1068 (2009).
Pierleoni, et al., "PredGPI: a GPI-anchor predictor", *BMC Bioinformatics* 9:392 (2008).
Poss, "Advances in understanding tissue regenerative capacity and mechanisms in animals", *Nature Reviews Genetics*, 11:710-722 (2010).
Reddien, et al., "Fundamentals of Planarian Regeneration", *Annu. Rev. Cell Dev. Biol.*, 20:725-57 (2004).
Rink, et al., "Planarian Hh Signaling Regulates Regeneration Polarity and Links Hh Pathway Evolution to Cilia", *Science*, 326: 1406-1409 (2009).
Sharom, et al., "Glycosylphosphatidylinositol-anchored proteins: structure, function, and cleavage by phosphatidylinositol-specific phospholipase C", *Biochem. Cell. Biol.* 80: 535-549 (2002).
Stoick-Cooper, et al., "Distinct Wnt signaling pathways have opposing roles in appendage regeneration", *Development*, 134: 479-489 (2007).
Stoick-Cooper, et al., "Advances in signaling in vertebrate regeneration as a prelude to regenerative medicine", *Genes and Development*, 21: 1292-1315 (2007).
Torisu, et al., "Human homolog of NOTUM, overexpressed in hepatocellular carcinoma, is regulated transcriptionally by β-catenin/TCF", *Cancer Sci*, 99: 1139-1146 (2008).
Traister, et al., "Mammalian Notum induces the release of glypicans and other GPI-anchored proteins from the cell surface", *Biochemical Journal*, 410: 503-511 (2008).
Udenfreid, et al., "How glycosylphosphatidylinositol anchored membrane proteins are made", *Ann. Rev. Biochem.*, 64: 563-91 (1995).
Yazawa, et al., "Planarian Hedgehog/Patched establishes anterior-posterior polarity by regulating Wnt signaling", *Proceedings of the National Academy of Sciences*, 106 (52): 22320-22334 (2009).
Yokoyama, et al., "Wnt/(β-catenin signaling has an essential role in the initiation of limb regeneration", *Developmental Biology*, 306: 170-178 (2007).
Zitterman, et al., Soluble Glypican 3 inhibits the growth of Hepatocellular Carcinoma in vitro and in vivo. *International Journal of Cancer*, 126: 1291-1301 (2010).
Petersen, et al., "Polarized *notum* Activation at Wounds Inhibits Wnt Function to Promote Planarian Head Regeneration", *Science*, 332(6031): 852-855 (2011).

* cited by examiner

Smed-notum, complete cds

TTATAAATATCGACGATCACATAACTAACCAAAGTTAAATCTAAAATTTCT
GAGGATCGAAAAAATTGAAAACTATTCTTCAAATATTTGGTTTTTATTCCA
GGATCAAAAAATGAAATCATATCTGATATTGAATACTCTTCTATTGAGCCT
ATTGAAGATCAATGGATTTTCCAAATCGTCTTGGTTCAGTTCAAAGACTTC
GTTGATTTTCGATCGAATCAACAAATTGAATGATCCGCAATCCAGTAATTC
AATTCACAGTAGAAATATCAGTATTTTCAGTTGAAAAATTTCCAAATTC
TACAAACGTTCGCTGCAATGACGGAAGCATTCCAGGTTATTACACCCGCC
CATCGACAACAAATTGTTCAAAAAATGGCTCATCTTTTTAGAAGGAGGA
TGGTATTGTTTTAACAACAATACTTGTGAATCCCGTAGACGAACTCATTAT
GATTTATTTCATCAGAATTTTGGTCTTCTGAACGGCAACTTGGAGGAATT
CTTTCTAATAATGAGCGAATCAATCCAAATTTTCATGACTATAATTCAGTG
TATATTCCTTACTGTTCGAGTGATTTGTGGTCTGGCAAACAATTAGAAAAA
ACTAATGGATTATATTTCCATGGATCTCGAATTTTAGACACAGTCGTTGAT
GATTTGACCCAAAACCAGCATTTTAAAAAGGTTCATGAAGTAGCTTTTGTT
GGATCGAGCGCTGGTGGAATCGGAGTTTTGTTGAATATCGATAGGCTGAA
AAGACGATTGAAGAAAAAACTTAAACGAAAGTATTTATTCATGGAATAG
TCGATTCAGCGTGGTTTCTCGATTATCCGGCGTATAGACAGTCAAACTGTA
CCCATATTTACGAATGCCCTCCAGAAATGCCCTTAGAAATGGAATGAAA
TTATGGAATCCTCGAATTCCGAGAAGATGCAAGAAATTCCAAGGTCGCGG
TAGGGAATGGAAATGTTTCATGGGTCCTGTCATATATAGGCACTTGAAAA
ATCCAACTTTCATTACAAAGTCTATTTGATGACGCTCAACTGCAGATGT
CAAAAGTCCCGATTTTAGAAGGAGGATCTAACAAAAGTTTTCATACATT
CAACAATTAGGAGGTTTTGCAGCTCAGACTTTGAGGCAGGCAAAAGGAGT
ATTCGCTCATTCTTGTGTTGATCATGAAATTTTAACAAAAAGTAATTGGGC
TTATGTTAGTGTCAACAATCAACGACTCCACGAAACGCTAAATTATTGGC
AAGCATATTTAGAAGGTGAAAAGAAAAAAATAAAGAAAAAAGTCCAAAA
AAATCCGAAACTTATCAAAACCGGCAAGTCTCCATGTAAAAACTTGAGAA
AGCCCAAGTTTTCTGGAAACATTGATCAAAGTAAATACCAATTGATTGAC
TCTTGCCACATTAGTCAAATTACGAGCTACAAAATACAGTTACCCCATAAT
CGAACTTTATCAAGATGTGCTAATGCCATTCCTTTGATTCCTTTATGCAAT
CCAACATGTTCACCGCTTTCCCACCCGATATCTGGTCTCAGTATGTCCTTC
ATTGATCTACTGGAATTGTATAACGTTCGCATAAACTTAATTGCGAAATCG
TTGGGTATCTCAATGGAACAATTGCGAAAAATGAACACTCAACAACAAAT
AAGTTTACTTTATTGTAGCAGTCGATAAATTTTGTTTGGTTAACGAAACCT
ATTCTTATCTCAGACCTACCTCTAATAATTGATGATTTTTATGGCACATCT
CACTCAATTAAATCCATCGATCTAGCTCTAATTCAAGATTTTAGATGGTTT
TTTATGTTATGCATTTAACAATATTTTGTTATCTTTTCTGTTTTTAGTTGAC
TCTAGAATTGAATTTGAAAATTATTCTTTACTCATGATACTACCTCTTGAT
AGTATATTTCATATGGAATTCTTCTTATTATTTATTATTAATATTATTATT
ATTATTATTGGTTTTCACATAAATCTAGCTTCAAATATTGATTTTATTGA
ATTATAATGAAAAGTCGATTTGTGATTTGTACAAATGAATCTATAAATAT
ATCATGTTTATGAAAAAAAAAAAAA (SEQ ID NO: 9)

FIG. 6A

SMED-NOTUM protein

MKSYLILNTLLLSLLKINGFSKSSWFSSKTSLIFDRINKLNDPQSSNSIHSRKYQ
YFQLKKFPNSTNVRCNDGSIPGYYTRPSTTNCSKKWLIFLEGGWYCFNNNTC
ESRRRTHYDLFSSEFWSSERQLGGILSNNERINPNFHDYNSVYIPYCSSDLWSG
KQLEKTNGLYFHGSRILDTVVDDLTQNQHFKKVHEVAFVGSSAGGIGVLLNI
DRLKRRLKKKLKRKVFIHGIVDSAWFLDYPAYRQSNCTHIYECPPENALRNG
MKLWNPRIPRRCKKFQGRGREWKCFMGPVIYRHLKNPTFIIQSLFDDAQLQM
SKVPILEGGSNKKFSYIQQLGGFAAQTLRQAKGVFAHSCVDHEILTKSNWAY
VSVNNQRLHETLNYWQAYLEGEKKKIKKKVQKNPKLIKTGKSPCKNLRKPK
FSGNIDQSKYQLIDSCHISQITSYKIQLPHNRTLSRCANAIPLIPLCNPTCSPLSHP
ISGLSMSFIDLLELYNVRINLIAKSLGISMEQLRKMNTQQQISLLYCSSR (SEQ ID NO: 10)

FIG. 6B

Homo sapiens NOTUM, complete cds

```
GCGGGCCGCAGCCAGCGCACCCAGACCCTGCGCTGCCCTCGGACGGCCGGGCGCGGAGCC
CCAGCTGCGGAGGCCGACGGCACCCGGCCCCGAGCGCCTCGACGCCGAGCCGCGCGCGCC
TTCTCCGCCAGGCCCGGCGGGCGGGAGCGGGGGCGAGGGAGCAGGAGCGGCCAGTGCCCC
CGACACCCCCGGCCCGGCACCCCCGGCCCGGCATCCCCCGCCGCCGCCGCCGCCTCA
AGGCCGCCCGCTCCCCGCAGGTGGACGCGGCCATGGCCGAGGGGTGCGCGTGCTGCTGC
TGCTGAGCCTGCTGCACTGCGCCGGGGGCAGCGAGGGCAGGAAGACCTGGCGGCGCCGGG
GTCAGCAGCCGCCTCCTCCCCGCGGACCGAGGCGGCGCCGGCGGCCGGACAGCCCGTGG
AGAGCTTCCCGCTGGACTTCACGGCCGTGGAGGGTAACATGGACAGCTTCATGGCGCAAG
TCAAGAGCCTGGCGCAGTCCCTGTACCCCTGCTCCGCGCAGCAGCTCAACGAGGACCTGC
GCCTGCACCTCCTACTCAACACCTCGGTGACCTGCAACGACGGCAGCCCCGCCGGCTACT
ACCTGAAGGAGTCCAGGGGCAGCCGGCGGTGGCTCCTCTTCCTGGAAGGCGGCTGGTACT
GCTTCAACCGCGAGAACTGCGACTCCAGATACGACACCATGCGGCGCCTCATGAGCTCCC
GGGACTGGCCGCGCACTCGCACAGGCACAGGGATCCTGTCCTCACAGCCGGAGGAGAACC
CCTACTGGTGGAACGCAAACATGGTCTTCATCCCCTACTGCTCCAGTGATGTTTGGAGCG
GGGCTTCATCCAAGTCTGAGAAGAACGAGTACGCCTTCATGGGCGCCCTCATCATCCAGG
AGGTGGTGCGGGAGCTTCTGGGCAGAGGGCTGAGCGGGGCCAAGGTGCTGCTGCTGGCCG
GGAGCAGCGCGGGGGGCACCGGGGTGCTCCTGAATGTGGACCGTGTGGCTGAGCAGCTGG
AGAAGCTGGGCTACCCAGCCATCCAGGTGCGAGGCCTGGCTGACTCCGGCTGGTTCCTGG
ACAACAAGCAGTATCGCCACACAGACTGCGTCGACACGATCACGTGCGCGCCCACGGAGG
CCATCCGCCGTGGCATCAGGTACTGGAACGGGGTGGTCCCGGAGCGCTGCCGACGCCAGT
TCCAGGAGGGCGAGGAGTGGAACTGCTTCTTTGGCTACAAGGTCTACCCGACCCTGCGCT
GCCCTGTGTTCGTGGTGCAGTGGCTGTTTGACGAGGCACAGCTGACGGTGGACAACGTGC
ACCTGACGGGGCAGCCGGTGCAGGAGGGCCTGCGGCTGTACATCCAGAACCTCGGCCGCG
AGCTGCGCCACACACTCAAGGACGTGCCGGCCAGCTTTGCCCCCGCCTGCCTCTCCCATG
AGATCATCATCCGGAGCCACTGGACGGATGTCCAGGTGAAGGGGACGTCGCTGCCCCGAG
CACTGCACTGCTGGGACAGGAGCCTCCATGACAGCCACAAGGCCAGCAAGACCCCCCTCA
AGGGCTGCCCCGTCCACCTGGTGGACAGCTGCCCCTGGCCCCACTGCAACCCCTCATGCC
CCACCGTCCGAGACCAGTTCACGGGGCAAGAGATGAACGTGGCCCAGTTCCTCATGCACA
TGGGCTTCGACATGCAGACGGTGGCCCAGCCGCAGGGACTGGAGCCCAGTGAGCTGCTGG
GGATGCTGAGCAACGGAAGCTAGGCAGACTGTCTGGAGGAGGAGCCGGCACTGAGGGGCC
CAGACACCCGCTGCCCCAGTGCCACCTCACCCCCACCAGCAGGCCCTCCCGTCTCTTCG
GGACAGGGCCCCAGCCGTCCCCCTGTCTGGGTCTGCCCACTGCCCTCCTGCCCCGGCTT
TCCCTGCCCCTCTCCCACAGCCCAGCCAGAGACAAGGGACCTGCTGTCATCCCCATCTGT
GGCCTGGGGGTCCTTCCTGACAACGAGGGGGTAGCCAGAAGAGAAGCACTGGATTCCTCA
GTCCACCAGCTCAGACAGCACCCACCGGCCCCACCCATCAAGCCCTTTTATATTATTTTA
TAAAGTGACTTTTTTATTACTTTAATTTTTTAAAAAAAGGAAAATAAGAATATATGATGA
ATGATATTGTTTTGTAACTTTTTAAAAATGATTTTAAAGAGACAAAAAAGAACCTCAAAA
AAAAAAAAAAAAAAAAAAAAAAAAAAAAAAAAAAAAAAAAAAAAAAAAAAAAAAAAAAAA
AAA (SEQ ID NO: 11)
```

FIG. 7A

Homo sapiens NOTUM protein

MGRGVRVLLLLSLLHCAGGSEGRKTWRRRGQQPPPPPRTEAAPAAGQPVESFPLDFTAVEGNMDSFMAQ
VKSLAQSLYPCSAQQLNEDLRLHLLLNTSVTCNDGSPAGYYLKESRGSRRWLLFLEGGWYCFNRENCDSR
YDTMRRLMSSRDWPRTRTGTGILSSQPEENPYWWNANMVFIPYCSSDVWSGASSKSEKNEYAFMGALIIQ
EVVRELLGRGLSGAKVLLLAGSSAGGTGVLLNVDRVAEQLEKLGYPAIQVRGLADSGWFLDNKQYRHTD
CVDTITCAPTEAIRRGIRYWNGVVPERCRRQFQEGEEWNCFFGYKVYPTLRCPVFVVQWLFDEAQLTVDN
VHLTGQPVQEGLRLYIQNLGRELRHTLKDVPASFAPACLSHEIIRSHWTDVQVKGTSLPRALHCWDRSLH
DSHKASKTPLKGCPVHLVDSCPWPHCNPSCPTVRDQFTGQEMNVAQFLMHMGFDMQTVAQPQGLEPSEL
LGMLSNGS (SEQ ID NO: 12)

FIG. 7B

SEQUENCE LISTING

```
<160> NUMBER OF SEQ ID NOS: 16

<210> SEQ ID NO 1
<211> LENGTH: 22
<212> TYPE: DNA
<213> ORGANISM: Artificial
<220> FEATURE:
<223> OTHER INFORMATION: primer for notum dsRNA and riboprobes

<400> SEQUENCE: 1
aaaatttctg aggatcgaaa aa                                          22

<210> SEQ ID NO 2
<211> LENGTH: 22
<212> TYPE: DNA
<213> ORGANISM: Artificial
<220> FEATURE:
<223> OTHER INFORMATION: primer for notum dsRNA and riboprobes
```

<400> SEQUENCE: 2
aaaatttctg aggatcgaaa aa                                          22

<210> SEQ ID NO 3
<211> LENGTH: 20
<212> TYPE: DNA
<213> ORGANISM: Artificial
<220> FEATURE:
<223> OTHER INFORMATION: primer for notum dsRNA

<400> SEQUENCE: 3
tcgagtgatt tgtggtctgg                                             20

<210> SEQ ID NO 4
<211> LENGTH: 26
<212> TYPE: DNA
<213> ORGANISM: Artificial
<220> FEATURE:
<223> OTHER INFORMATION: primer for notum dsRNA

<400> SEQUENCE: 4
tgaagctaga tttatgtgaa aaacca                                      26

<210> SEQ ID NO 5
<211> LENGTH: 20
<212> TYPE: DNA
<213> ORGANISM: Artificial
<220> FEATURE:
<223> OTHER INFORMATION: primer for control dsRNA

<400> SEQUENCE: 5
tatccgctgg aagatggaac                                             20

<210> SEQ ID NO 6
<211> LENGTH: 20
<212> TYPE: DNA
<213> ORGANISM: Artificial
<220> FEATURE:
<223> OTHER INFORMATION: primer for control dsRNA

<400> SEQUENCE: 6
cggtacttcg tccacaaaca                                             20

<210> SEQ ID NO 7
<211> LENGTH: 24
<212> TYPE: DNA
<213> ORGANISM: Artificial
<220> FEATURE:
<223> OTHER INFORMATION: PCR primer for notum mRNA

<400> SEQUENCE: 7
tatttggttt ttattccagg atca                                        24

<210> SEQ ID NO 8
<211> LENGTH: 24
<212> TYPE: DNA
<213> ORGANISM: Artificial
<220> FEATURE:
<223> OTHER INFORMATION: PCR primer for notum mRNA

<400> SEQUENCE: 8
atccattgat cttcaatagg ctca                                        24

<210> SEQ ID NO 9
<211> LENGTH: 2106

<212> TYPE: DNA
<213> ORGANISM: S. mediterranea

<400> SEQUENCE: 9

```
ttataaatat cgacgatcac ataactaacc aaagttaaat ctaaaatttc tgaggatcga    60
aaaaattgaa aactattctt caaatatttg gtttttattc caggatcaaa aaatgaaatc   120
atatctgata ttgaatactc ttctattgag cctattgaag atcaatggat tttccaaatc   180
gtcttggttc agttcaaaga cttcgttgat tttcgatcga atcaacaaat tgaatgatcc   240
gcaatccagt aattcaattc acagtagaaa atatcagtat tttcagttga aaaaatttcc   300
aaattctaca aacgttcgct gcaatgacgg aagcattcca ggttattaca cccgcccatc   360
gacaacaaat tgttcaaaaa aatggctcat cttttagaa ggaggatggt attgttttaa    420
caacaatact tgtgaatccc gtagacgaac tcattatgat ttattttcat cagaattttg   480
gtcttctgaa cggcaacttg gaggaattct ttctaataat gagcgaatca atccaaattt   540
tcatgactat aattcagtgt atattcctta ctgttcgagt gatttgtggt ctggcaaaca   600
attagaaaaa actaatggat tatatttcca tggatctcga attttagaca cagtcgttga   660
tgatttgacc caaaccagc attttaaaaa ggttcatgaa gtagcttttg ttggatcgag    720
cgctggtgga atcggagttt tgttgaatat cgataggctg aaaagacgat tgaagaaaaa   780
acttaaacga aaagtattta ttcatggaat agtcgattca gcgtggtttc tcgattatcc   840
ggcgtataga cagtcaaact gtacccatat ttacgaatgc cctccagaaa atgcccttag   900
aaatggaatg aaattatgga atcctcgaat tccgagaaga tgcaagaaat tccaaggtcg   960
cggtagggaa tggaaatgtt tcatgggtcc tgtcatatat aggcacttga aaaatccaac  1020
tttcattata caaagtctat ttgatgacgc tcaactgcag atgtcaaaag tcccgatttt  1080
agaaggagga tctaacaaaa agttttcata cattcaacaa ttaggaggtt ttgcagctca  1140
gactttgagg caggcaaaag gagtattcgc tcattcttgt gttgatcatg aaattttaac  1200
aaaaagtaat tgggcttatg ttagtgtcaa caatcaacga ctccacgaaa cgctaaatta  1260
ttggcaagca tatttagaag gtgaaaagaa aaaataaag aaaaaagtcc aaaaaaatcc   1320
gaaacttatc aaaaccggca agtctccatg taaaaacttg agaaagccca gttttctgg   1380
aaacattgat caaagtaaat accaattgat tgactcttgc cacattagtc aaattacgag  1440
ctacaaaata cagttacccc ataatcgaac tttatcaaga tgtgctaatg ccattccttt  1500
gattccttta tgcaatccaa catgttcacc gctttcccac ccgatatctg gtctcagtat  1560
gtccttcatt gatctactgg aattgtataa cgttcgcata aacttaattg cgaaatcgtt  1620
gggtatctca atggaacaat tgcgaaaaat gaacactcaa caacaaataa gtttacttta  1680
ttgtagcagt cgataaattt tgtttggtta acgaaaccta ttcttatctc agacctacct  1740
ctaataattg atgatttttt atggcacatc tcactcaatt aaatccatcg atctagctct  1800
aattcaagat tttagatggt tttttatgtt atgcatttaa caatatttt gttatctttt   1860
ctgtttttag ttgactctag aattgaattt gaaaattatt ctttactcat gatactacct  1920
cttgatagta tatttcatat ggaattcttc ttattatttt attattaata ttattattat  1980
tattattggt ttttcacata aatctagctt caaatattga tttttattga attataatga  2040
aaagtcgat ttgtgatttg tacaaatgaa tctataaata tatcatgttt atgaaaaaaa   2100
aaaaaa                                                             2106
```

<210> SEQ ID NO 10

<211> LENGTH: 527
<212> TYPE: PRT
<213> ORGANISM: S. mediterranea

<400> SEQUENCE: 10

```
Met Lys Ser Tyr Leu Ile Leu Asn Thr Leu Leu Ser Leu Leu Lys
1               5                   10                  15

Ile Asn Gly Phe Ser Lys Ser Ser Trp Phe Ser Ser Lys Thr Ser Leu
            20                  25                  30

Ile Phe Asp Arg Ile Asn Lys Leu Asn Asp Pro Gln Ser Ser Asn Ser
        35                  40                  45

Ile His Ser Arg Lys Tyr Gln Tyr Phe Gln Leu Lys Lys Phe Pro Asn
    50                  55                  60

Ser Thr Asn Val Arg Cys Asn Asp Gly Ser Ile Pro Gly Tyr Tyr Thr
65                  70                  75                  80

Arg Pro Ser Thr Thr Asn Cys Ser Lys Lys Trp Leu Ile Phe Leu Glu
                85                  90                  95

Gly Gly Trp Tyr Cys Phe Asn Asn Asn Thr Cys Glu Ser Arg Arg Arg
            100                 105                 110

Thr His Tyr Asp Leu Phe Ser Ser Glu Phe Trp Ser Ser Glu Arg Gln
        115                 120                 125

Leu Gly Gly Ile Leu Ser Asn Asn Glu Arg Ile Asn Pro Asn Phe His
    130                 135                 140

Asp Tyr Asn Ser Val Tyr Ile Pro Tyr Cys Ser Ser Asp Leu Trp Ser
145                 150                 155                 160

Gly Lys Gln Leu Glu Lys Thr Asn Gly Leu Tyr Phe His Gly Ser Arg
                165                 170                 175

Ile Leu Asp Thr Val Val Asp Asp Leu Thr Gln Asn Gln His Phe Lys
            180                 185                 190

Lys Val His Glu Val Ala Phe Val Gly Ser Ser Ala Gly Gly Ile Gly
        195                 200                 205

Val Leu Leu Asn Ile Asp Arg Leu Lys Arg Arg Leu Lys Lys Lys Leu
    210                 215                 220

Lys Arg Lys Val Phe Ile His Gly Ile Val Asp Ser Ala Trp Phe Leu
225                 230                 235                 240

Asp Tyr Pro Ala Tyr Arg Gln Ser Asn Cys Thr His Ile Tyr Glu Cys
                245                 250                 255

Pro Pro Glu Asn Ala Leu Arg Asn Gly Met Lys Leu Trp Asn Pro Arg
            260                 265                 270

Ile Pro Arg Arg Cys Lys Lys Phe Gln Gly Arg Gly Arg Glu Trp Lys
        275                 280                 285

Cys Phe Met Gly Pro Val Ile Tyr Arg His Leu Lys Asn Pro Thr Phe
    290                 295                 300

Ile Ile Gln Ser Leu Phe Asp Asp Ala Gln Leu Gln Met Ser Lys Val
305                 310                 315                 320

Pro Ile Leu Glu Gly Gly Ser Asn Lys Lys Phe Ser Tyr Ile Gln Gln
                325                 330                 335

Leu Gly Gly Phe Ala Ala Gln Thr Leu Arg Gln Ala Lys Gly Val Phe
            340                 345                 350

Ala His Ser Cys Val Asp His Glu Ile Leu Thr Lys Ser Asn Trp Ala
        355                 360                 365

Tyr Val Ser Val Asn Asn Gln Arg Leu His Glu Thr Leu Asn Tyr Trp
    370                 375                 380

Gln Ala Tyr Leu Glu Gly Glu Lys Lys Lys Ile Lys Lys Lys Val Gln
```

```
                385                 390                 395                 400
Lys Asn Pro Lys Leu Ile Lys Thr Gly Lys Ser Pro Cys Lys Asn Leu
                405                 410                 415

Arg Lys Pro Lys Phe Ser Gly Asn Ile Asp Gln Ser Lys Tyr Gln Leu
                420                 425                 430

Ile Asp Ser Cys His Ile Ser Gln Ile Thr Ser Tyr Lys Ile Gln Leu
                435                 440                 445

Pro His Asn Arg Thr Leu Ser Arg Cys Ala Asn Ala Ile Pro Leu Ile
            450                 455                 460

Pro Leu Cys Asn Pro Thr Cys Ser Pro Leu Ser His Pro Ile Ser Gly
465                 470                 475                 480

Leu Ser Met Ser Phe Ile Asp Leu Leu Glu Leu Tyr Asn Val Arg Ile
                485                 490                 495

Asn Leu Ile Ala Lys Ser Leu Gly Ile Ser Met Glu Gln Leu Arg Lys
            500                 505                 510

Met Asn Thr Gln Gln Gln Ile Ser Leu Leu Tyr Cys Ser Ser Arg
            515                 520                 525
```

<210> SEQ ID NO 11
<211> LENGTH: 2281
<212> TYPE: DNA
<213> ORGANISM: Homo sapiens

<400> SEQUENCE: 11

```
gcgggccgca gccagcgcac ccagaccctg cgctgccctc ggacggccgg gcgcggagcc      60
ccagctgcgg aggccgacgg cacccggccc cgagcgcctc gacgccgagc cgcgcgcgcc     120
ttctccgcca ggcccggcgg gcgggagcgg gggcgaggga gcaggagcgg ccagtgcccc     180
cgacaccccc ggcccggcac ccccggcccg gcatccccg ccgccgccgc cgccgcctca      240
aggccgcccg ctccccgcag gtggacgcgg ccatgggccg aggggtgcgc gtgctgctgc     300
tgctgagcct gctgcactgc gccggggggca gcgaggcag aagacctgg cggcgccggg      360
gtcagcagcc gcctcctccc ccgcggaccg aggcggcgcc ggcggccgga cagcccgtgg     420
agagcttccc gctggacttc acggccgtgg agggtaacat ggacagcttc atggcgcaag     480
tcaagagcct ggcgcagtcc ctgtaccccct gctccgcgca gcagctcaac gaggacctgc     540
gcctgcacct cctactcaac acctcggtga cctgcaacga cggcagcccc gccggctact     600
acctgaagga gtccagggga gccggcggt ggctcctctt cctggaaggc ggctggtact      660
gcttcaaccg cgagaactgc gactccagat acgacaccat cgccgcctc atgagctccc     720
gggactggcc gcgcactcgc acaggcacag ggatcctgtc ctcacagccg aggagaaacc     780
cctactggtg gaacgcaaac atggtcttca tccccctatcg ctccagtgat gtttggagcg     840
ggcttcatc caagtctgag aagaacgagt acgccttcat gggcgccctc atcatccagg      900
aggtggtgcg ggagcttctg gcagagggc tgagcgggc caaggtgctg ctgctggccg      960
ggagcagcgc gggggcacc gggtgctcc tgaatgtgga ccgtgtggct gagcagctgg     1020
agaagctggg ctacccagcc atccaggtgc gaggcctggc tgactccggc tggttcctgg     1080
acaacaagca gtatcgccac acagactgcg tcgacacgat cacgtgcgcg cccacggagg     1140
ccatccgccg tggcatcagg tactggaacg gggtggtccc ggagcgctgc cgacgccagt     1200
tccaggaggg cgaggagtgg aactgcttct ttggctacaa ggtctacccg accctgcgct     1260
gccctgtgtt cgtggtgcag tggctgtttg acgaggcaca gctgacgtg acaacgtgc      1320
acctgacggg gcagccggtg caggagggcc tgcggctgta catccagaac ctcggccgcg     1380
```

```
agctgcgcca cacactcaag gacgtgccgg ccagctttgc ccccgcctgc ctctcccatg    1440
agatcatcat ccggagccac tggacggatg tccaggtgaa ggggacgtcg ctgccccgag    1500
cactgcactg ctgggacagg agcctccatg acagccacaa ggccagcaag acccccctca    1560
agggctgccc cgtccacctg gtggacagct gcccctggcc ccactgcaac ccctcatgcc    1620
ccaccgtccg agaccagttc acggggcaag agatgaacgt ggcccagttc ctcatgcaca    1680
tgggcttcga catgcagacg gtggcccagc cgcagggact ggagcccagt gagctgctgg    1740
ggatgctgag caacggaagc taggcagact gtctggagga ggagccggca ctgaggggcc    1800
cagacacccg ctgccccagt gccacctcac cccccaccag caggccctcc cgtctcttcg    1860
ggacagggcc ccagccgtcc ccctgtctg gtctgccca ctgccctcct gccccggctt    1920
tccctgcccc tctcccacag cccagccaga gacaagggac ctgctgtcat ccccatctgt    1980
ggcctggggg tccttcctga caacgagggg gtagccagaa gagaagcact ggattcctca    2040
gtccaccagc tcagacagca cccaccggcc ccacccatca agccctttta tattatttta    2100
taaagtgact tttttattac tttaattttt taaaaaagg aaaataagaa tatatgatga    2160
atgatattgt tttgtaactt tttaaaaatg attttaaaga gacaaaaaag aacctcaaaa    2220
aaaaaaaaaa aaaaaaaaaa aaaaaaaaaa aaaaaaaaaa aaaaaaaaaa aaaaaaaaaa    2280
a                                                                   2281

<210> SEQ ID NO 12
<211> LENGTH: 496
<212> TYPE: PRT
<213> ORGANISM: Homo sapiens

<400> SEQUENCE: 12

Met Gly Arg Gly Val Arg Val Leu Leu Leu Ser Leu Leu His Cys
1               5                   10                  15

Ala Gly Gly Ser Glu Gly Arg Lys Thr Trp Arg Arg Gly Gln Gln
                20                  25                  30

Pro Pro Pro Pro Arg Thr Glu Ala Ala Pro Ala Ala Gly Gln Pro
            35                  40                  45

Val Glu Ser Phe Pro Leu Asp Phe Thr Ala Val Glu Gly Asn Met Asp
    50                  55                  60

Ser Phe Met Ala Gln Val Lys Ser Leu Ala Gln Ser Leu Tyr Pro Cys
65                  70                  75                  80

Ser Ala Gln Gln Leu Asn Glu Asp Leu Arg Leu His Leu Leu Asn
                85                  90                  95

Thr Ser Val Thr Cys Asn Asp Gly Ser Pro Ala Gly Tyr Tyr Leu Lys
            100                 105                 110

Glu Ser Arg Gly Ser Arg Arg Trp Leu Leu Phe Leu Glu Gly Gly Trp
        115                 120                 125

Tyr Cys Phe Asn Arg Glu Asn Cys Asp Ser Arg Tyr Asp Thr Met Arg
    130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
            180                 185                 190

Ser Lys Ser Glu Lys Asn Glu Tyr Ala Phe Met Gly Ala Leu Ile Ile
        195                 200                 205
```

Gln Glu Val Val Arg Glu Leu Leu Gly Arg Gly Leu Ser Gly Ala Lys
210                 215                 220

Val Leu Leu Leu Ala Gly Ser Ser Ala Gly Gly Thr Gly Val Leu Leu
225                 230                 235                 240

Asn Val Asp Arg Val Ala Glu Gln Leu Glu Lys Leu Gly Tyr Pro Ala
            245                 250                 255

Ile Gln Val Arg Gly Leu Ala Asp Ser Gly Trp Phe Leu Asp Asn Lys
        260                 265                 270

Gln Tyr Arg His Thr Asp Cys Val Asp Thr Ile Thr Cys Ala Pro Thr
            275                 280                 285

Glu Ala Ile Arg Arg Gly Ile Arg Tyr Trp Asn Gly Val Val Pro Glu
        290                 295                 300

Arg Cys Arg Arg Gln Phe Gln Glu Gly Glu Glu Trp Asn Cys Phe Phe
305                 310                 315                 320

Gly Tyr Lys Val Tyr Pro Thr Leu Arg Cys Pro Val Phe Val Val Gln
            325                 330                 335

Trp Leu Phe Asp Glu Ala Gln Leu Thr Val Asp Asn Val His Leu Thr
        340                 345                 350

Gly Gln Pro Val Gln Glu Gly Leu Arg Leu Tyr Ile Gln Asn Leu Gly
            355                 360                 365

Arg Glu Leu Arg His Thr Leu Lys Asp Val Pro Ala Ser Phe Ala Pro
370                 375                 380

Ala Cys Leu Ser His Glu Ile Ile Arg Ser His Trp Thr Asp Val
385                 390                 395                 400

Gln Val Lys Gly Thr Ser Leu Pro Arg Ala Leu His Cys Trp Asp Arg
            405                 410                 415

Ser Leu His Asp Ser His Lys Ala Ser Lys Thr Pro Leu Lys Gly Cys
        420                 425                 430

Pro Val His Leu Val Asp Ser Cys Pro Trp Pro His Cys Asn Pro Ser
            435                 440                 445

Cys Pro Thr Val Arg Asp Gln Phe Thr Gly Gln Glu Met Asn Val Ala
450                 455                 460

Gln Phe Leu Met His Met Gly Phe Asp Met Gln Thr Val Ala Gln Pro
465                 470                 475                 480

Gln Gly Leu Glu Pro Ser Glu Leu Leu Gly Met Leu Ser Asn Gly Ser
            485                 490                 495

<210> SEQ ID NO 13
<211> LENGTH: 467
<212> TYPE: PRT
<213> ORGANISM: Mus musculus

<400> SEQUENCE: 13

Met Lys Ser Tyr Leu Ile Leu Asn Thr Leu Leu Ser Leu Leu Lys
1               5                   10                  15

Ile Asn Gly Phe Ser Lys Ser Ser Trp Phe Ser Ser Lys Thr Ser Leu
            20                  25                  30

Ile Phe Asp Arg Ile Asn Lys Leu Asn Asp Pro Gln Ser Ser Asn Ser
        35                  40                  45

Ile His Ser Arg Lys Tyr Gln Tyr Phe Gln Leu Lys Lys Phe Pro Asn
    50                  55                  60

Ser Thr Asn Val Arg Cys Asn Asp Gly Ser Ile Pro Gly Tyr Tyr Thr
65                  70                  75                  80

Arg Pro Ser Thr Thr Asn Cys Ser Lys Lys Trp Leu Ile Phe Leu Glu

```
                85                  90                  95
Gly Gly Trp Tyr Cys Phe Asn Arg Glu Asn Cys Asp Ser Arg Tyr Ser
            100                 105                 110

Thr Met Arg Arg Leu Met Ser Ser Lys Asp Trp Pro His Thr Arg Thr
        115                 120                 125

Gly Thr Gly Ile Leu Ser Ser Gln Pro Glu Glu Asn Pro His Trp Trp
130                 135                 140

Asn Ala Asn Met Val Phe Ile Pro Tyr Cys Ser Ser Asp Val Trp Ser
145                 150                 155                 160

Gly Ala Ser Pro Lys Ser Asp Lys Asn Glu Tyr Ala Phe Met Gly Ser
            165                 170                 175

Leu Ile Ile Gln Glu Val Val Arg Glu Leu Leu Gly Lys Gly Leu Ser
            180                 185                 190

Gly Ala Lys Val Leu Leu Leu Ala Gly Ser Ser Ala Gly Gly Thr Gly
            195                 200                 205

Val Leu Leu Asn Val Asp Arg Val Ala Glu Leu Leu Glu Glu Leu Gly
            210                 215                 220

Tyr Pro Ser Ile Gln Val Arg Gly Leu Ala Asp Ser Gly Trp Phe Leu
225                 230                 235                 240

Asp Asn Lys Gln Tyr Arg Arg Ser Asp Cys Ile Asp Thr Ile Asn Cys
            245                 250                 255

Ala Pro Thr Asp Ala Ile Arg Arg Gly Ile Arg Tyr Trp Ser Gly Met
            260                 265                 270

Val Pro Glu Arg Cys Gln Arg Gln Phe Lys Glu Gly Glu Glu Trp Asn
            275                 280                 285

Cys Phe Phe Gly Tyr Lys Val Tyr Pro Thr Leu Arg Cys Pro Val Phe
            290                 295                 300

Val Val Gln Trp Leu Phe Asp Glu Ala Gln Leu Thr Val Asp Asn Val
305                 310                 315                 320

His Leu Thr Gly Gln Pro Val Gln Glu Gly Gln Trp Leu Tyr Ile Gln
            325                 330                 335

Asn Leu Gly Arg Glu Leu Arg Gly Thr Leu Lys Asp Val Gln Ala Ser
            340                 345                 350

Phe Ala Pro Ala Cys Leu Ser His Glu Ile Ile Ile Arg Ser Tyr Trp
            355                 360                 365

Thr Asp Val Gln Val Lys Gly Thr Ser Leu Pro Arg Ala Leu His Cys
            370                 375                 380

Trp Asp Arg Ser Phe His Asp Ser His Lys Ala Ser Lys Thr Pro Met
385                 390                 395                 400

Lys Gly Cys Pro Phe His Leu Val Asp Ser Cys Pro Trp Pro His Cys
            405                 410                 415

Asn Pro Ser Cys Pro Thr Ile Arg Asp Gln Phe Thr Gly Gln Glu Met
            420                 425                 430

Asn Val Ala Gln Phe Leu Met His Met Gly Phe Asp Val Gln Thr Val
            435                 440                 445

Ala Gln Gln Gln Gly Met Glu Pro Ser Lys Leu Leu Gly Met Leu Ser
            450                 455                 460

Asn Gly Asn
465

<210> SEQ ID NO 14
<211> LENGTH: 536
<212> TYPE: PRT
<213> ORGANISM: Tribolium castaneum
```

<400> SEQUENCE: 14

```
Met Arg Leu Val Val Thr Gln Leu Met Ala Leu Trp Leu Gly Leu Ser
1               5                   10                  15

Met Ala Phe Pro Gly Thr Gly Arg Arg Asn Thr His Asp Met Asp Thr
            20                  25                  30

Pro Ile Tyr Thr Asn Asn Ile Gln Arg Phe Val His Arg Gln Glu Asn
        35                  40                  45

Lys Asn Glu Glu Ile Arg Ala Leu Lys Arg Val Phe Leu Ser Asn Arg
    50                  55                  60

Ser Val Thr Cys Asn Asp Gly Ser Gln Ala Gly Phe Tyr Leu Arg Lys
65                  70                  75                  80

Ser Tyr Thr Ser Lys Lys Trp Ile Ile Phe Leu Glu Gly Gly Trp Tyr
                85                  90                  95

Cys Tyr Asp His His Ser Cys Arg Asn Arg Trp Leu Lys Gln Arg His
            100                 105                 110

Tyr Met Thr Ser Thr Gly Trp Pro Asp Ala Arg Asp Ile Gly Gly Ile
        115                 120                 125

Leu Ser Gly Ser Met Glu Glu Asn Pro Phe Trp Trp Asn Ala Asn His
    130                 135                 140

Val Phe Ile Pro Tyr Cys Thr Ser Asp Ser Trp Ser Gly Ser Lys Pro
145                 150                 155                 160

His Ser Arg Ser Glu Thr Phe Ser Phe Met Gly Ser Ile Leu Val Gln
                165                 170                 175

Gln Val Val Gln Asp Leu Leu Thr Leu Gly Leu Glu Asn Ser Thr Asp
            180                 185                 190

Leu Leu Leu Thr Gly Ser Ser Ala Gly Gly Thr Gly Val Met Leu Asn
        195                 200                 205

Leu Asp Pro Val Arg Glu Phe Leu His Asp Lys Lys Gly Leu Arg His
    210                 215                 220

Ile Val Val Lys Gly Val Thr Asp Ser Gly Trp Phe Leu Asp Arg Thr
225                 230                 235                 240

Pro Tyr Ala Pro Thr Leu Lys Pro Ala Val Asp Ala Ile Arg Arg Gly
                245                 250                 255

Ile Asp Leu Trp Gly Lys Val Pro His Arg Cys Lys Glu Leu Tyr
            260                 265                 270

Pro Asp Glu Pro Trp Arg Cys Tyr Phe Gly Tyr Arg Leu Tyr Pro Thr
        275                 280                 285

Leu Lys Thr Glu Leu Phe Val Phe Gln Trp Leu Phe Asp Glu Ala Gln
    290                 295                 300

Met Asp Ala Asp Asn Val Gly Ala Pro Val Thr Lys Gln Gln Trp Asp
305                 310                 315                 320

Tyr Ile His Lys Met Gly Asp Ala Leu Arg Gln Ser Phe Glu Asn Val
                325                 330                 335

Ser Ala Val Phe Ala Pro Ser Cys Ile Ser His Ser Val Leu Thr Lys
            340                 345                 350

Arg Asp Trp Gln Asn Val Lys Ile Asp Asp Ile Ser Ile Pro Glu Ala
        355                 360                 365

Leu His Cys Trp Glu Gln Lys Leu His Arg Arg Ile Lys Lys Ser
    370                 375                 380

Arg Asn Thr Lys Met Phe Ala Asp Gln Pro Lys Pro Leu Arg Arg Gln
385                 390                 395                 400

Thr Leu Asn Ser Thr Leu Thr Asp Glu Val Gly Gln Lys Lys Lys Arg
```

```
            405                 410                 415
Arg Arg Lys Asn Arg Lys Ser Arg Lys Gly Lys Lys Lys Asp Ala
            420                 425                 430

Val Gln Ala Ser Gly Asn Arg Thr Ser Glu Leu Asn Leu Met Gly Arg
            435                 440                 445

Asp Asp Ile Ser Ile Pro Glu Ala Leu His Cys Trp Glu Gln Lys Leu
            450                 455                 460

His Arg Arg Ile Lys Lys Ser Arg Asn Thr Lys Met Phe Ala Asp
465             470                 475                 480

Gln Pro Lys Pro Leu Arg Arg Gln Thr Leu Asn Ser Thr Leu Thr Asp
            485                 490                 495

Glu Val Gly Gln Lys Lys Arg Arg Lys Asn Arg Lys Ser Arg
            500                 505                 510

Lys Gly Lys Lys Lys Asp Ala Val Gln Ala Ser Gly Asn Arg Thr
            515                 520                 525

Ser Glu Leu Asn Leu Met Gly Arg
            530                 535

<210> SEQ ID NO 15
<211> LENGTH: 671
<212> TYPE: PRT
<213> ORGANISM: Drosophila melanogaster

<400> SEQUENCE: 15

Met Ala Val Glu Gln Ile Asp Lys Met Ala Ala Lys Ala Gly Glu Ala
1               5                   10                  15

Thr Asn Lys Trp Ile Lys Pro Gln Gln Pro Leu Leu Thr Leu Leu Leu
                20                  25                  30

Leu Leu Ala Thr Phe Ser Gln Leu Pro Ala Val Cys Ser Ser Ile
            35                  40                  45

Leu Asp Ala Ala Ser Leu Gln Glu Lys Asp Pro Leu Arg Asp Thr Ser
50              55                  60

Met Asn Met Ile Gln Arg Asn Tyr Met Val Met His Ser Ala Ser Gly
65              70                  75                  80

Ser Gly Asp His Ser Arg Ser Leu Lys Arg Ala Asn Leu Ala Asn Thr
                85                  90                  95

Ser Ile Thr Cys Asn Asp Gly Ser His Ala Gly Phe Tyr Leu Arg Lys
            100                 105                 110

His Pro Ser Ser Lys Lys Trp Ile Val Leu Leu Glu Gly Gly Trp His
            115                 120                 125

Cys Phe Asp Val Arg Ser Cys Arg Ser Arg Trp Met Arg Leu Arg His
            130                 135                 140

Leu Met Thr Ser Ser Gln Trp Pro Glu Thr Arg Asp Val Gly Gly Ile
145             150                 155                 160

Leu Ser Pro His Pro Glu Glu Asn Pro Tyr Trp His Asn Ala Asn His
                165                 170                 175

Val Leu Ile Pro Tyr Cys Ser Ser Asp Ser Trp Ser Gly Thr Arg Thr
            180                 185                 190

Glu Pro Asp Thr Ser Asp Arg Glu Asn Ser Trp Arg Phe Met Gly Ala
            195                 200                 205

Leu Ile Leu Arg Gln Val Ile Ala Glu Leu Ile Pro Val Gly Leu Gly
            210                 215                 220

Arg Val Pro Gly Gly Glu Leu Met Leu Val Gly Ser Ser Ala Gly Gly
225             230                 235                 240
```

-continued

Met Gly Val Met Leu Asn Leu Asp Arg Ile Arg Asp Phe Leu Val Asn
                245                 250                 255

Glu Lys Lys Leu Gln Ile Thr Val Arg Gly Val Ser Asp Ser Gly Trp
            260                 265                 270

Phe Leu Asp Arg Glu Pro Tyr Thr Pro Ala Ala Val Ala Ser Asn Glu
        275                 280                 285

Ala Val Arg Gln Gly Trp Lys Leu Trp Gln Gly Leu Leu Pro Glu Glu
    290                 295                 300

Cys Thr Lys Ser Tyr Pro Thr Glu Pro Trp Arg Cys Tyr Tyr Gly Tyr
305                 310                 315                 320

Arg Leu Tyr Pro Thr Leu Lys Thr Pro Leu Phe Val Phe Gln Trp Leu
                325                 330                 335

Phe Asp Glu Ala Gln Met Arg Val Asp Asn Val Gly Ala Pro Val Thr
            340                 345                 350

Pro Gln Gln Trp Asn Tyr Ile His Glu Met Gly Gly Ala Leu Arg Ser
        355                 360                 365

Ser Leu Asp Asn Val Ser Ala Val Phe Ala Pro Ser Cys Ile Gly His
    370                 375                 380

Gly Val Leu Phe Lys Arg Asp Trp Val Asn Ile Lys Ile Asp Asp Ile
385                 390                 395                 400

Ser Leu Pro Ser Ala Leu Arg Cys Trp Glu His Ser Thr Arg Ser Arg
                405                 410                 415

Arg His Asp Lys Leu Lys Arg Ser Thr Glu Pro Ser Thr Ala Val Ser
            420                 425                 430

His Pro Glu His Ala Asn Asn Gln Arg His Gln Arg His Arg Gln Arg
        435                 440                 445

Leu Gln Arg Gln Lys His Asn Asn Val Ala Gln Ser Gly Gly Gln Gln
    450                 455                 460

Arg Lys His Asn His Leu Ser Lys Glu Glu Arg Glu Arg Lys Arg
465                 470                 475                 480

Leu Arg Gln Glu Gln Arg Gln Arg Arg Lys Gln Arg Arg Gln Gln
                485                 490                 495

Gln Gln Lys Lys Ala Asn Gly Gly Gln Glu His Arg Asn Lys Lys Asp
            500                 505                 510

Asn Ser Pro Lys Ser Ser Asn Gly Asn Asp Gln Arg Lys Gln Arg Arg
        515                 520                 525

Arg Gln Gln Leu Thr Ala Glu Glu Arg Gln Glu Gln Arg Lys Arg Arg
    530                 535                 540

Arg Lys Ala Gln Gln Gln Met Lys Met Gln Arg Glu Gln Pro Ala
545                 550                 555                 560

Ala Gly Val Phe Leu Glu Ala Ser Ala Pro Gln Lys Thr Arg Ser Ser
                565                 570                 575

Asn Asn Ala Ser Ala Gly Thr Lys Ser Lys Arg His Arg Val Pro
            580                 585                 590

Arg Val Pro Glu Lys Cys Gly Leu Arg Leu Glu Arg Cys Ser Trp
        595                 600                 605

Pro Gln Cys Asn His Ser Cys Pro Thr Leu Thr Asn Pro Met Thr Gly
    610                 615                 620

Glu Glu Met Arg Phe Leu Glu Leu Leu Thr Ala Phe Gly Leu Asp Ile
625                 630                 635                 640

Glu Ala Val Ala Ala Ala Leu Gly Val Asp Met His Thr Leu Asn Asn
                645                 650                 655

Met Glu Arg Thr Glu Leu Val Asn Met Leu Thr Gln Gln Ala Asn

<210> SEQ ID NO 16
<211> LENGTH: 416
<212> TYPE: PRT
<213> ORGANISM: Nematostella vectensis

<400> SEQUENCE: 16

| | | | | | | | | | | | | | | |
|---|---|---|---|---|---|---|---|---|---|---|---|---|---|---|
| Met | Asp | Leu | Gln | Ala | Gln | Leu | Arg | Tyr | Met | Ala | Gln | Leu | Gln | Ala |
| 1 | | | | 5 | | | | | 10 | | | | | 15 |
| Cys | Glu | Gly | Asp | Leu | Pro | Ser | Leu | Ser | Ala | Phe | Asp | Leu | Lys | Leu | His |
| | | | 20 | | | | | 25 | | | | | 30 | | |
| Tyr | Leu | Thr | Asp | Val | Asn | Thr | Thr | Cys | Asn | Asp | Gly | Ser | Pro | Ala | Gly |
| | | 35 | | | | | 40 | | | | | 45 | | | |
| Tyr | Tyr | Leu | Lys | Glu | Ser | Pro | Lys | Ser | Lys | Arg | Trp | Leu | Val | Tyr | Leu |
| 50 | | | | | 55 | | | | | 60 | | | | | |
| Glu | Gly | Gly | Trp | Phe | Cys | Tyr | Asn | Gln | Met | Ser | Cys | Asn | Ile | Arg | Ala |
| 65 | | | | | 70 | | | | | 75 | | | | | 80 |
| Asn | Ser | Gln | Met | Arg | Tyr | Leu | Met | Thr | Ser | Lys | Asn | Trp | Ser | Lys | Thr |
| | | | | 85 | | | | | 90 | | | | | 95 | |
| Lys | Arg | Gly | Asn | Gly | Met | Leu | Ser | Pro | Gln | Pro | Glu | Glu | Asn | Pro | Asn |
| | | | | 100 | | | | | 105 | | | | | 110 | |
| Trp | Trp | Asn | Ala | Asn | His | Val | Leu | Ile | Pro | Tyr | Cys | Ser | Ser | Asp | Ala |
| | | | 115 | | | | | 120 | | | | | 125 | | |
| Trp | Ser | Gly | Asn | Ala | Ser | Arg | His | Glu | Thr | Gly | Glu | Lys | Phe | Ser | Phe |
| | 130 | | | | | 135 | | | | | 140 | | | | |
| Leu | Gly | Ala | Arg | Ile | Leu | Glu | Lys | Val | Ile | Glu | Asp | Leu | Leu | Pro | Arg |
| 145 | | | | | 150 | | | | | 155 | | | | | 160 |
| Gly | Leu | Tyr | Asn | Ala | Lys | His | Leu | Leu | Leu | Ala | Gly | Ser | Ser | Ala | Gly |
| | | | | 165 | | | | | 170 | | | | | 175 | |
| Gly | Ile | Gly | Val | Ile | Leu | Asn | Leu | Asp | Arg | Ile | Ser | Thr | Lys | Leu | His |
| | | | 180 | | | | | 185 | | | | | 190 | | |
| Ala | Met | Gly | Phe | Ala | Val | Glu | Val | Arg | Gly | Leu | Ala | Asp | Ser | Gly | Trp |
| | | 195 | | | | | 200 | | | | | 205 | | | |
| Tyr | Leu | Ser | Asp | Arg | Pro | Phe | Glu | Ser | Ser | Cys | Pro | Pro | Gly | Val | Lys |
| | 210 | | | | | 215 | | | | | 220 | | | | |
| Glu | Cys | Gly | Pro | Val | Lys | Thr | Ile | Lys | Glu | Gly | Met | Met | Tyr | Trp | Arg |
| 225 | | | | | 230 | | | | | 235 | | | | | 240 |
| Gly | Ile | Val | Pro | Glu | Asn | Cys | Thr | Lys | Glu | Asn | Leu | Leu | Gln | Pro | Trp |
| | | | | 245 | | | | | 250 | | | | | 255 | |
| Met | Cys | Tyr | Phe | Gly | Glu | Thr | Val | Tyr | Pro | Thr | Ile | Thr | Ala | Pro | Leu |
| | | | 260 | | | | | 265 | | | | | 270 | | |
| Phe | Ile | Phe | Gln | Trp | Leu | Tyr | Asp | Glu | Ala | Gln | Leu | Ala | Leu | Asp | Gly |
| | | 275 | | | | | 280 | | | | | 285 | | | |
| Ser | Ile | Gln | Pro | Arg | Gly | Ile | Gln | Thr | Ile | Asp | Leu | Lys | Gln | Ile | Lys |
| | 290 | | | | | 295 | | | | | 300 | | | | |
| Thr | Ile | Phe | Lys | Ile | Gly | Arg | Lys | Ile | Arg | Glu | Ser | Leu | Lys | Arg | Ala |
| 305 | | | | | 310 | | | | | 315 | | | | | 320 |
| Arg | Val | Arg | His | Val | Phe | Ser | Pro | Ala | Cys | Ile | Ser | His | Thr | Ile | Leu |
| | | | | 325 | | | | | 330 | | | | | 335 | |
| Thr | His | Ser | Ser | Trp | Leu | Asn | Ile | Arg | Leu | Lys | Gly | Ala | Ser | Leu | Asn |
| | | | 340 | | | | | 345 | | | | | 350 | | |
| Asp | Ile | Leu | Thr | Cys | Trp | Tyr | His | Thr | Asp | Gly | His | Glu | Asp | Gly | His |
| | | 355 | | | | | 360 | | | | | 365 | | | |

-continued

```
Gly Lys His Gly His Gly Lys His Gly His Gly Lys His Gly Pro Glu
    370             375             380

Asn Gln His His Trp Ser Thr His Gln Val Asp His Cys Leu Tyr Ile
385             390             395             400

Gln Cys Asn Pro Thr Cys Pro Ile Pro Arg Asn Pro Phe Thr Gly Lys
                405             410             415
```

METHODS FOR IDENTIFYING CANDIDATE MODULATORS OF NOTUM ACTIVITY

RELATED APPLICATIONS

This application claims the benefit of, and priority to, U.S. Provisional Application Ser. No. 61/466,388, filed Mar. 22, 2011, the entire teachings of which are incorporated herein by reference.

GOVERNMENT SUPPORT

This invention was made with government support under NIH R01GM080639 awarded by the National Institutes of Health. The government has certain rights in the invention.

BACKGROUND OF THE INVENTION

Damage to tissues, organs, or other body parts can result from of a wide variety of causes ranging from physical injury to disease or degeneration. The extent to which animals are able to restore normal structure and/or function in response to such events varies considerably across the animal kingdom and can be age- and/or tissue-dependent within a given species. For example, many amphibians are able to fully regrow severed limbs. In contrast, adult humans display minimal capacity to regenerate severed digits, limbs, and most internal organs. Commonly used approaches to the medical and surgical management of damage or loss of body parts in humans include tissue or organ transplantation or grafting and the use of prostheses. However, these approaches have significant limitations. There is a need in the art for compounds that would enhance regeneration, particularly in mammalian species, and for new techniques useful for identifying such compounds.

SUMMARY OF THE INVENTION

The present invention provides compounds, compositions, and methods useful for enhancing regeneration. In one aspect, the invention provides a method of enhancing regeneration in a subject, the method comprising inhibiting NOTUM in the subject. In some embodiments, inhibiting NOTUM in the subject comprises administering a compound that inhibits NOTUM expression or enzymatic activity to the subject. In some embodiments, the compound is administered locally at or near a site of tissue damage. In some embodiments, the method comprises inhibiting the ability of NOTUM to cleave glycophosphatidylinositol (GPI) anchors. In some embodiments, the subject is a vertebrate subject, e.g., a mammalian subject, e.g., a human.

In another aspect, the invention provides a method of upregulating Wnt signaling at a site of tissue damage in a subject, the method comprising inhibiting NOTUM in the subject. In some embodiments, inhibiting NOTUM in the subject comprises administering a compound that inhibits NOTUM expression or enzymatic activity to the subject. In some embodiments, the compound is administered locally at or near a site of tissue damage. In some embodiments, the method comprises inhibiting the ability of NOTUM to cleave GPI anchors. In some embodiments, the method comprises inhibiting the ability of NOTUM to cleave glycophosphatidylinositol (GPI) anchors. In some embodiments, the subject is a vertebrate subject, e.g., a mammalian subject, e.g., a human.

In another aspect, the invention provides a cell comprising a heterologous nucleic acid that encodes a fusion protein comprising: (a) a region comprising a GPI anchor attachment sequence of a vertebrate glypican; and (b) a region comprising a detectable polypeptide. In some embodiments, the vertebrate glypican is a human glypican. In some embodiments, the vertebrate glypican is a vertebrate glypican 3, e.g., a human glypican 3. In some embodiments, the GPI anchor attachment sequence is at the C-terminus of the fusion protein. In some embodiments, the region comprising a GPI anchor attachment sequence of a vertebrate glypican further comprises at least a portion of the remainder of the vertebrate glypican. In some embodiments, the detectable polypeptide comprises a fluorescent polypeptide. In some embodiments, the cell expresses the fusion protein. In some embodiments, the cell contains the proteins necessary for GPI anchor synthesis and attachment. The fusion protein may be processed by the cell so as to cleave the protein and attach a GPI anchor thereto, and the resulting protein attached to the cell membrane. The detectable polypeptide is typically located extracellularly so that cleavage of the GPI anchor (e.g., by NOTUM) releases at least the region comprising the detectable polypeptide from the cell surface. The detectable polypeptide may then be detected in the culture medium.

In another aspect, the invention provides a composition comprising: (a) an isolated NOTUM polypeptide; (b) a reporter molecule comprising a GPI anchor and a detectable moiety; and (c) a test compound. In some embodiments, the NOTUM polypeptide is a vertebrate NOTUM polypeptide, e.g., a human NOTUM polypeptide. In some embodiments, the test compound is a small molecule. In some embodiments, the detectable moiety comprises a detectable polypeptide, e.g., a fluorescent polypeptide. In some embodiments, the GPI anchor is a GPI anchor of a NOTUM substrate polypeptide. In some embodiments, the GPI anchor is a vertebrate glypican GPI anchor. In some embodiments, the GPI anchor is a vertebrate glypican 3 GPI anchor. In some embodiments, the GPI anchor is a human glypican GPI anchor, e.g., human glypican 3 GPI anchor. In some embodiments, the reporter molecule is a fusion protein comprising a GPI anchor of a mature NOTUM substrate polypeptide, at least a portion of a mature NOTUM substrate polypeptide, and a detectable polypeptide. In some embodiments, the composition further comprises a membrane, to which the GPI anchor is attached. In some embodiments, the reporter molecule comprises a fusion protein comprising: (i) a GPI anchor of a human glypican polypeptide; (ii) at least a portion of a human glypican polypeptide; and (iii) a detectable polypeptide. In some embodiments, the reporter molecule comprises: (i) a fusion protein comprising a GPI anchor of a human glypican 3 polypeptide; (ii) at least a portion of a human glypican 3 polypeptide; and (iii) a detectable polypeptide, e.g., a fluorescent polypeptide. In some embodiments, the reporter molecule is a polypeptide, the composition comprises a cell that produces the polypeptide, and at least some of the polypeptide is attached to the cell membrane of the cell via the GPI anchor, so that cleavage of the GPI anchor releases the detectable moiety from the cell.

In another aspect, the invention provides a method of identifying a candidate modulator of NOTUM activity comprising: (i) providing any of the afore-mentioned compositions comprising: (a) an isolated NOTUM polypeptide; (b) a reporter molecule comprising a GPI anchor and a detectable moiety; and (c) a test compound; and (ii) determining whether the test compound affects cleavage of the GPI anchor, wherein increased cleavage of the GPI anchor as compared with the amount of cleavage that would occur in the absence of the compound indicates that the compound enhances NOTUM activity, and decreased cleavage of the GPI anchor as compared with the amount of cleavage that would occur in the absence of the compound indicates that the test compound inhibits NOTUM activity. In some embodiments, the method comprises (i) providing a composition comprising (a) an isolated NOTUM polypeptide; and (b) a reporter molecule comprising a GPI anchor and a detectable moiety; (ii) adding a test compound to the composition of (a); and (iii) determining whether the test compound affects cleavage of the GPI anchor, wherein increased cleavage of the GPI anchor as compared with the amount of cleavage that would occur in the absence of the compound.

In another aspect, the invention provides a method of identifying a candidate modulator of NOTUM activity, the method comprising: (i) providing a composition comprising: (a) an isolated NOTUM polypeptide; (b) a reporter molecule comprising a GPI anchor and a detectable moiety, wherein the reporter molecule is attached to a membrane via the GPI anchor; and (c) a test compound; (ii) maintaining the composition for a suitable time period; and (iii) measuring the amount of detectable moiety released from the surface during the time period, wherein release of a greater amount of detectable moiety than would be expected in the absence of the test compound indicates that the test compound is a candidate enhancer of NOTUM activity, and release of a lower amount of the detectable moiety as compared with the amount that would be expected in the absence of the test compound indicates that the test compound is a candidate inhibitor of NOTUM activity. In various embodiments of the invention the composition can be, e.g., any of the above-mentioned compositions, with the proviso that the reporter molecule is attached to a membrane via the GPI anchor. In some embodiments, the method comprises (A) comparing the amount of detectable moiety released from the membrane during the time period with a reference value; and (B) determining whether the test compound is a candidate enhancer or inhibitor of NOTUM activity based at least in part on the result of step (A). In some embodiments, the membrane is in contact with a liquid medium and step (A) comprises detecting the detectable moiety in the medium.

In some embodiments, a method of identifying a candidate modulator of NOTUM activity further comprises: providing a second composition substantially similar to the first composition but lacking active NOTUM polypeptide; and determining whether the test compound affects the amount of detectable moiety of the second composition released from the membrane, wherein if the test compound affects the amount of detectable moiety released in the composition comprising active NOTUM polypeptide but has little or no effect on the amount of detectable moiety released in the second composition, then the test compound is confirmed as a modulator of NOTUM activity, and if the test compound affects the amount of detectable moiety released in both compositions to approximately the same extent, the test compound is not confirmed as a modulator of NOTUM activity. In some embodiments, the membrane is in contact with a liquid medium and the step of determining comprises detecting the detectable moiety in the medium.

In some embodiments, a method of identifying a candidate modulator of NOTUM further comprises administering a test compound identified as a modulator of NOTUM to a subject.

In another aspect, the invention provides a method of identifying a compound that upregulates Wnt signaling at sites of tissue damage, the method comprising identifying a compound that inhibits NOTUM enzymatic activity. In some embodiments, the method comprises identifying an inhibitor of human NOTUM enzymatic activity.

In another aspect, the invention provides a method of identifying an enhancer of regeneration, the method comprising identifying a compound that inhibits NOTUM enzymatic activity. In some embodiments, the compound is an inhibitor of human NOTUM enzymatic activity. In some embodiments, the method further comprises administering the compound to a subject.

In some embodiments, a method of identifying a compound further comprises administering the compound to a subject. In some embodiments, the subject is a noon-human animal, e.g., a non-human animal that serves as a model for regeneration or wound healing. In some embodiments, the subject is a human.

In another aspect, the invention provides a pharmaceutical composition comprising: (a) an inhibitor of a vertebrate NOTUM; and (b) a pharmaceutically acceptable carrier. In some embodiments, the inhibitor inhibits human NOTUM.

In another aspect, the invention provides an isolated *S. mediterranea* NOTUM protein. In another aspect, the invention provides an isolated nucleic acid encoding *S. mediterranea* NOTUM protein, and its complement.

Certain conventional techniques of cell biology, cell culture, molecular biology, microbiology, recombinant nucleic acid (e.g., DNA) technology, immunology, etc., which are within the skill of the art, may be of use in aspects of the invention. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., editions as of 2008; Sambrook, Russell, and Sambrook, *Molecular Cloning: A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Burns, R., *Immunochemical Protocols* (Methods in Molecular Biology) Humana Press; 3rd ed., 2005, Monoclonal antibodies: a practical approach (P. Shepherd and C Dean, eds., Oxford University Press, 2000); Freshney, R. I., "Culture of Animal Cells, A Manual of Basic Technique", 5th ed., John Wiley & Sons, Hoboken, N J, 2005). All patents, patent applications, websites, databases, scientific articles, and other publications mentioned herein are incorporated herein by reference in their entirety.

BRIEF DESCRIPTION OF THE DRAWING

The patent or application file contains at least one drawing executed in color. Copies of this patent or patent application publication with color drawings will be provided by the Office upon request and payment of the necessary fee.

FIGS. 6A and 6B. (A) Nucleic acid sequence containing complete coding sequence of S. med. notum. Start and stop codons are shown in bold. (B) Amino acid sequence of S. med. NOTUM.

FIGS. 7A and 7B. (A) Nucleic acid sequence containing complete coding sequence of Homo sapiens NOTUM. Start and stop codons are shown in bold. (B) Amino acid sequence of Homo sapiens NOTUM protein.

DETAILED DESCRIPTION OF THE INVENTION

I. Definitions

Figures 1A, 1B, 1C, 1D, 1E, 1F, 1G:
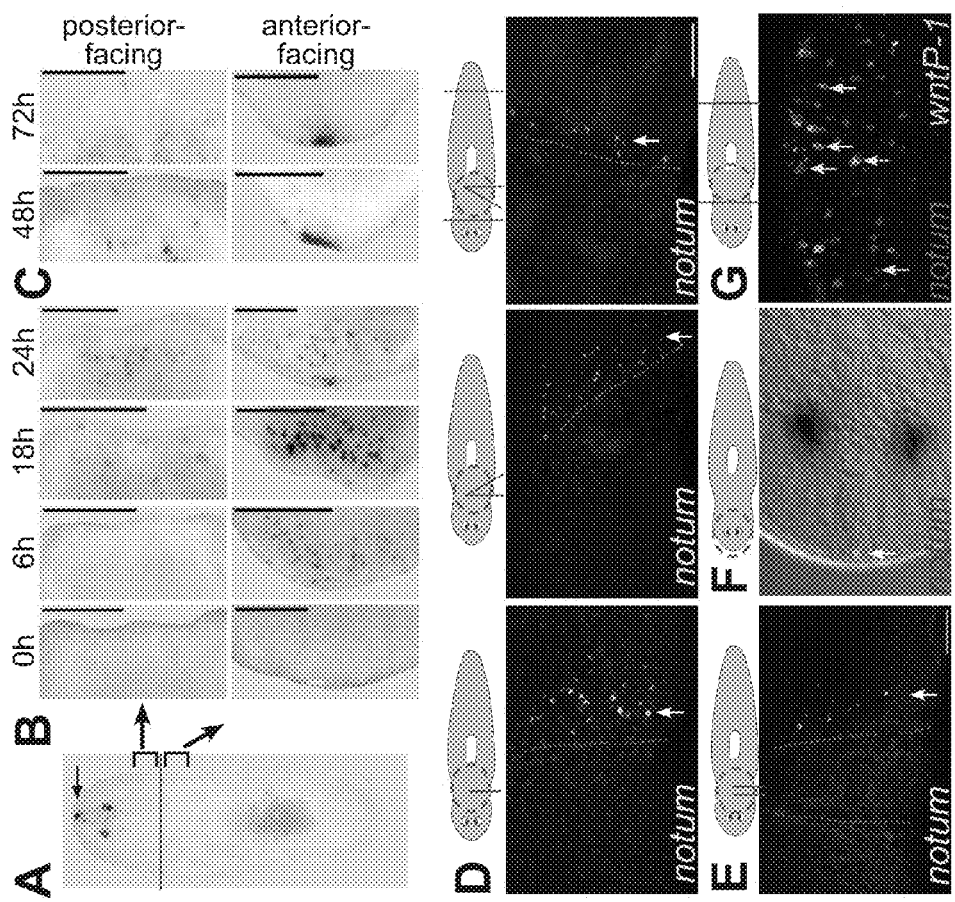
FIGS. 1A, 1B, 1C, 1D, 1E, 1F and 1G demonstrate that notum is expressed at anterior-facing wounds. (A-C) notum in situ hybridizations in intact animals (A) and in regenerating head and trunk fragments (B, C) at time points (h) after amputation. Brackets, magnified regions at anterior- or posterior-facing wounds as indicated. (D, E) Fluorescence in situ hybridizations detecting notum expression 6 hours after incision within the prepharyngeal region (diagrams depict surgeries and regions pictured). (D) Quantitation of notum-expressing cells (n=8 animals examined): region anterior to the two incisions, 0 cells; region between two incisions, 1.6+/−2.4 cells; region posterior to the two incisions, 11.0+/−6.9 cells. (F) notum is expressed in subepidermal cells at the anterior pole of intact animals. (G) Double fluorescence in situ hybridization of notum and wnt1 showing region near an anterior-facing wound 18 hours after amputation. Red dotted line, approximate location of injury. White arrows, notum-expressing cells. Yellow, arrow, cells coexpressing notum and wnt1. Anterior, left (B-F) or top (A, G). Dorsal view (A, 72 h timepoints in panel C, F), or ventral view (all other panels). Images are representatives depicting ≥4 of 5 animals for each panel. Scale bars, 200 microns.

As used herein, the term "antibody" refers to an immunoglobulin, whether natural or wholly or partially synthetically produced. An antibody may be a member of any immunoglobulin class, including any of the mammalian, e.g., human, classes: IgG, IgM, IgA, IgD, and IgE, or subclasses thereof, and may be an antibody fragment, in various embodiments of the invention. As used herein, the term "antibody fragment" refers to a derivative of an antibody which contains less than a complete antibody. In general, an antibody fragment retains at least a significant portion of the full-length antibody's specific binding ability. Examples of antibody fragments include, but are not limited to, Fab, Fab', F(ab')2, scFv, Fv, dsFv diabody, Fd fragments, and domain antibodies. Standard methods of antibody identification and production known in the art can be used to produce an antibody that binds to a polypeptide of interest. In some embodiments, an antibody is a monoclonal antibody. Monoclonal antibodies can be identified and produced, e.g., using hybridoma technology or recombinant nucleic acid technology (e.g., phage or yeast display). In some embodiments, an antibody is a chimeric or humanized antibody. In some embodiments a monoclonal antibody is a fully human antibody. Such antibodies can be identified, e.g., using a transgenic mouse comprising at least some unrearranged human immunoglobulin gene sequences and a disruption of endogenous heavy and light chain murine sequences or using display technology (e.g., phage or yeast display). See, e.g., Lonberg N. Fully human antibodies from transgenic mouse and phage display platforms. *Curr Opin Immunol.* 20(4):450-9, 2008. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may comprise a single chain antibody fragment. Alternatively or additionally, an antibody fragment may comprise multiple chains which are linked together, for example, by disulfide linkages. A functional antibody fragment typically comprises at least about 50 amino acids and more typically comprises at least about 100, e.g., about 200 amino acids. For example, an antibody fragment typically contains at least 1, 2, or 3 complementarity determining domains (CDRs) (VL CDR1, CDR2, CDR3; VH CDR1, CDR2, CDR3) of the antibody, optionally joined by one or more framework region(s). It will be appreciated that certain antibodies, e.g., recombinantly produced antibodies, can comprise heterologous sequences not derived from naturally occurring antibodies. For example, single-chain variable fragments (scFv) are typically fusion protein containing the variable regions of the heavy (VH) and light chains (VL) of immunoglobulins, connected with a short linker peptide of ten to about 25 amino acids. The linker is sometimes rich in glycine (e.g., for flexibility) and/or serine or threonine (e.g., for solubility), and can either connect the N-terminus of the VH with the C-terminus of the VL, or vice versa. Other heterologous sequences such as epitope tags (e.g., to facilitate purification) can be present.

"Isolated" refers to a substance that is (i) separated from at least some other substances with which it is normally found in nature, usually by a process involving the hand of man, (ii) artificially produced (e.g., chemically synthesized), and/or (iii) present in an artificial environment or context (i.e., an environment or context in which it is not normally found in nature).

"Nucleic acid" is used interchangeably with "polynucleotide" and encompasses in various embodiments naturally occurring polymers of nucleosides, such as DNA and RNA, and non-naturally occurring polymers of nucleosides or nucleoside analogs. In some embodiments a nucleic acid comprises standard nucleosides (abbreviated A, G, C, T, U). In other embodiments a nucleic acid comprises one or more non-standard nucleosides. In some embodiments, one or more nucleosides are non-naturally occurring nucleosides or nucleotide analogs. A nucleic acid can comprise modified bases (for example, methylated bases), modified sugars (2'-fluororibose, arabinose, or hexose), modified phosphate groups or other linkages between nucleosides or nucleoside analogs (for example, phosphorothioates or 5'-N-phosphoramidite linkages), locked nucleic acids, or morpholinos. In some embodiments, a nucleic acid comprises nucleosides that are linked by phosphodiester bonds, as in DNA and RNA. In some embodiments, at least some nucleosides are linked by non-phosphodiester bond(s). A nucleic acid can be single-stranded, double-stranded, or partially double-stranded. An at least partially double-stranded nucleic acid can have one or more overhangs, e.g., 5' and/or 3' overhang(s). Nucleic acid modifications (e.g., nucleoside and/or backbone modifications, including use of non-standard nucleosides) known in the art as being useful in the context of RNA interference (RNAi), aptamer, or antisense-based molecules for research or therapeutic purposes are contemplated for use in various embodiments of the instant invention. See, e.g., Crooke, S T (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008. In some embodiments, a modification increases half-life and/or stability of a nucleic acid, e.g., in vivo, relative to RNA or DNA of the same length and strandedness. In some embodiments, a modification decreases immunogenicity of a nucleic acid relative to RNA or DNA of the same length and strandedness. In some embodiments, between 5% and 95% of the nucleosides in one or both strands of a nucleic acid is modified. Modifications may be located uniformly or nonuniformly, and the location of the modifications (e.g., near the middle, near or at the ends, alternating, etc.) can be selected to enhance desired propert(ies). A nucleic acid may comprise a detectable label, e.g., a fluorescent dye, radioactive atom, etc. "Oligonucleotide" refers to a relatively short nucleic acid, e.g., typically between about 4 and about 60 nucleotides long. Where reference is made herein to a polynucleotide, it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

"Polypeptide" refers to a polymer of amino acids. The terms "protein" and "polypeptide" are used interchangeably herein. A peptide is a relatively short polypeptide, typically between about 2 and 60 amino acids in length. Polypeptides used herein typically contain the standard amino acids (i.e., the 20 L-amino acids that are most commonly found in proteins). However, a polypeptide can contain one or more non-standard amino acids (which may be naturally occurring or non-naturally occurring) and/or amino acid analogs known in the art in certain embodiments. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide". Exemplary modifications include glycosylation (e.g., addition of a GPI anchor) and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated. A polypeptide may be cyclic or contain a cyclic portion. Where a naturally occurring polypeptide is discussed herein, it will be understood that the invention encompasses embodiments that relate to any isoform thereof (e.g., different proteins arising from the same gene as a result of alternative splicing or editing of mRNA or as a result of different alleles of a gene, e.g., alleles differing by one or more single nucleotide polymorphisms (typically such alleles will be at least 95%, 96%, 97%, 98%, 99%, or more identical to a reference or concensus sequence). A polypeptide may comprise a sequence that targets it for secretion or to a particular intracellular compartment (e.g., the nucleus) and/or a sequence targets the polypeptide for post-translational modification or degradation. Certain polypeptides may be synthesized as a precursor that undergoes post-translational cleavage or other processing to become a mature polypeptide. In some instances, such cleavage may only occur upon particular activating events. Where relevant, the invention provides embodiments relating to precursor polypeptides and embodiments relating to mature versions of a polypeptide.

A "variant" of a particular polypeptide refers to a polypeptide that differs from such polypeptide (sometimes referred to as the "original polypeptide") by one or more amino acid alterations, e.g., addition(s), deletion(s), and/or substitution(s). Sometimes an original polypeptide is a naturally occurring polypeptide (e.g., from human or non-human animal) or a polypeptide identical thereto. Variants may be naturally occurring or created using, e.g., recombinant DNA techniques or chemical synthesis. An addition can be an insertion within the polypeptide or an addition at the N- or C-terminus. In some embodiments, the number of amino acids substituted, deleted, or added can be for example, about 1 to 30, e.g., about 1 to 20, e.g., about 1 to 10, e.g., about 1 to 5, e.g., 1, 2, 3, 4, or 5. In some embodiments, a variant comprises a polypeptide whose sequence is homologous to the sequence of the original polypeptide over at least 50 amino acids, at least 100 amino acids, at least 150 amino acids, or more, up to the full length of the original polypeptide (but is not identical in sequence to the original polypeptide), e.g., the sequence of the variant polypeptide is at least 50%, 60%, 70%, 75%, 80%, 85%, 90%, 95%, 96%, 97%, 98%, 99%, or more identical to the sequence of the original polypeptide over at least 50 amino acids, at least 100 amino acids, at least 150 amino acids, or more, up to the full length of the original polypeptide. In some embodiments, a variant comprises a polypeptide at least 50%, 60%, 70%, 75%, 80%, 85%, 90%, 91%, 92%, 93%, 94%, 95%, 96%, 97%, 98%, 99%, 99.5% or more identical to an original polypeptide over at least 50%, 60%, 70%, 80%, 85%, 90%, 91%, 92%, 93%, 94%, 95%, 96%, 97%, 98%, 99%, or 100% of the length of the original polypeptide. In some embodiments a variant comprises at least one functional or structural domain, e.g., a domain identified as such in the Conserved Domain Database (CDD) of the National Center for Biotechnology Information (e.g., on its website), e.g., an NCBI-curated domain.

In some embodiments one, more than one, or all biological functions or activities of a variant or fragment is substantially similar to that of the corresponding biological function or activity of the original molecule. In some embodiments, a functional variant retains at least 10%, 20%, 30%, 40%, 50%, 60%, 70%, 80%, 90%, 95%, 96%, 97%, 98%, 99%, or more of the activity of the original polypeptide, e.g., about equal activity. In some embodiments, the activity of a variant is up to approximately 100%, approximately 125%, or approximately 150% of the activity of the original molecule. In other nonlimiting embodiments an activity of a variant or fragment is considered substantially similar to the activity of the original molecule if the amount or concentration of the variant needed to produce a particular effect is within 0.5 to 5-fold of the amount or concentration of the original molecule needed to produce that effect.

In some embodiments amino acid "substitutions" in a variant are the result of replacing one amino acid with another amino acid having similar structural and/or chemical properties, i.e., conservative amino acid replacements. "Conservative" amino acid substitutions may be made on the basis of similarity in any of a variety or properties such as side chain size, polarity, charge, solubility, hydrophobicity, hydrophilicity, and/or amphipathicity of the residues involved. For example, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Within a particular group, certain substitutions may be of particular interest, e.g., replacements of leucine by isoleucine (or vice versa), serine by threonine (or vice versa), or alanine by glycine (or vice versa). Of course non-conservative substitutions are often compatible with retaining function as well. In some embodiments, a substitution or deletion does not alter or delete an amino acid important for activity. Insertions or deletions may range in size from about 1 to 20 amino acids, e.g., 1 to 10 amino acids. In some instances larger domains may be removed without substantially affecting function. In certain embodiments of the invention the sequence of a variant can be obtained by making no more than a total of 5, 10, 15, or 20 amino acid additions, deletions, or substitutions to the sequence of a naturally occurring enzyme. In some embodiments no more than 1%, 5%, 10%, or 20% of the amino acids in a polypeptide are insertions, deletions, or substitutions relative to the original polypeptide. Guidance in determining which amino acid residues may be replaced, added, or deleted without eliminating or substantially reducing activities of interest, may be obtained by comparing the sequence of the particular polypeptide with that of homologous polypeptides (e.g., from other organisms) and minimizing the number of amino acid sequence changes made in regions of high homology (conserved regions) or by replacing amino acids with those found in homologous sequences since amino acid residues that are conserved among various species are more likely to be important for activity than amino acids that are not conserved.

In some embodiments, a variant of a polypeptide comprises a heterologous polypeptide portion. The heterologous portion often has a sequence that is not present in or homologous to the original polypeptide. A heterologous portion may be, e.g., between 5 and about 5,000 amino acids long, or longer. Often it is between 5 and about 1,000 amino acids long. In some embodiments, a heterologous portion comprises a sequence that is found in a different polypeptide, e.g., a functional domain. In some embodiments, a heterologous portion comprises a sequence useful for purifying, expressing, solubilizing, and/or detecting the polypeptide. In some embodiments, a heterologous portion comprises a polypeptide "tag", e.g., an affinity tag or epitope tag. For example, the tag can be an affinity tag (e.g., HA, TAP, Myc, 6×His, Flag, GST), fluorescent or luminescent protein (e.g., EGFP, ECFP, EYFP, Cerulean, DsRed, mCherry), solubility-enhancing tag (e.g., a SUMO tag, NUS A tag, SNUT tag, or a monomeric mutant of the Ocr protein of bacteriophage T7). See, e.g., Esposito D and Chatterjee D K. Curr Opin Biotechnol.; 17(4): 353-8 (2006). In some embodiments, a tag can serve multiple functions. A tag is often relatively small, e.g., ranging from a few amino acids up to about 100 amino acids long. In some embodiments a tag is more than 100 amino acids long, e.g., up to about 500 amino acids long, or more. In some embodiments, a polypeptide has a tag located at the N- or C-terminus, e.g., as an N- or C-terminal fusion. The polypeptide could comprise multiple tags. In some embodiments, a 6×His tag and a NUS tag are present, e.g., at the N-terminus. In some embodiments, a tag is cleavable, so that it can be removed from the polypeptide, e.g., by a protease. In some embodiments, this is achieved by including a sequence encoding a protease cleavage site between the sequence encoding the portion homologous to the original polypeptide and the tag. Exemplary proteases include, e.g., thrombin, TEV protease, Factor Xa, PreScission protease, etc. In some embodiments, a "self-cleaving" tag is used. See, e.g., PCT/US05/05763. Sequences encoding a tag can be located 5' or 3' with respect to a polynucleotide encoding the polypeptide (or both). In some embodiments a tag or other heterologous sequence is separated from the rest of the polypeptide by a polypeptide linker. For example, a linker can be a short polypeptide (e.g., 15-25 amino acids). Often a linker is composed of small amino acid residues such as serine, glycine, and/or alanine. A heterologous domain could comprise a transmembrane domain, a secretion signal domain, etc.

In certain embodiments of the invention a fragment or variant, optionally excluding a heterologous portion, if present, possesses sufficient structural similarity to the original polypeptide so that when its 3-dimensional structure (either actual or predicted structure) is superimposed on the structure of the original polypeptide, the volume of overlap is at least 70%, preferably at least 80%, more preferably at least 90% of the total volume of the structure of the original polypeptide. A partial or complete 3-dimensional structure of the fragment or variant may be determined by crystallizing the protein, which can be done using standard methods. Alternately, an NMR solution structure can be generated, also using standard methods. A modeling program such as MODELER (Sali, A. and Blundell, T L, J. Mol. Biol., 234, 779-815, 1993), or any other modeling program, can be used to generate a predicted structure. If a structure or predicted structure of a related polypeptide is available, the model can be based on that structure. The PROSPECT-PSPP suite of programs can be used (Guo, J T, et al., Nucleic Acids Res. 32 (Web Server issue):W522-5, Jul. 1, 2004). Where embodiments of the invention relate to variants of a polypeptide, it will be understood that polynucleotides encoding the variant are provided.

"Purified" refers to agents or entities (e.g., compounds) that have been separated from most of the components with which they are associated in nature or when originally generated. In general, such purification involves action of the hand of man. Purified agents or entities may be partially purified, substantially purified, or pure. Such agents or entities may be, for example, at least 50%, 60%, 70%, 75%, 80%, 85%, 90%, 95%, 96%, 97%, 98%, 99%, or more than 99% pure. In some embodiments, a nucleic acid or polypeptide is purified such that it constitutes at least 75%, 80%, 855%, 90%, 95%, 96%, 97%, 98%, 99%, or more, of the total nucleic acid or polypeptide material, respectively, present in a preparation. Purity can be based on, e.g., dry weight, size of peaks on a chromatography tracing, molecular abundance, intensity of bands on a gel, or intensity of any signal that correlates with molecular abundance, or any art-accepted quantification method. In some embodiments, water, buffers, ions, and/or small molecules (e.g., precursors such as nucleotides or amino acids), can optionally be present in a purified preparation. A purified molecule may be prepared by separating it from other substances (e.g., other cellular materials), or by producing it in such a manner to achieve a desired degree of purity. In some embodiments, a purified molecule or composition refers to a molecule or composition that is prepared using any art-accepted method of purification. In some embodiments "partially purified" means that a molecule produced by a cell is no longer present within the cell, e.g., the cell has been lysed and, optionally, at least some of the cellular material (e.g., cell wall, cell membrane(s), cell organelle(s)) has been removed.

"Regeneration" generally refers to the at least partial replacement, restoration, or regrowth of a tissue, organ, or other body structure, or portion thereof, following loss, damage, or degeneration, or as a homeostatic process. Examples of regeneration include regrowth of severed digits or limbs, replacement of bone, cartilage, skin, or muscle that has been lost due to injury or disease, and the increase in size and cell number of a portion of an organ that may take place to compensate for loss or damage of other portions. Regeneration can occur via a variety of different mechanisms such as, for example, the rearrangement of pre-existing cells and/or tissue (e.g., through cell migration), the division of adult somatic stem cells or other progenitor cells and differentiation of at least some of their descendants, and/or the dedifferentiation, transdifferentiation, and/or proliferation of cells. Some types of regeneration, such as limb and tail regeneration in certain amphibians and fin regeneration in fish, involve formation of a population of proliferative cells referred to as a blastema that ultimately gives rise to the regenerated structure. More than one type of regenerative process can operate in regeneration of a given tissue and/or within different tissues of the same animal. In some aspects, regeneration may be distinguished from repair, in that repair may refer to the physiologic adaptation of a tissue after injury in an effort to re-establish continuity without regards to exact replacement of lost/damaged tissue, while in some aspects, regeneration refers to the at least partial replacement of lost/damaged tissue with tissue that resembles, e.g., closely resembles or essentially precisely copies the tissue as it existed before the damage occurred, such that both morphology and functionality are restored. In such aspects, regeneration may be considered a form of repair that results in a particularly favorable outcome for a subject in terms of restoring form and function following tissue damage.

"RNA interference" (RNAi) is used herein consistently with its meaning in the art to refer to a phenomenon whereby double-stranded RNA (dsRNA) triggers the sequence-specific degradation or translational repression of a corresponding mRNA having complementarity to a strand of the dsRNA. It will be appreciated that the complementarity between the strand of the dsRNA and the mRNA need not be 100% but need only be sufficient to mediate inhibition of gene expression (also referred to as "silencing" or "knockdown"). For example, the degree of complementarity is such that the strand can either (i) guide cleavage of the mRNA in the RNA-induced silencing complex (RISC); or (ii) cause translational repression of the mRNA. In certain embodiments the double-stranded portion of the RNA is less than about 30 nucleotides in length, e.g., between 17 and 29 nucleotides in length. In certain embodiments a first strand of the dsRNA is at least 80%, 85%, 90%, 95%, or 100% complementary to a target mRNA and the other strand of the dsRNA is at least 80%, 85%, 90%, 95%, or 100% complementary to the first strand. In mammalian cells, RNAi may be achieved by introducing an appropriate double-stranded nucleic acid into the cells or expressing a nucleic acid in cells that is then processed intracellularly to yield dsRNA therein. Nucleic acids capable of mediating RNAi are referred to herein as "RNAi agents". Exemplary nucleic acids capable of mediating RNAi are a short hairpin RNA (shRNA), a short interfering RNA (siRNA), and a microRNA precursor. These terms are well known and are used herein consistently with their meaning in the art. siRNAs typically comprise two separate nucleic acid strands that are hybridized to each other to form a duplex. They can be synthesized in vitro, e.g., using standard nucleic acid synthesis techniques. siRNAs are typically double-stranded oligonucleotides having 16-30, e.g., 16, 17, 18, 19, 20, 21, 22, 23, 24, 25, 26, 27, 28, 29, or 30 nucleotides (nt) in each strand, wherein the double-stranded oligonucleotide comprises a double-stranded portion between 15 and 29 nucleotides long and either or both of the strands may comprise a 3' overhang between, e.g., 1-5 nucleotides long, or either or both ends can be blunt. In some embodiments, an siRNA comprises strands between 19 and 25 nt, e.g., between 21 and 23 nucleotides long, wherein one or both strands comprises a 3' overhang of 1-2 nucleotides. One strand of the double-stranded portion of the siRNA (termed the "guide strand" or "antisense strand") is substantially complementary (e.g., at least 80% or more, e.g., 85%, 90%, 95%, or 100%) complementary to (e.g., having 3, 2, 1, or 0 mismatched nucleotide(s)) a target region in the mRNA, and the other double-stranded portion is substantially complementary to the first double-stranded portion. In many embodiments, the guide strand is 100% complementary to a target region in an mRNA and the other passenger strand is 100% complementary to the first double-stranded portion (it is understood that, in various embodiments, the 3' overhang portion of the guide strand, if present, may or may not be complementary to the mRNA when the guide strand is hybridized to the mRNA). In some embodiments, a shRNA molecule is a nucleic acid molecule comprising a stem-loop, wherein the double-stranded stem is 16-30 nucleotides long and the loop is about 1-10 nucleotides long. siRNA can comprise a wide variety of modified nucleosides, nucleoside analogs and can comprise chemically or biologically modified bases, modified backbones, etc. Without limitation, any modification recognized in the art as being useful for RNAi can be used. Some modifications result in increased stability, cell uptake, potency, etc. Some modifications result in decreased immunogenicity or clearance. In certain embodiments the siRNA comprises a duplex about 19-23 (e.g., 19, 20, 21, 22, or 23) nucleotides in length and, optionally, one or two 3' overhangs of 1-5 nucleotides in length, which may be composed of deoxyribonucleotides. shRNA comprise a single nucleic acid strand that contains two complementary portions separated by a predominantly non-selfcomplementary region. The complementary portions hybridize to form a duplex structure and the non-selfcomplementary region forms a loop connecting the 3' end of one strand of the duplex and the 5' end of the other strand. shRNAs undergo intracellular processing to generate siRNAs. Typically, the loop is between 1 and 8, e.g., 2-6 nucleotides long.

MicroRNAs (miRNAs) are small, naturally occurring, non-coding, single-stranded RNAs of about 21-25 nucleotides (in mammalian systems) that inhibit gene expression in a sequence-specific manner. They are generated intracellularly from precursors (pre-miRNA) having a characteristic secondary structure comprised of a short hairpin (about 70 nucleotides in length) containing a duplex that often includes one or more regions of imperfect complementarity which is in turn generated from a larger precursor (pri-miRNA). Naturally occurring miRNAs are typically only partially complementary to their target mRNA and often act via translational repression. RNAi agents modelled on endogenous miRNA or miRNA precursors are of use in certain embodiments of the invention. For example, an siRNA can be designed so that one strand hybridizes to a target mRNA with one or more mismatches or bulges mimicking the duplex formed by a miRNA and its target mRNA. Such siRNA may be referred to as miRNA mimics or miRNA-like molecules. miRNA mimics may be encoded by precursor nucleic acids whose structure mimics that of naturally occurring miRNA precursors.

In certain embodiments an RNAi agent is a vector (e.g., a plasmid or virus) that comprises a template for transcription of an siRNA (e.g., as two separate strands that can hybridize to each other), shRNA, or microRNA precursor. Typically the template encoding the siRNA, shRNA, or miRNA precursor is operably linked to expression control sequences (e.g., a promoter), as known in the art. Such vectors can be used to introduce the template into vertebrate cells, e.g., mammalian cells, and result in transient or stable expression of the siRNA, shRNA, or miRNA precursor. Precurors (shRNA or miRNA precursors) are processed intracellularly to generate siRNA or miRNA.

In general, small RNAi agents such as siRNA can be chemically synthesized or can be transcribed in vitro or in vivo from a DNA template either as two separate strands that then hybridize, or as an shRNA which is then processed to generate an siRNA. Often RNAi agents, especially those comprising modifications, are chemically synthesized. Chemical synthesis methods for oligonucleotides are well known in the art.

A "small molecule" as used herein, is an organic molecule that is less than about 2 kilodaltons (KDa) in mass. In some embodiments, the small molecule is less than about 1.5 KDa, or less than about 1 KDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups. In some embodiments, a small molecule is non-polymeric. In some embodiments, a small molecule is not an amino acid. In some embodiments, a small molecule is not a nucleotide. In some embodiments, a small molecule is not a saccharide.

A "subject" can be any multicellular animal. Often a subject is a vertebrate, e.g., a mammal or avian. Exemplary mammals include, e.g., humans, non-human primates, rodents (e.g., mouse, rat, rabbit), ungulates (e.g., ovine, bovine, equine, caprine species), canines, and felines. Often, a subject is an individual to whom a compound is to be delivered, e.g., for experimental, diagnostic, and/or therapeutic purposes or from whom a sample is obtained or on whom a diagnostic procedure is performed (e.g., a sample or procedure that will be used to assess tissue damage and/or to assess the effect of a compound of the invention).

"Tissue damage" is used herein to refer to any type of damage or injury to cells, tissues, organs, or other body structures. The term encompasses, in various embodiments, degeneration due to disease, damage due to physical trauma or surgery, damage caused by exposure to deleterious substance, and other disruptions in the structure and/or functionality of cells, tissues, organs, or other body structures.

"Treat", "treating" and similar terms in regard to a subject refer to providing medical and/or surgical management of the subject. Treatment can include, but is not limited to, administering a compound or composition (e.g., a pharmaceutical composition) to a subject. Treatment of a subject according to the instant invention is typically undertaken in an effort to promote regeneration, e.g., in a subject who has suffered tissue damage or is expected to suffer tissue damage (e.g., a subject who will undergo surgery). The effect of treatment can generally include increased regeneration, reduced scarring, and/or improved structural or functional outcome following tissue damage (as compared with the outcome in the absence of treatment), and/or can include reversal or reduction in severity or progression of a degenerative disease.

"Vector" is used herein to refer to a nucleic acid or a virus or portion thereof (e.g., a viral capsid or genome) capable of mediating entry of, e.g., transferring, transporting, etc., a nucleic acid molecule into a cell. Where the vector is a nucleic acid, the nucleic acid molecule to be transferred is generally linked to, e.g., inserted into, the vector nucleic acid molecule. A nucleic acid vector may include sequences that direct autonomous replication (e.g., an origin of replication), or may include sequences sufficient to allow integration of part or all of the nucleic acid into host cell DNA. Useful nucleic acid vectors include, for example, DNA or RNA plasmids, cosmids, and naturally occurring or modified viral genomes or portions thereof or nucleic acids (DNA or RNA) that can be packaged into viral) capsids. Plasmid vectors typically include an origin of replication and one or more selectable markers. Plasmids may include part or all of a viral genome (e.g., a viral promoter, enhancer, processing or packaging signals, etc.). Viruses or portions thereof that can be used to introduce nucleic acid molecules into cells are referred to as viral vectors. Useful viral vectors include adenoviruses, adeno-associated viruses, retroviruses, lentiviruses, vaccinia virus and other poxviruses, herpesviruses (e.g., herpes simplex virus), and others. Viral vectors may or may not contain sufficient viral genetic information for production of infectious virus when introduced into host cells, i.e., viral vectors may be replication-defective, and such replication-defective viral vectors may be preferable for therapeutic use. Where sufficient information is lacking it may, but need not be, supplied by a host cell or by another vector introduced into the cell. The nucleic acid to be transferred may be incorporated into a naturally occurring or modified viral genome or a portion thereof or may be present within the virus or viral capsid as a separate nucleic acid molecule. It will be appreciated that certain plasmid vectors that include part or all of a viral genome, typically including viral genetic information sufficient to direct transcription of a nucleic acid that can be packaged into a viral capsid and/or sufficient to give rise to a nucleic acid that can be integrated into the host cell genome and/or to give rise to infectious virus, are also sometimes referred to in the art as viral vectors. Vectors may contain one or more nucleic acids encoding a marker suitable for use in the identifying and/or selecting cells that have or have not been transformed or transfected with the vector. Markers include, for example, proteins that increase or decrease either resistance or sensitivity to antibiotics (e.g., an antibiotic-resistance gene encoding a protein that confers resistance to an antibiotic such as puromycin, hygromycin or blasticidin) or other compounds, enzymes whose activities are detectable by assays known in the art (e.g., β-galactosidase or alkaline phosphatase), and proteins or RNAs that detectably affect the phenotype of transformed or transfected cells (e.g., fluorescent proteins). Expression vectors are vectors that include regulatory sequence(s), e.g., expression control sequences such as a promoter, sufficient to direct transcription of an operably linked nucleic acid. Regulatory sequences may also include enhancer sequences or upstream activator sequences. Vectors may optionally include 5' leader or signal sequences. Vectors may optionally include cleavage and/or polyadenylations signals and/or a 3' untranslated regions. Vectors often include one or more appropriately positioned sites for restriction enzymes, to facilitate introduction into the vector of the nucleic acid to be expressed. An expression vector comprises sufficient cis-acting elements for expression; other elements required or helpful for expression can be supplied by the host cell or in vitro expression system.

Various techniques may be employed for introducing nucleic acid molecules into cells. Such techniques include chemical-facilitated transfection using compounds such as calcium phosphate, cationic lipids, cationic polymers, liposome-mediated transfection, non-chemical methods such as electroporation, particle bombardment, or microinjection, and infection with a virus that contains the nucleic acid molecule of interest (sometimes termed "transduction"). Markers can be used for the identification and/or selection of cells that have taken up the vector and, typically, express the nucleic acid. Cells can be cultured in appropriate media to select such cells and, optionally, establish a stable cell line.

II. NOTUM Modulation and NOTUM Modulators

The present invention provides NOTUM modulators (e.g., NOTUM inhibitors) and methods of use thereof. The invention further provides compositions and methods useful for identifying modulators (e.g., inhibitors) of NOTUM. In some aspects, the invention provides methods of enhancing regeneration comprising administering an inhibitor of NOTUM ("NOTUM inhibitor") to a multicellular organism in need thereof.

NOTUM, the protein product of the NOTUM gene, is a hydrolase and is highly conserved in animals ranging from sea anemones to mammals. NOTUM protein sequences, and sequences of nucleic acids (e.g., mRNA) encoding NOTUM, from a number of different animals are known in the art and can be found, e.g., in publicly available databases such as those available at the National Center for Biotechnology Information (NCBI) (e.g., on its website), e.g., Reference Sequence (RefSeq) collections (e.g., of proteins, transcripts, and genomic DNA) and the Gene database. The human NOTUM protein has been assigned RefSeq accession number NP_848588, and the mouse protein has been assigned accession number RefSeq accession number NP_780472.

Figure 8:
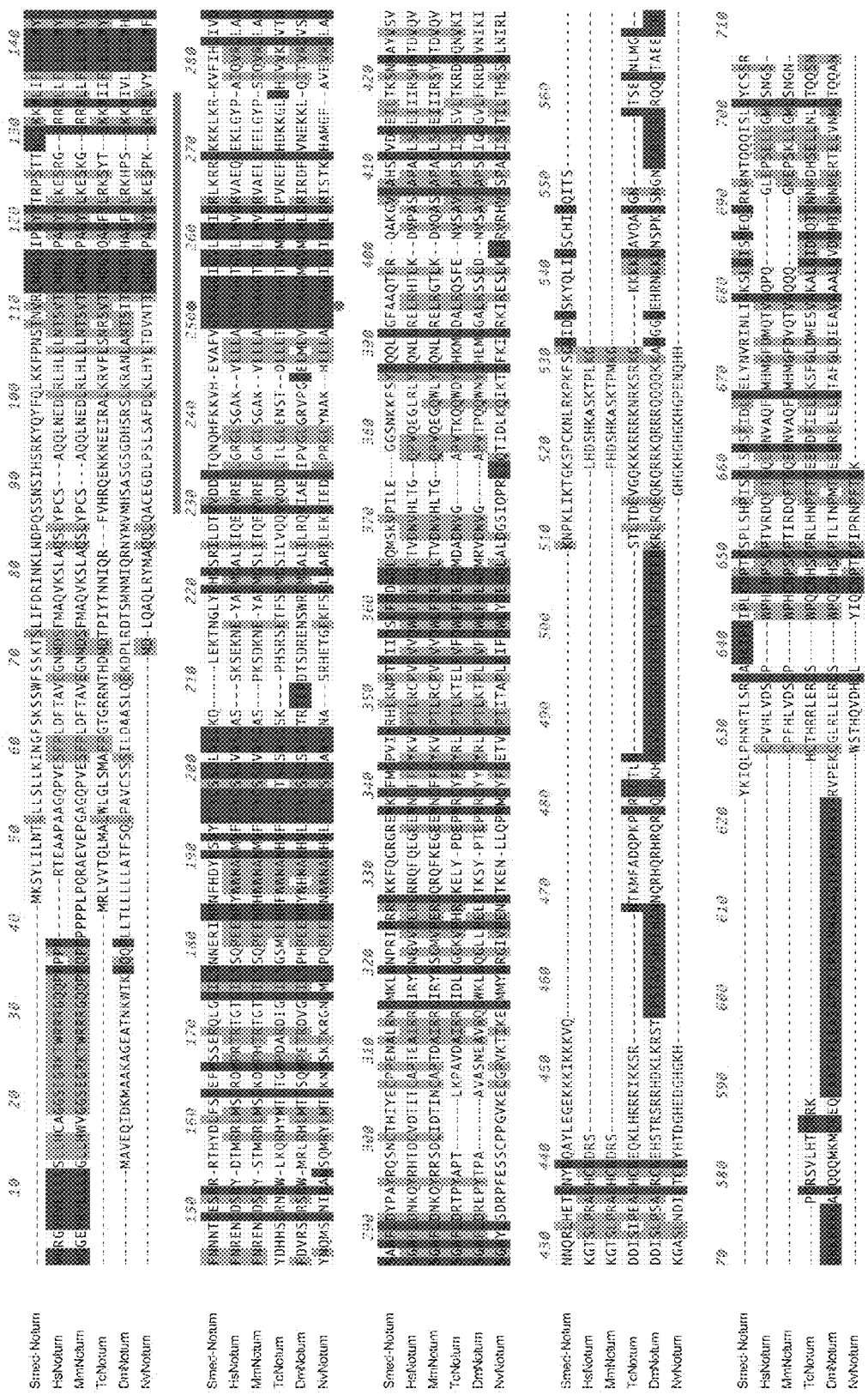
FIG. 8 demonstrates alignment of NOTUM proteins. Alignment of S. med. NOTUM with NOTUM proteins from other species (Hs, homo sapiens; Mm, Mus musculus; Tc, Tribolium castaneum; Dm, Drosophila melanogaster; Nv, Nematostella vectensis). Blue bar marks hydrolase homology domain. Green dot marks a serine proposed to function in catalysis (12).

Applicants identified a homolog of the *Drosophila* and mammalian NOTUM genes in the planarian *S. mediterannea* and named it Smed-notum (FIG. 8). Planarians are flatworms with the ability to regenerate any missing part of their bodies. When normal planarians are transected, anterior-facing wounds regenerate a head, and posterior-facing wounds regenerate a tail. For example, an animal fragment generated by amputation of the head and tail regenerates a head from the anterior end (i.e., at the site of an anterior-facing wound) and a tail from the posterior end (i.e., at the site of a posterior-facing wound). This property is known as "regeneration polarity":

Applicants examined the role of Smed-notum in regeneration and showed that the notum gene becomes expressed early in planarian regeneration, strongly near anterior-facing wounds, and weakly near posterior-facing wounds. Expression of a member of the Wnt family of signaling molecules is induced at wounds in planarians, and Wnt signaling at wound sites is required for normal planarian regeneration, e.g., for the head-versus-tail regeneration decision. Wnts are an evolutionarily conserved family of secreted glycoproteins that activate downstream signal transduction through a process that involves interaction with Frizzled (Fz) family cell surface receptors. In the canonical Wnt signaling pathway, this interaction leads to inhibition of β-catenin phosphorylation, thereby inhibiting destruction of β-catenin by the Axin-Adenomatous Polyposis Coli (APC)-GSK-3β complex, thus leading to the accumulation of β-catenin in the cytoplasm. β-catenin translocates to the nucleus and forms a complex with T-cell factor/lymphoid enhancer factor (TCF/LEF), which directs expression of target genes. Wnt signaling plays an important role in regeneration in a wide variety of organisms (24-28). Applicants showed that upregulation of Smed-notum depended on Wnt activity, as the upregulation was largely abolished by inhibiting β-catenin. Inhibition of Smed-notum using RNAi resulted in a phenotype essentially the same as that caused by inhibiting expression of APC, which encodes an intracellular inhibitor of β-catenin. Thus, Wnt signaling through β-catenin causes expression of notum, which in turn attenuates Wnt signaling, thereby establishing that Smed-notum is a feedback inhibitor of Wnt signaling in planarian regeneration.

The invention encompasses the recognition of the role of NOTUM as an inhibitor of Wnt signaling in the context of regeneration. The invention provides a method of enhancing regeneration in a subject in need thereof comprising inhibiting NOTUM in the subject. In some embodiments, inhibiting NOTUM in a subject comprises administering a NOTUM inhibitor to the subject. In accordance certain aspects of the invention, inhibiting NOTUM inhibits feedback inhibition of Wnt signaling by NOTUM and thereby causes upregulation of Wnt signaling at cell types and sites at which Wnt signaling is active. In some embodiments, NOTUM inhibition disrupts a negative feedback loop that would otherwise act to limit Wnt signaling specifically in cell types and/or at sites in which Wnt signaling is active. In certain embodiments of the invention, NOTUM inhibition enhances regeneration of tissues or organs in which one or more Wnt protein(s) and/or Wnt receptor(s) is expressed. Without wishing to be bound by any theory, NOTUM inhibitors could possess a specificity that is unique and distinct from that of various other Wnt signaling agonists. Such specificity may be of particular value for purposes of enhancing regeneration. For example, NOTUM inhibitors may be of use to specifically disinhibit Wnt signaling at sites of wounds or other damage, e.g., sites at which endogenous Wnt and/or NOTUM expression is induced, while having less effect or no significant effect on Wnt signaling in tissues that have not been wounded or damaged. In some aspects of the invention, administration of a NOTUM inhibitor allows increased Wnt signaling to occur at sites of wounds or other tissue damage, thereby promoting regeneration at such locations. In some embodiments of the invention, significant effects of NOTUM inhibition on Wnt signaling are largely or entirely restricted to locations where regeneration is beneficial. In some aspects, NOTUM inhibition provides means of selectively enhancing Wnt signaling at locations where such signaling is useful to promote regeneration.

The invention provides a number of different methods of inhibiting NOTUM and a variety of different compounds useful for inhibiting NOTUM. In general, a NOTUM inhibitor can be, e.g., a small molecule, nucleic acid, oligonucleotide, polypeptide, peptide, lipid, carbohydrate, etc. In some embodiments of the invention, NOTUM is inhibited by decreasing the amount of NOTUM produced by cells and/or by decreasing the level of activity of NOTUM. The amount of NOTUM can be decreased by inhibiting synthesis of NOTUM by cells (also referred to as "inhibiting NOTUM expression"), e.g., by reducing the amount of mRNA encoding NOTUM or by reducing translation of mRNA encoding NOTUM.

In some embodiments of the invention, NOTUM expression is inhibited by RNA interference (RNAi). As known in the art, RNAi is a process in which the presence in a cell of double-stranded RNA that has sequence correspondence to a gene leads to sequence-specific inhibition of the expression of the gene, typically as a result of cleavage or translational repression of the mRNA transcribed from the gene. Compounds useful for causing inhibition of expression by RNAi ("RNAi agents") include short interfering RNAs (siRNAs), short hairpin RNAs (shRNAs), microRNAs (miRNAs), and miRNA-like molecules.

Exemplary sequences of siRNAs that inhibit planarian NOTUM expression are provided in the Examples. One of skill in the art can readily design sequences for RNAi agents, e.g., siRNAs, useful for inhibiting expression of mammalian NOTUM, e.g., human NOTUM. In some embodiments, such sequences are selected to minimize "off-target" effects. For example, a sequence that is complementary to a sequence present in NOTUM mRNA and not present in other mRNAs expressed in a species of interest (or not present in the genome of the species of interest) may be used. Position-specific chemical modifications may be used to reduce potential off-target effects. In some embodiments, at least two different RNAi agents, e.g., siRNAs, targeted to NOTUM mRNA are used in combination. In some embodiments, a microRNA (which may be an artificially designed microRNA) is used to inhibit NOTUM expression.

In some embodiments of the invention, NOTUM expression is inhibited using an antisense molecule comprising a single-stranded oligonucleotide that is perfectly or substantially complementary to mRNA encoding NOTUM. The oligonucleotide hybridizes to NOTUM mRNA leading, e.g., to degradation of the mRNA by RNase H or blocking of translation by steric hindrance. In other embodiments of the invention, NOTUM expression is inhibited using a ribozyme or triplex nucleic acid.

In some embodiments, of the invention, a NOTUM inhibitor inhibits at least one activity of NOTUM. NOTUM activity can be decreased by contacting NOTUM with a compound that physically interacts with NOTUM. Such a compound may, for example, alter the structure of NOTUM (e.g., by covalently modifying it) and/or block the interaction of NOTUM with one or more other molecule(s) such as NOTUM substrates. NOTUM releases a variety of glycosylphosphatidylinositol (GPI)-anchored proteins from the cell surface (13). In some embodiments of the invention, a NOTUM inhibitor inhibits the ability of NOTUM to release one or more GPI-anchored protein(s) from the cell surface. In some embodiments of the invention, a NOTUM inhibitor inhibits the ability of NOTUM to cleave (i.e., catalyze cleavage of) a GPI anchor. As used herein, "inhibit" or "reduce" may, or may not, be complete. For example, release of a GPI-anchored protein or cleavage of a GPI anchor may, or may not, be decreased to a state of complete cessation of release or cleavage for an effect to be considered one of inhibition or reduction. In some embodiments, inhibition or reduction may be a decrease of at least about 5%, 10%, 15%, 20%, 25%, 30%, 35%, 40%, 45%, 50%, 55%, 60%, 65%, 70%, 75%, 80%, 85%, 90%, 95%, or 99% of a reference level (e.g., a control level). A control level may be the level of release or cleavage that occurs in the absence of the inhibitor. For example, an inhibitor may reduce the level of cleavage or release to no more than 95%, 90%, 85%, 80%, 75%, 70%, 65%, 60%, 55%, 50%, 40%, 30%, 25%, 20%, 10%, or 5% of the level that occurs in the absence of the inhibitor under the conditions tested. In some embodiments, release or cleavage is reduced to 75% or less of the level that occurs in the absence of the inhibitor, under the conditions tested. In some embodiments, release or cleavage is reduced to 50% or less of the level that occurs in the absence of the inhibitor, under the conditions tested. In some embodiments, release or cleavage is reduced to 25% or less of the level that occurs in the absence of the inhibitor, under the conditions tested. In some embodiments, release or cleavage is reduced to 10% or less of the level that occurs in the absence of the inhibitor, under the conditions tested. In some cases the level of modulation (e.g., inhibition or reduction) as compared with a control level is statistically significant. As used herein, "statistically significant" refers to a p-value of less than 0.05, e.g., a p-value of less than 0.025 or a p-value of less than 0.01, using an appropriate statistical test (e.g, ANOVA, t-test, etc.).

The GPI anchor is a glycolipid structure that is added posttranslationally to the C-terminus of certain eukaryotic proteins and tethers such proteins to the outer leaflet of the cell membrane. GPI anchors are found in a variety of structurally and functionally diverse proteins diverse proteins from a variety of eukaryotes (mammalian, plant, yeast, and protozoan). In general, GPI anchors contain a phosphoethanolamine linker (attached to the anchored protein), a glycan core, and a phospholipid tail. The glycan core contains phosphoinositol, glucosamine, and mannose residues, which are frequently modified with various side chains such as phosphoethanolamine, mannose, galactose, sialic acid, or other sugars (Sharom F J & Lehto M T, Glycosylphosphatidylinositol-anchored proteins: structure, function, and cleavage by phosphatidylinositol-specific phospholipase C. *Biochem Cell Biol.*, 80(5):535-49 (2002); Paulick M G & Bertozzi C R, The glycosylphosphatidylinositol anchor: a complex membrane-anchoring structure for proteins. *Biochemistry.* 47(27):6991-7000 (2008)). Proteins destined to receive a GPI anchor have an N-terminal signal peptide (also called "signal sequence") for translocation into the lumen of the endoplasmic reticulum (ER) and a C-terminal signal sequence often referred to as a "GPI anchor attachment sequence" that directs attachment of the GPI anchor. The GPI anchor attachment signal is cleaved during protein processing in the endoplasmic reticulum. The preassembled GPI core structure is covalently attached to the new C-terminus of the target protein by a transamidase enzyme (GPI transamidase (GPIT), a multisubunit, endoplasmic reticulum (ER)-localized enzyme) and serves to anchor the protein to the plasma membrane at the cell surface. (See, e.g., Vainauskas S, and Menon A K. J Biol Chem. Ethanolamine phosphate linked to the first mannose residue of glycosylphosphatidylinositol (GPI) lipids is a major feature of the GPI structure that is recognized by human GPI transamidase, 281(50):38358-64 (2006)); Maeda Y, et al., CHO glycosylation mutants: GPI anchor. Methods Enzymol. 416:182-205 (2006), and references in either of the foregoing.) For purposes of this invention, the polypeptides required by a cell to synthesize a GPI anchor and to attach the GPI anchor to a polypeptide (typically a polypeptide generated by cleavage of a precursor polypeptide comprising a GPI anchor attachment sequence) are referred to as the "GPI anchor synthesis and attachment machinery". Cleavage of a GPI anchor releases a GPI-anchored protein from the cell membrane typically leav ing a portion of the GPI anchor in the membrane (Sharom & Lehto, cited above).

For purposes of the present invention, the term "NOTUM substrate" encompasses molecules that are cleavable by NOTUM. In many embodiments, a "NOTUM substrate" is a compound comprising a GPI anchor or portion thereof that is cleavable by NOTUM. A "NOTUM substrate polypeptide" is a polypeptide that comprises a GPI anchor or portion thereof that is cleavable by NOTUM. In some aspects, a NOTUM substrate is a polypeptide comprising a GPI anchor that is cleaved by NOTUM in vivo (i.e., in a living organism). In some aspects, a NOTUM substrate is a polypeptide comprising a GPI anchor that is cleaved by NOTUM in vitro (i.e., in a cell culture system and/or in a system using at least partially purified components). Exemplary naturally occurring NOTUM substrate polypeptides include glypicans (e.g., human GPC3, GPC4, GPC5, or GPC6), uPAR (urokinase-type plasminogen activator receptor) and T-cadherin. NOTUM substrate polypeptides, when produced by cells, are typically produced as precursor polypeptides that comprise a GPI anchor attachment sequence, so that when the precursor polypeptide is synthesized in an appropriate cell (e.g., a cell that comprises the GPI anchor synthesis and attachment machinery) the precursor polypeptide undergoes processing that includes attachment of a GPI anchor. Polypeptides that lack a GPI anchor attachment sequence for a GPI anchor that is cleaved by NOTUM, can be modified to incorporate such a GPI anchor attachment sequence at their C-terminus. Such a modified polypeptide is sometimes referred to herein as an "artificial NOTUM substrate polypeptide".

A NOTUM substrate precursor polypeptide typically contains a signal sequence, e.g., at its N-terminus, which directs transfer of the precursor into the ER. The signal sequence may then be cleaved off such that is absent in the mature NOTUM substrate polypeptide cleaved by NOTUM. Often a signal sequence is about 5-30 amino acids long. Many signal sequences are known in the art and can be used in the present invention. The signal sequence that is present in the sequence of a naturally occurring NOTUM substrate polypeptide precursor (e.g., a naturally occurring polypeptide that is cleavable by NOTUM) may be replaced with a different signal sequence, e.g., from a different polypeptide destined for transport to the ER or an artificial signal sequence, comprising, e.g., at least about 5-10 hydrophobic amino acids. In many embodiments, the signal peptide does not comprise an ER retention sequence. In some embodiments, the signal sequence comprises at least a portion of a glypican signal peptide, e.g., at least a portion of a GPC3 signal sequence. In some embodiments, a signal peptide is amino acids 1-24 of the GPC3 precursor polypeptide.

Glypicans are a family of HS (heparan sulfate) proteoglycans that are linked to the plasma membrane via GPI anchors. Two glypicans have been identified in *Drosophila*: Daily (Division abnormally delayed) and Dlp (Dally-like protein). The mammalian glypican (GPC) family contains six members: GPC1-GPC6. The Gene ID numbers for genes encoding human glypicans and NCBI RefSeq accession numbers for human glypican proteins are listed in Table 1. As noted above, NOTUM has been shown to release various glypicans from the cell membrane. Without wishing to be bound by any theory, NOTUM may cleave the GPI anchor between the inositol-bound phosphate and the membrane-bound lipid. In some embodiments of the invention, a NOTUM inhibitor inhibits the ability of NOTUM to release one or more glypican proteins from the cell surface.

TABLE 1

Human glypicans

| Gene Name | Gene ID | mRNA/Protein RefSeq Accession Numbers |
|---|---|---|
| glypican 1 | 2817 | NM_002081/NP_002072 |
| glypican 2 | 221914 | NM_152742/NP_689955 |
| glypican 3 | 2719 | NM_001164617/NP_001158089 (isoform 1) |
|  |  | NM_004484/NP_004475 (isoform 2) |
|  |  | NM_001164618/NP_001158090 (isoform 3) |
|  |  | NM_001164619/NP_001158091 (isoform 4) |
| glypican 4 | 2239 | NM_001448/NP_001439 |
| glypican 5 | 2262 | NM_004466/NP_004457 |
| glypican 6 | 10082 | NM_005708/NP_005699 |

In some embodiments of the invention, a compound directly inhibits NOTUM, i.e., the compound inhibits NOTUM by a mechanism that involves a physical interaction (binding) between the NOTUM and the inhibitor. For example, binding of a NOTUM inhibitor to NOTUM can interfere with NOTUM's ability to catalyze a reaction (e.g., cleavage of a GPI anchor) and/or can occlude NOTUM's active site. A variety of compounds can be used to directly inhibit NOTUM. Exemplary compounds that directly inhibit NOTUM can be, e.g., small molecules, antibodies, or aptamers. In some embodiments, a direct inhibitor comprises a NOTUM substrate analog or a transition state analog. In some aspects, a NOTUM substrate comprises at least a portion of a GPI anchor comprising phosphatidylinositol. In some embodiments, a NOTUM substrate comprises phosphatidylinositol or an analog thereof. In some embodiments, a NOTUM inhibitor comprises a non-hydrolyzable analog of phosphatidylinositol.

In some embodiments of the invention, a NOTUM inhibitor binds covalently to NOTUM. For example, the compound may modify amino acid residue(s) that are needed for enzymatic activity. In some embodiments, a NOTUM inhibitor comprises one or more reactive functional groups such as an aldehyde, haloalkane, alkene, fluorophosphonate (e.g., alkyl fluorophosphonate), Michael acceptor, phenyl sulfonate, methylketone, e.g., a halogenated methylketone or diazomethylketone, fluorophosphonate, vinyl ester, vinyl sulfone, or vinyl sulfonamide, that reacts with an amino acid side chain of NOTUM. In some embodiments, a NOTUM inhibitor comprises a compound that physically interacts with NOTUM, wherein the compound comprises a reactive functional group. In some embodiments, the structure of a compound that physically interacts with NOTUM is modified to incorporate a reactive functional group. In some embodiments, the compound comprises a NOTUM substrate analog or transition state analog. In some embodiments, the compound interacts with NOTUM in or near the NOTUM active site. Ser 237, Asp 338, and His 384 have been predicted to form a catalytic triad in human NOTUM (12). In some embodiments, a NOTUM inhibitor covalently binds to one of these three amino acid residues, e.g., to a side chain thereof. In some embodiments, a substrate analog has a structure that comprises at least a portion of the structure of a GPI anchor that is cleaved by NOTUM or an analog of a GPI anchor that is cleaved by NOTUM. Methods of designing and making such NOTUM inhibitors are aspects of the invention.

In other embodiments, a NOTUM inhibitor binds non-covalently to NOTUM and/or to a complex containing NOTUM and a NOTUM substrate. In some embodiments, a NOTUM inhibitor binds non-covalently to the active site of NOTUM and/or competes with substrate(s) for access to the NOTUM active site. In some embodiments, a NOTUM inhibitor binds to NOTUM with a $K_d$ of approximately $10^{-3}$ M or less, e.g., $10^{-4}$ M or less, e.g., $10^{-5}$ M or less, e.g., $10^{-6}$ M or less, $10^{-7}$ M or less, $10^{-8}$ M or less, or $10^{-9}$ M or less under the conditions tested, e.g., in a physiologically acceptable solution such as phosphate buffered saline. Binding affinity can be measured, e.g., using surface plasmon resonance (e.g., with a Biacore system), isothermal titration calorimetry, or a competitive binding assay, as known in the art. In some embodiments, the inhibitor comprises a NOTUM substrate analog or transition state analog.

In some embodiments, a NOTUM inhibitor comprises a peptide that binds to NOTUM. In some embodiments, the peptide is identified using a display technique, such as phage display, bacterial display, yeast display, or ribosome display, using a NOTUM polypeptide (or a fragment or variant thereof) as a target. In one aspect, a candidate NOTUM inhibitor is identified by a method comprising (a) testing a plurality of peptides (e.g., a library of peptide generated using a display technique) for ability to specifically bind to NOTUM; and (b) selecting one or more peptides that binds to NOTUM. In some embodiments, the method comprises performing multiple rounds of testing, peptide synthesis, and selection. Successive rounds of synthesis may employ peptide(s) selected in a prior round as a starting point for generating a library of variants of such peptide(s), thereby facilitating selection of peptides of increasing affinity for the target in successive rounds of selection. In some embodiments, the method further comprises (c) determining whether a selected peptide inhibits at least one activity of NOTUM.

In some embodiments, a NOTUM inhibitor comprises an aptamer. In general, an aptamer is a single-stranded nucleic acid that binds to a particular molecule of interest. Aptamers are typically derived from an in vitro evolution and selection process such as SELEX. See, e.g., Brody E N, Gold L. *J Biotechnol.*, 74(1):5-13, 2000. In one aspect, a NOTUM inhibitor is identified using a method comprising (a) testing a plurality of nucleic acids (e.g., a library of at least partially randomly synthesized nucleic acids) for ability to specifically bind to NOTUM; and (b) selecting one or more oligonucleotides that binds to NOTUM. In some embodiments, the method comprises performing multiple rounds of testing, nucleic acid synthesis, and selection. Successive rounds of synthesis may employ nucleic acid(s) selected in a prior round as a starting point for generating a library of variants of such nucleic acid(s), thereby facilitating selection of nucleic acids of increasing affinity for the target in successive rounds of selection. In some embodiments, the method further comprises (c) determining whether a selected nucleic acid inhibits at least one activity of NOTUM.

In some embodiments, between $10^6$ and $10^{15}$ peptides or nucleic acids are tested, e.g., at least $10^6$, $10^7$, $10^8$, $10^9$, $10^{10}$, $10^{11}$, $10^{12}$, $10^{13}$, $10^{14}$ peptides or oligonucleotides. In some embodiments, peptides are between 5 and 15 amino acids long, e.g., between 7 and 12 amino acids long. In some embodiments, nucleic acids are between 6 and 100 nucleotides long, e.g., about 20 to about 80 nucleotides long.

In some embodiments, a NOTUM inhibitor comprises a variant of NOTUM that acts in a dominant negative manner. For example, the NOTUM variant may lack hydrolytic activity but retain the ability to bind to one or more NOTUM substrate(s), e.g., glypican GPI anchor(s). Such variants may compete with active NOTUM for binding to NOTUM substrates and thereby reduce NOTUM activity. In one aspect, a NOTUM inhibitor is identified using a method comprising (a) testing one or more NOTUM variants or fragments for ability to inhibit NOTUM activity; and (b) identifying one or more NOTUM variants or fragments that inhibits NOTUM activity.

In some embodiments, a NOTUM inhibitor comprises an antibody. In some embodiments, the antibody is a monoclonal antibody. In one aspect, a candidate NOTUM inhibitor is identified by a method comprising (a) testing a panel of monoclonal antibodies for ability to bind to NOTUM; and (b) identifying one or more monoclonal antibodies that bind specifically to NOTUM. In some embodiments, the method further comprises (c) determining whether an antibody identified in step (b) inhibits at least one activity of NOTUM.

The invention further provides a method for identifying a NOTUM modulator comprising determining whether a compound increases or decreases release of a GPI-anchored molecule from a membrane by NOTUM, wherein a compound that increases or decreases release of a GPI-anchored molecule from a membrane is identified as a NOTUM modulator. For example, a compound that increases release of a GPI-anchored molecule is identified as a NOTUM enhancer, and a compound that inhibits release of a GPI-anchored molecule is identified as a NOTUM inhibitor.

The invention further provides a method for identifying a NOTUM modulator comprising determining whether a compound increases or decreases the cleavage of a GPI anchor by NOTUM, wherein a compound that increases or decreases cleavage of a GPI anchor by NOTUM is identified as a NOTUM modulator. For example, a compound that increases cleavage of a GPI anchor by NOTUM is identified as a NOTUM enhancer, and a compound that inhibits cleavage of a GPI anchor by NOTUM is identified as a NOTUM inhibitor.

In some embodiments of the afore-mentioned methods for identifying a NOTUM modulator, the GPI anchor attaches a polypeptide to a membrane. Cleavage of the GPI anchor releases the polypeptide from the membrane. The released polypeptide may be detected, e.g., in a liquid medium that contacts the membrane. The membrane is typically a plasma membrane of a cell, e.g., a mammalian cell. In some embodiments an artificial membrane (e.g., an artificial phospholipid bilayer) or isolated cell membrane fragments may be used. Such approaches may be employed in the instant invention, e.g., to reconstitute a GPI-anchored NOTUM substrate polypeptide in an artificial membrane.

Certain aspects of the invention are described further in the next section.

III. Reporter-Based Screening Assays for NOTUM Modulators

The invention provides methods for identifying NOTUM modulators using (a) a reporter molecule comprising a GPI anchor and a second moiety; (b) a membrane; and (c) a NOTUM polypeptide, wherein the GPI anchor is attached to a membrane, e.g., the plasma membrane of a cell. In some embodiments, the second moiety comprises a detectable moiety. In some embodiments, the membrane is the plasma membrane of a cell, e.g., a cell that produces the reporter molecule. NOTUM releases at least a portion of the reporter molecule comprising the detectable moiety from the membrane, e.g., by cleaving the GPI anchor. In some embodiments, a portion of the reporter molecule comprising the detectable moiety is released into a liquid medium and is detected in the medium. A reporter molecule (or other molecule) that is attached to a membrane may be referred to herein as "membrane-bound". A membrane-bound molecule may be present in a detergent-soluble fraction of a cell lysate. A molecule that is not attached to a membrane or other surface (e.g., a moiety that is released into a liquid medium following cleavage of a GPI anchor) is sometimes referred to herein as "soluble". The invention provides screening assays that involve determining whether a test compound affects the ability of NOTUM to release a GPI-anchored reporter molecule from a membrane, wherein release is assessed based on the amount of soluble reporter molecule detected after maintaining the membrane in the presence of NOTUM for an appropriate time period. In some embodiments, the invention provides screening assays that involve determining whether a test compound affects the ability of NOTUM to cleave GPI anchors, wherein cleavage of the GPI anchor is assessed based on the amount of soluble reporter molecule detected after maintaining the membrane in the presence of NOTUM for an appropriate time period. The invention further provides reporter molecules and compositions useful for practicing the methods. In general, compounds identified using the inventive methods can act by any of mechanism that results in increased or decreased release of a GPI-anchored molecule from a membrane by NOTUM.

In one aspect, the invention provides a composition comprising (a) a reporter molecule comprising a GPI anchor and a detectable moiety; (b) a membrane; and (c) a NOTUM polypeptide, wherein the reporter molecule is attached to the membrane via the GPI anchor. The invention also provides a composition comprising (a) a reporter molecule comprising a GPI anchor and a detectable moiety; (b) a membrane; (c) a NOTUM polypeptide; and (d) a test compound, wherein the reporter molecule is attached to the membrane via the GPI anchor. The invention further provides a method comprising (i) providing (a) a reporter molecule comprising a GPI anchor and a detectable moiety; (b) a membrane; (c) a NOTUM polypeptide; (d) a test compound; and (ii) preparing a composition comprising the reporter molecule, membrane, NOTUM polypeptide, and test compound, wherein the reporter molecule is attached to the membrane via the GPI anchor.

In another aspect, the invention provides a method comprising (i) providing a composition comprising (a) a reporter molecule comprising a GPI anchor and a detectable moiety; (b) a membrane; (c) a NOTUM polypeptide; and (d) a test compound, wherein the reporter molecule is attached to the membrane via the GPI anchor; and (ii) determining whether the test compound modulates activity of the NOTUM polypeptide. For example, the method can comprise determining whether the compound enhances or inhibits release of the reporter molecule from the membrane. According to certain of the inventive methods, the composition is maintained under suitable conditions for release of the reporter molecule by NOTUM (e.g., by cleavage of the GPI anchor) to occur (i.e., conditions under which at least some release would occur in the absence of the test compound). In some embodiments, suitable conditions include a physiologically acceptable pH, temperature, and osmolarity for maintaining cells in tissue culture. The ability of the test compound to modulate (e.g., increase or decrease) release of the reporter molecule is assessed and, optionally, quantified and/or compared with a suitable reference value. The reference value may be a control value that represents, for example, the amount or rate of release that would occur in the absence of the test compound (under the same or similar assay conditions). A control assay may be performed in parallel or a historical control value may be used.

Reporter Molecules, Cells, and Membranes

In general, detectable moieties useful in the reporter molecules of the invention include light-emitting or light-absorbing compounds that generate or quench a detectable fluorescent, chemiluminescent, or bioluminescent signal. In some embodiments, cleavage of the GPI anchor causes release of the detectable moiety into a liquid medium, and the signal generated or quenched by the released detectable moiety present in the medium (or a sample thereof) is detected. In some embodiments, release of the detectable moiety, e.g., resulting from cleavage of the GPI anchor, causes an alteration in a property of the detectable moiety, and such alteration can be detected, e.g., as an optical signal. For example, release of the detectable moiety, e.g., resulting from cleavage of the GPI anchor, may alter the emission or absorption of electromagnetic radiation (e.g., radiation having a wavelength within the infrared, visible or UV portion of the spectrum) by the detectable moiety. In some embodiments, a reporter molecule comprises a fluorescent or luminescent moiety, and a second molecule serves as quencher that quenches the fluorescent or luminescent moiety. Release of the fluorescent or luminescent moiety due, e.g., to cleavage of the GPI anchor, causes the fluorescent or luminescent moiety to separate from the quencher so that quenching no longer occurs. The fluorescent or luminescent moiety can then be detected. In another embodiment the reporter molecule comprises a quencher, and release of the reporter molecule alters the spatial relationship of the fluorescent or luminescent moiety and the quencher so that quenching no longer occurs. In other embodiments, release of at least a portion of a reporter molecule may be detectable as a change in weight, light scattering, polarization, refraction, or other properties, of the reporter molecule, membrane, or surface on which the membrane is located. Such alteration can be detected using apparatus and methods known in the art.

In many embodiments of the invention, the reporter molecule is a genetically encodable molecule that can be expressed by a cell, and the detectable moiety comprises, e.g., a detectable polypeptide. Thus in some embodiments, the reporter molecule is a polypeptide comprising a GPI anchor and a detectable polypeptide. Exemplary detectable polypeptides of use in various embodiments of the invention include fluorescent polypeptides such as green, blue, sapphire, yellow, red, orange, and cyan fluorescent proteins and derivatives thereof (e.g., enhanced GFP); monomeric red fluorescent protein and derivatives such as those known as "mFruits", e.g., mCherry, mStrawberry, mTomato, etc., and luminescent proteins such as aequorin. (It will be understood that in some embodiments, the fluorescence or luminescence occurs in the presence of one or more additional molecules, e.g., an ion such as a calcium ion and/or a prosthetic group such as coelenterazine.) In some embodiments, the detectable moiety comprises an enzyme that acts on a substrate to produce a fluorescent, luminescent, colored, or otherwise detectable product. Examples of enzymes that may serve as detectable moieties include luciferase; beta-galactosidase; horseradish peroxidase; alkaline phosphatase; etc. (It will be appreciated that the enzyme is detected by detecting the product of the reaction.) In some embodiments, the detectable moiety comprises a polypeptide tag that can be readily detected using a second agent such as a labeled (e.g., fluorescently labeled) antibody. For example, fluorescently labeled antibodies that bind to the HA, Myc, or a variety of other peptide tags are available. Thus the invention encompasses embodiments in which a detectable moiety can be detected directly (i.e., it generates a detectable signal without requiring interaction with a second agent) and embodiments in which a detectable moiety interacts (e.g., binds and/or reacts) with a second agent and such interaction renders the detectable moiety detectable, e.g., by resulting in generation of a detectable signal or because the second agent is directly detectable. In embodiments in which a detectable moiety interacts with a second agent to produce a detectable signal, the detectable moiety may react with the second agent or is acted on by a second agent to produce a detectable signal. In many embodiments, the intensity of the signal provides an indication of the amount of detectable moiety present. e.g., in a sample being asssessed or in area being imaged. In some embodiments, the amount of detectable moiety is optionally quantified, e.g., on a relative or absolute basis, based on the signal intensity.

Figure 5:
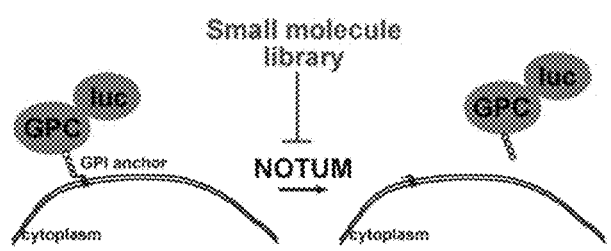
FIG. 5 is a schematic diagram of a chemical screen to identify inhibitors of NOTUM. Exogenous recombinant NOTUM protein causes cleavage of the GPI anchor of recombinant cell surface glypican molecules (GPC) translationally fused to a reporter (luc), such as luciferase or alkaline phosphatase. GPI anchor cleavage causes glypican release into the medium, a process that depends on NOTUM's hydrolase activity. Small molecules that cause a specific inability to release the glypican-reporter fusion protein into the cell medium are identified.

In some embodiments, the GPI anchor is a GPI anchor of a NOTUM substrate polypeptide. In some embodiments, the reporter molecule is a fusion protein comprising (i) a first portion comprising at least a portion of a NOTUM substrate polypeptide, wherein the at least a portion of a NOTUM substrate polypeptide comprises a GPI anchor; and (ii) a second portion comprising a detectable polypeptide. In many embodiments, the portion of the fusion protein comprising the detectable polypeptide is located N-terminal to the first portion of the polypeptide. In many embodiments, the GPI anchor is attached at the C-terminus of the fusion protein (see, e.g., FIG. 5).

The invention further provides a precursor polypeptide of a reporter polypeptide, wherein the precursor polypeptide comprises (a) a signal sequence; (b) a detectable polypeptide; and (c) a GPI anchor attachment sequence. When produced by a cell, the precursor is processed to generate a mature reporter polypeptide, which is attached to the cell membrane by the GPI anchor. Typically, the signal sequence is located at the N-terminus, and the GPI anchor attachment sequence is located at the C-terminus of the precursor polypeptide.

As noted above, many signal sequences are known in the art and can be used in the present invention. In general, any sequence sufficient to direct translocation of a polypeptide into the ER of a cell in which the polypeptide is expressed can be used in various embodiments of the invention. The sequence may, but need not, comprise the signal sequence of a GPI-anchored polypeptide. The sequence may, but need not, comprise the signal sequence of a naturally occurring precursor of a NOTUM substrate polypeptide.

A variety of GPI anchor attachment sequences can be used in the reporter molecules of the invention. In some embodiments, a GPI anchor attachment sequence of an experimentally verified GPI-anchored protein is used. Numerous experimentally verified GPI anchored proteins are known, and additional proteins predicted to be GPI anchored have been identified. (See, e.g., Paulick MG & Bertozzi CR, cited above, and Pierleoni, A., et al. (2008) PredGPI: a GPI-anchor predictor. BMC Bioinformatics 9:392, and references in either of these) The PredGPI database, which is publicly available and accessible via the world wide web lists proteins that have been annotated in SwissProt as experimentally verified GPI-anchored proteins (as well as predicted GPI-anchored proteins). A typical GPI anchor attachment sequence comprises the following C-terminal elements: (i) the cleavage site (sometimes termed the omega (ω) site), where the GPI anchor attaches to the COOH group of the ω amino acid; (ii) a moderately polar region of about 8 to 12 amino acids; and (iii) a hydrophobic region of about 10 to 20 amino acids. In some embodiments, a GPI anchor attachment sequence comprises: (i) a linker region, comprising about 11 residues before the position ω-1, often characterized by a low amount of predicted secondary structure; (ii) a region around the cleavage site, e.g., from ω-1 to ω+2, characterized by the presence of small side chain residues; (iii) a spacer region between, e.g., the positions ω+3 and ω+1-9; (iv) a hydrophobic tail, e.g., from ω+10 to the C-terminal end. Typical residues in the experimentally annotated ω-sites are cysteine, aspartic acid, glycine, asparagine, and serine, though other amino acids may be used. (See, e.g., Pierleoni, A., et al., cited above; Elortza F, et al., Proteomic analysis of glycosylphosphatidylinositol-anchored membrane proteins. Mol Cell Proteomics (2003) 2:1261-1270; Eisenhaber, B., P. Bork, and F. Eisenhaber. Sequence properties of GPI-anchored proteins near the omega-site: constraints for the polypeptide binding site of the putative transamidase. Protein Eng. (1998) 11:1155-1161, for non-limiting discussion of GPI anchor attachment sequences). In some embodiments, a reporter molecule comprises a GPI anchor attachment sequence found in a naturally occurring precursor of a polypeptide that is cleavable by NOTUM, such as a mammalian glypican, e.g., a human glypican. In some embodiments, the reporter molecule comprises a sequence identical to at least the C-terminal 20, 25, 30, 40, 50, 60, 70, 80, 90, 100, or more amino acids of a naturally occurring precursor of a NOTUM substrate polypeptide. In some embodiments, the reporter molecule comprises a sequence identical to a C-terminal domain of the precursor polypeptide, wherein the C-terminal domain comprises at least about 5%, 10%, 20%, 30%, 40%, 50%, 60%, 70%, 80%, 90%, 95%, or more of the precursor polypeptide, optionally excluding the signal sequence. For example, in some embodiments, the reporter molecule comprises a sequence identical to at least the C-terminal 20, 25, 30, 40, 50, 60, 70, 80, 90, 100, or more amino acids of human glypican 3. In some embodiments, the reporter molecule comprises a sequence identical to a C-terminal domain of at least about 5%, 10%, 20%, 30%, 40%, 50%, 60%, 70%, 80%, 90%, 95%, or more of human glypican 3.

In some embodiments, a reporter polypeptide comprises a detectable moiety that becomes covalently or noncovalently attached to the polypeptide after synthesis of the polypeptide by a cell. The detectable moiety can be attached intracellularly or after the polypeptide is exposed at the cell surface. In this regard, a fusion protein of the invention can comprise any of a variety of polypeptides that are capable of undergoing reactions with a substrate, resulting in covalent attachment of at least a portion of the substrate to the polypeptide. Such polypeptides are often enzymatically active, typically with specificity for a limited range of substrates. In some embodiments, the substrate(s) are molecules that are not normally found in the environment in which the polypeptide is typically present. For example, the substrate(s) are not normally found in cells that produce the polypeptide (or in media in which such cells are cultured). The substrate comprises a detectable moiety, which is transferred to the polypeptide as a result of the reaction. In some embodiments, HaloTag technology, or a similar system, is used to attach the detectable moiety to the polypeptide. HaloTag is a modified haloalkane dehalogenase designed to covalently bind to synthetic ligands (HaloTag ligands). The synthetic ligands comprise a chloroalkane linker attached to a molecule such as a fluorescent dye, affinity handle, or solid surface. Covalent bond formation between the protein tag (HaloTag) and the chloroalkane linker reportedly is highly specific, occurs rapidly under physiological conditions, and is essentially irreversible. See, e.g., Los G V, HaloTag: a novel protein labeling technology for cell imaging and protein analysis. ACS Chem Biol. 3(6): 373-82 (2008). In some embodiments, a reporter polypeptide comprises a SNAP-tag or CLIP-tag (both available from New England Biolabs, Ipswich, Mass.). SNAP-tag is a 20 kDa mutant of the DNA repair protein that reacts specifically and rapidly with benzylguanine (BG) derivatives, leading to irreversible covalent labeling of the SNAP-tag with the BG derivative, which can comprise any of a wide variety of different detectable moieties (Keppler, A. et al., Nat. Biotechnol. 21, 86 (2003)). CLIP-tag is a variant of SNAP-tag that reacts specifically with O2-benzylcytosine (BC) derivatives (Gautier, A., et al., Chem. Biol. 15, 128 (2008)).

In some embodiments, the invention provides a reporter polypeptide comprising: (a) a signal sequence; (b) a polypeptide capable of reacting specifically with a substrate, wherein the reaction results in covalent attachment of at least a portion of the substrate to the polypeptide; and (c) a polypeptide comprising a GPI anchor attachment sequence. Typically, the signal sequence is at the N-terminus, and the GPI attachment sequence is at the C-terminus. In some embodiments, the reporter polypeptide comprising a GPI anchor attachment sequence comprises at least a portion of a NOTUM substrate polypeptide. In some embodiments, the polypeptide capable of reacting specifically with a substrate comprises a HaloTag, SNAP-tag, or CLIP-tag polypeptide. In some embodiments, the GPI anchor attachment sequence is a NOTUM substrate GPI anchor attachment sequence (e.g., that of a glypican, e.g., GPC3). When the reporter polypeptide is expressed in a suitable cell, a GPI anchor is added in the ER, and the resulting polypeptide becomes anchored to the plasma membrane via the GPI anchor. In some embodiments, the membrane-bound polypeptide is then labeled, e.g., using a cell-impermeable label, prior to contacting the cell with the NOTUM polypeptide. This approach may, for example, allow the measurement specifically of GPI anchor cleavage that occurs at the cell membrane, e.g., cleavage of polypeptides that had been properly translocated to the plasma membrane, rather than those retained in the secretory pathway. In some embodiments, a cell-impermeable dye is an Alexa dye (e.g., AlexaFluo 350, AlexaFluor 488 or AlexaFluor 546), EAM-1, or Calcium green dextran. In some embodiments, the polypeptide is labeled using a cell-permeable label, such as carboxyfluorescein or BODIPY FL, which would permit labeling of surface-bound and intracellular polypeptides.

In some embodiments, a radioactive moiety is used to label a reporter molecule. For example, a reporter molecule produced by cells can be metabolically labelled with $[^{32}P]$Pi, $[^{3}H]$ethanolamine, etc.

In some embodiments, a reporter polypeptide comprises a moiety that is capable of binding to a detectable compound (e.g., a fluorescent label). For example, a reporter polypeptide can comprise a tetracysteine tag, which specifically chelates biarsenical compounds such as FlAsH and ReAsH that fluoresce upon binding to the tag (Martin, B R, et al., Nat Biotechnol. 23(10):1308-14 (2005)).

The invention provides nucleic acids comprising a sequence that encodes a reporter polypeptide of the invention. In some embodiments, a nucleic acid encodes a precursor polypeptide of a reporter polypeptide of the invention. In some embodiments, the sequence encoding the polypeptide is operably linked to expression control elements (e.g., a promoter or promoter/enhancer sequence) appropriate to direct transcription of mRNA encoding the polypeptide. The invention further provides expression vectors comprising the nucleic acids. Selection of appropriate expression control elements may be based, e.g., on the cell type and species in which the nucleic acid is to be expressed. One of ordinary skill in the art can readily select appropriate expression control elements and/or expression vectors. In some embodiments, expression control element(s) are regulatable, e.g., inducible or repressible. Exemplary promoters suitable for use in bacterial cells include, e.g., Lac, Trp, Tac, araBAD (e.g., in a pBAD vectors), phage promoters such as T7 or T3. Exemplary expression control sequences useful for directing expression in mammalian cells include, e.g., the early and late promoters of SV40, adenovirus or cytomegalovirus immediate early promoter, or viral promoter/enhancer sequences, retroviral LTRs, promoters or promoter/enhancers from mammalian genes, e.g., actin, EF-1 alpha, phosphoglycerate kinase, etc. Regulatable (e.g., inducible or repressible) expression systems such as the Tet-On and Tet-Off systems (regulatable by tetracycline and analogs such as doxycycline) and others that can be regulated by small molecules such as hormones receptor ligands (e.g., steroid receptor ligands, which may or may not be steroids), metal-regulated systems (e.g., metallothionein promoter), etc.

The invention further provides cells and cell lines that comprise such nucleic acids and/or vectors. In some embodiments, the cells are eukaryotic cells, e.g., fungal, plant, or animal cells. In some embodiments, a precursor polypeptide of the invention is expressed by a cell that contains the GPI anchor synthesis and attachment machinery. In some embodiments, the cell is a vertebrate cell, e.g., a mammalian cell, e.g., a human cell, non-human primate cell, or rodent cell. Often a cell is a member of a cell line, e.g., an established or immortalised cell line that has acquired the ability to proliferate indefinitely in culture (e.g., as a result of mutation or genetic manipulation). Numerous cell lines are known in the art and can be used in the instant invention. Mammalian cell lines include, e.g., HEK-293 (e.g., HEK-293T), CHO, NIH-3T3, COS, and HeLa cell lines. In some embodiments, a cell line is a tumor cell line. In other embodiments, a cell is non-tumorigenic and/or is not derived from a tumor. In some embodiments, the cells are adherent cells. In some embodiments, non-adherent cells are used. In some embodiments, a cell is of a cell type or cell line that has been shown to have GPI-anchored protein(s) present at its cell surface. For example, in some embodiments, the cell is of a cell type or cell line that has been shown to naturally have a NOTUM substrate polypeptide, e.g., a glypican, present at its cell surface. If a cell lacks one or more proteins of the GPI anchor synthesis and attachment machinery, the cell can be genetically engineered to express such protein(s). In some embodiments, a cell line of the invention is descended from a single cell. For example, a population of cells can be transfected with a nucleic acid encoding the reporter polypeptide and a colony derived from a single cell can be selected and expanded in culture. In some embodiments, cells are transiently transfected with an expression vector that encodes the reporter molecule. Cells can be co-transfected with a control plasmid, optionally expressing a different detectable polypeptide, to control for transfection efficiency (e.g., across multiple runs of an assay).

In some embodiments, the cell used in the method has low or absent expression of one or more naturally occurring NOTUM substrate polypeptides. For example, the cell may have low expression or absent expression of one or more glypicans (e.g., glypican 3). In some embodiments, the cell has reduced or absent expression of glycosylphosphatidylinositol specific phospholipase D1 (GPI-PLD; Gene ID: 2822 for the human gene), an enzyme that is able to cleave certain GPI anchors. A cell that has naturally has low or absent expression of one or more naturally occurring NOTUM substrate polypeptides and/or low or absent expression of GPI-PLD can be selected for use or generated using a variety of approaches. In some embodiments the gene(s) encoding one or more naturally occurring NOTUM substrate polypeptide(s) and/or GPI-PLD are inhibited using RNAi or knocked out, e.g., using homologous recombination. In some embodiments, use of a cell that has low or absent expression of one or more naturally occurring NOTUM substrate polypeptides and/or low or absent expression of GPI-PLD has one or more advantages. For example, use of such cells may improve the specificity and/or sensitivity of a screen for NOTUM modulators and/or increase the signal to noise ratio. In some embodiments, a cell is considered to have absent expression of a protein if the protein is not detectable above background levels in cells of that cell type using an appropriate method such as an immunoassay or activity assay. In some embodiments, a cell is considered to have low expression of a protein if the protein is not detectable above 1.5× background levels, or above 2× background levels, in cells of that cell type using an appropriate assay.

In some embodiments, a small organic molecule (e.g., a small organic fluorophore) or inorganic molecule is used as a detectable moiety. Examples of such molecules include various xanthenes (e.g., fluorescein), cyanines, naphthalenes, coumarins, oxadiazoles, pyrenes, oxazines, acridines, and derivatives of any of these, and others known to those skilled in the art. In some embodiments, nanoparticles such as semiconductor or metal-based nanoparticles are used. For example, quantum dots can be used. See, e.g., *The Molecular Probes® Handbook—A Guide to Fluorescent Probes and Labeling Technologies* (Invitrogen; Life Technologies, Inc.). In another embodiment, a biotin-avidin (or streptavidin) interaction is used as a basis for detection. For example, the reporter molecule can comprise biotin, which can be detected using labeled (e.g., fluorescently labeled) (strept)avidin or a variant thereof. Reporter molecules comprising a small molecule or nanoparticle as a detectable moiety may be used, e.g., in assays performed using a membrane that comprises a noncellular lipid layer (discussed below). A detectable moiety can be attached to an amino acid or to a GPI anchor using a variety of approaches and compounds known in the art. See, e.g., Hermanson, G., *Bioconjugate Techniques, $2^{nd}$* ed., Academic Press (2007) and *The Molecular Probes Handbook*, cited above. In general, such methods entail use of a detectable moiety linked to a moiety that comprises a functional group that reacts with one or more chemical groups present in the target molecule (e.g., polypeptide) to form a stable covalent bond. For example, the functional group may react with amines (e.g., at the polypeptide N-terminus or in a lysine side chain), thiols (e.g., in a cysteine side chain), carboxyl groups, etc. Amine-reactive groups include, e.g., succinimidyl esters and sulfonyl chlorides. Thiol-reactive groups include iodoacetamides, maleimides, and enzylic halides. Derivatives of detectable moieties, wherein the derivatives comprise a reactive functional group, can be used to produce a reporter molecule comprising the detectable moiety and a GPI anchor.

In some embodiments of the invention, a quencher is used, e.g., as part of a reporter molecule or to quench a fluorescent or luminescent moiety prior to release from a membrane. Quenchers include a variety of substances that decrease or alter a detectable signal produced by another substance, e.g., by absorbing energy emitted by the substance and emitting energy of a longer wavelength or, in the case of dark quenchers, dissipating the energy as heat.

In many embodiments of the invention, a reporter polypeptide comprising a GPI anchor is synthesized by cells. In some embodiments of the invention, a GPI anchor cleavable by NOTUM is synthesized at least in part using chemical synthesis. In some embodiments, a reporter polypeptide comprising a GPI anchor is synthesized at least in part using chemical synthesis, protein ligation, and/or in vitro translation. See, e.g., Becker, C F, et al, Angew Chem Int Ed Engl (2008), 47, 8215-8219; Paulick, M G & Bertozzi, C, Biochemistry (2008) 47, 6991-7000; Moran, P & Cell Biol (1991), 115, 1595-1600; Breydo, L, et al., Biochemistry (2007) 46, 852-861; Olschewski, D & Becker, C F., Mol Biosyst (2008) 4, 733-740. For example, a GPI anchor synthesized at least in part using chemical synthesis can be subsequently attached to a detectable moiety, e.g., a detectable polypeptide. Such molecules can be incorporated into artificial membranes or used as artificial substrates for NOTUM and/or to identify or characterize NOTUM modulators.

In some embodiments of the invention, a membrane comprises a noncellular lipid layer, which term refers to a lipid layer that is not part of an intact cell. In some embodiments, the noncellular lipid layer comprises a membrane preparation that has been isolated from cells that, for example, express a reporter molecule. In some embodiments, a noncellular lipid layer comprises one or more lipids arranged in a bilayer, wherein a GPI anchor can be integrated into the bilayer. In some embodiments, the noncellular lipid layer is not isolated from cells but rather is artificially prepared, e.g., from at least partially purified lipids. The noncellular lipid layer may be in the form of membrane fragments, vesicles (e.g., liposomes) or a substantially planar lipid bilayer. The noncellular lipid layer may be supported on a substrate such as glass (SiO2), metal, plastic, etc., in various embodiments. See, e.g., Dustin M L, et al., Curr Protoc Immunol. Chapter 18:Unit 18.13, 2007; Mossman, K. & Groves, J. T. Chem. Soc. Rev. 2007, 36, 46-54; and Parthasarathy, R. & Groves, J. T. Proc. Natl. Acad. Sci. U.S.A., 101, 12798-12803, 2004, for exemplary description of such bilayers and methods of making them. In general, the lipids can be naturally occurring (e.g., lipids that occur naturally in vertebrate cell membranes) or non-naturally occurring lipids in various embodiments of the invention. In some embodiments, the noncellular lipid layer comprises one or more phospholipids. Naturally occurring phospholipids include, e.g., phosphatidylcholine and phosphatidylethanolamine. In one embodiment, the bilayer is composed largely of phosphatidylcholine and contains about 3% phosphatidylethanolamine. See, e.g., Sharom & Lehto, cited above, for discussion of reconstitution of GPI-anchored proteins into bilayers, e.g., bilayers comprising defined phospholipids.

NOTUM Polypeptides and Nucleic Acids

A NOTUM polypeptide of use in the inventive methods may be obtained by a variety of methods. In some embodiments, the NOTUM polypeptide is produced using recombinant DNA techniques. Standard methods for recombinant protein expression can be used. A nucleic acid encoding NOTUM can readily be obtained, e.g., from cells that express NOTUM (e.g., by PCR or other amplification methods or by cloning) or by chemical synthesis or in vitro transcription based on a NOTUM cDNA sequence or NOTUM polypeptide sequence. One of ordinary skill in the art would know that due to the degeneracy of the genetic code, NOTUM can be encoded by many different nucleic acid sequences. Optionally, a sequence is codon-optimized for expression in a host cell of choice. NOTUM could be expressed in bacterial, fungal, animal, or plant cells or organisms. NOTUM could be isolated from cells that naturally express it or from cells into which a nucleic acid encoding NOTUM has been transiently or stably introduced, e.g., cells that contain an expression vector encoding NOTUM. In some embodiments, NOTUM is secreted by cells in culture and isolated from the culture medium. NOTUM could also be isolated from tissues or fluids obtained from an organism containing cells that express NOTUM. Standard protein isolation/purification techniques can be used to isolate and, optionally, purify NOTUM. In some embodiments, affinity-based methods are used. For example, an antibody or other binding agent can be employed. In some embodiments, NOTUM is synthesized with a tag that facilitates purification, in which case an appropriate isolation method can be selected depending on the particular tag used. In some embodiments, a preparation of NOTUM polypeptide is at least partially purified, e.g., at least 95% pure. In some embodiments, a NOTUM polypeptide is provided as a component of conditioned medium. Conditioned medium refers to culture medium in which cells have been cultured for a time period, typically several hours or more, during which the cells secrete various molecules into the medium. A conditioned medium containing NOTUM may be harvested from a cell culture comprising cells that express NOTUM (either naturally or as a result of genetic modification) and secrete it into the culture medium.

In some embodiments of the invention, the sequence of a NOTUM polypeptide of use in the inventive screening methods comprises or consists of the sequence of a naturally occurring NOTUM polypeptide. A naturally occurring NOTUM polypeptide can be from any species whose genome encodes a NOTUM polypeptide, e.g., human, non-human primate, rodent, etc. A polypeptide whose sequence is identical to naturally occurring NOTUM is sometimes referred to herein as "native NOTUM". A NOTUM polypeptide of use in the invention may or may not comprise a secretion signal sequence or a portion thereof. For example, a mature NOTUM polypeptide lacking a signal sequence is used in certain embodiments of the invention. For example, mature NOTUM comprising or consisting of amino acids 20-496 of human NOTUM (or corresponding amino acids of NOTUM of a different species) may be used.

In some embodiments, a polypeptide comprising or consisting of a variant or fragment of NOTUM is used. NOTUM variants include polypeptides that differ by one or more amino acid substitutions, additions, or deletions, relative to NOTUM. In some embodiments, a NOTUM variant comprises a polypeptide at least 70%, 75%, 80%, 85%, 90%, 95%, 96%, 97%, 98%, 99%, or more identical to at least amino acids 20-496 of NOTUM (e.g., from human or mouse) over at least 50%, 60%, 70%, 80%, 85%, 90%, 95%, 96%, 97%, 98%, 99%, or 100% of at least amino acids 20-496 of human NOTUM or amino acids 20-503 of mouse NOTUM. In some embodiments, a NOTUM variant comprises a polypeptide at least 80%, 85%, 90%, 95%, 96%, 97%, 98%, 99%, or more identical to at least amino acids 20-496 of human NOTUM or amino acids 20-503 of mouse NOTUM. In some embodiments, a NOTUM polypeptide comprises a polypeptide at least 80%, 85%, 90%, 95%, 96%, 97%, 98%, 99%, or more identical to at least amino acids 20-496 of human NOTUM or amino acids 20-503 of mouse NOTUM. A nucleic acid that encodes a NOTUM variant or fragment can readily be generated, e.g., by modifying the DNA that encodes native NOTUM using, e.g., site-directed mutagenesis, or by other standard methods, and used to produce the NOTUM variant or fragment. For example, a fusion protein can be produced by cloning sequences that encode NOTUM into a vector that provides the sequence encoding the heterologous portion. In some embodiments a tagged NOTUM is used. For example, in some embodiments a NOTUM polypeptide comprising a 6×His tag, e.g., at its C terminus, is used.

In some embodiments, a NOTUM variant is a functional variant, i.e., the variant at least in part retains the ability to release a GPI-anchored protein (e.g., a glypican) from the cell surface and/or the ability to cleave a GPI anchor. For example, the variant may retain between about 10% and about 100% of the activity of native NOTUM, e.g., between 50% and 100% of the activity of native NOTUM. A variant may have increased activity, e.g., between 100% and 200%, e.g., between 100% and 150% of the activity of native NOTUM. One of skill in the art can generate functional NOTUM variants or fragments.

In one aspect, the invention provides an isolated polypeptide whose amino acid sequence comprises or consists of the amino acid sequence of *S. mediterranea* NOTUM. The amino acid sequence of *S. mediterranea* NOTUM is presented in FIG. 6B and FIG. 8. (It will be appreciated that gaps have been introduced into the sequence in FIG. 8 for purposes of showing alignment of *S. mediterranea* NOTUM with NOTUM of other animal species). The invention further provides isolated variants and fragments of *S. mediterranea* NOTUM. In one aspect, the invention provides an isolated polypeptide comprising an amino acid sequence at least 70%, 80%, 90%, 91%, 92%, 93%, 94%, 95%, 96%, 97%, 98%, 99%, 99.5%, or more identical to *S. mediterranea* NOTUM over at least 100, 200, 300, 400, or 500 amino acids.

In another aspect, the invention provides an isolated nucleic acid comprising a sequence that encodes *S. mediterranea* NOTUM. The invention further provides an isolated nucleic acid comprising a sequence that encodes a variant or fragment of *S. mediterranea* NOTUM. In some embodiments, the isolated nucleic acid comprises a sequence that is identical to the naturally occurring sequence that encodes NOTUM in *S. mediterranea*. In some embodiments, the isolated nucleic acid comprises at least a portion of the Smed-notum 5' and/or 3' untranslated region(s) (UTRs), (See FIG. 6A for Smed-notum coding sequence and 5' and 3' UTRs). The invention further provides fragments of said isolated nucleic acid sequences. In some embodiments the nucleic acid is a fragment which is at least 8, 10, 15, 20, 25, 30, or 40 nucleotides in length, and less than 200, or less than 100, or less than 50, nucleotides in length in various embodiments. Such fragments may be used as probes (e.g., hybridization probes), e.g., to detect expression of the gene encoding *S. med.* NOTUM (e.g., by in situ hybridization, Northern blots, microarray hybridization, etc.) The invention further provides nucleic acid primers and primer pairs that may be useful, e.g., to synthesize a copy of or amplify (e.g., using PCR or other techniques known in the art) at least a portion of the gene or mRNA that encodes *S. med.* NOTUM and/or to detect a nucleic acid encoding *S. med.* NOTUM. In some embodiments, a probe or primer is an isolated or purified oligonucleotide which, in some embodiments, includes a region of nucleotide sequence that hybridizes under art-recognized stringent conditions to at least about 15, 20, 25, 30, 35, 40, 45, or 50 consecutive nucleotides of a naturally occurring Smed-notum sequence (see FIG. 6A) or to a complement thereof. The probe or primer may be perfectly complementary to such region. In some embodiments, a probe or primer may have, e.g., up to about 5%, or up to about 10% mismatches with respect to the region. For example, the probe or primer may contain 1, 2, 3, 4, or 5 mismatches with respect to the naturally occurring sequence. Exemplary primer sequences are provided in the Examples. A probe or primer can be derived from the sense or anti-sense strand of an *S. med.* notum sequence and may be derived from the coding region, 5' UTR, or 3'UTR in various embodiments. In some embodiments, the invention provides an isolated nucleic acid at least 70%, 80%, 90%, 91%, 92%, 93%, 94%, 95%, 96%, 97%, 98%, 99%, 99.5%, or more identical to the sequence that encodes NOTUM in *S. mediterranea*. Optionally a probe or primer is labeled with a detectable moiety.

The invention further provides recombinant nucleic acid constructs and vectors (e.g., expression vectors) comprising a nucleic acid sequence that encodes *S. mediterranea* NOTUM or that encodes a variant or fragment of *S. mediterranea* NOTUM. In some embodiments, the nucleic acid sequence is operably linked to expression control element(s), e.g., a promoter. Further provided are host cells that comprise a nucleic acid construct or expression vector. Such host cells may be used, e.g., to express *S. med.* NOTUM, which may then be used, e.g., in an inventive screening method.

The invention further provides RNAi agents, e.g., siRNA and shRNA, having sequence correspondence to *S. mediter-*

*ranea* mRNA. Exemplary sequences of use in such RNAi agents are provided in the Examples. Such RNAi agents are of use, e.g., to inhibit expression of the gene encoding *S. med.* NOTUM.

The invention further provides antibodies that bind to *S. med.* NOTUM. Such antibodies may be monoclonal or polyclonal and may be generated using standard methods using full length *S. med.* NOTUM or using a peptide fragment of *S. med.* NOTUM as an immunogen or as a target for the generation of antibodies using recombinant nucleic acid technology.

The invention further provides transgenic *S. mediterranea* organisms comprising a nucleic acid construct encoding *S. med,* NOTUM or encoding an RNAi agent or antisense agent that inhibits expression of *S. med.* NOTUM integrated into their genome.

Test Compounds

A wide variety of test compounds can be used in the inventive methods for identifying NOTUM modulators. For example, a test compound can be a small molecule, polypeptide, peptide, nucleic acid, oligonucleotide, lipid, carbohydrate, antibody, or hybrid molecule. Compounds can be obtained from natural sources or produced synthetically. Compounds can be at least partially pure or may be present in extracts or other types of mixtures whose components are at least in part unknown or uncharacterized. Extracts or fractions thereof can be produced from, e.g., plants, animals, microorganisms, marine organisms, fermentation broths (e.g., soil, bacterial or fungal fermentation broths), etc. In some embodiments, a compound collection ("library") is tested. The library may comprise, e.g., between 100 and 500,000 compounds, or more. Compounds are often arrayed in multwell plates (e.g., 384 well plates, 1596 well plates, etc.). They can be dissolved in a solvent (e.g., DMSO) or provided in dry form, e.g., as a powder or solid. Collections of synthetic, semi-synthetic, and/or naturally occurring compounds can be tested. Compound libraries can comprise structurally related, structurally diverse, or structurally unrelated compounds. Compounds may be artificial (having a structure invented by man and not found in nature) or naturally occurring. In some embodiments, a library comprises at least some compounds that have been identified as "hits" or "leads" in other drug discovery programs and/or derivatives thereof. A compound library can comprise natural products and/or compounds generated using non-directed or directed synthetic organic chemistry. Often a compound library is a small molecule library. Other libraries of interest include peptide or peptoid libraries, cDNA libraries, antibody libraries, and oligonucleotide libraries. A library can be focused (e.g., composed primarily of compounds having the same core structure, derived from the same precursor, or having at least one biochemical activity in common).

Compound libraries are available from a number of commercial vendors such as Tocris BioScience, Nanosyn, BioFocus, and from government entities. For example, the Molecular Libraries Small Molecule Repository (MLSMR), a component of the U.S. National Institutes of Health (NIH) Molecular Libraries Program is designed to identify, acquire, maintain, and distribute a collection of >300,000 chemically diverse compounds with known and unknown biological activities for use, e.g., in high-throughput screening (HTS) assays (available via the world wide web). The NIH Clinical Collection (NCC) is a plated array of approximately 450 small molecules that have a history of use in human clinical trials. These compounds are highly drug-like with known safety profiles. In some embodiments, a collection of compounds comprising "approved human drugs" is tested. An "approved human drug" is a compound that has been approved for use in treating humans by a government regulatory agency such as the US Food and Drug Administration, European Medicines Evaluation Agency, or a similar agency responsible for evaluating at least the safety of therapeutic agents prior to allowing them to be marketed. The test compound may be, e.g., an antineoplastic, antibacterial, antiviral, antifungal, antiprotozoal, antiparasitic, antidepressant, antipsychotic, anesthetic, antianginal, antihypertensive, antiarrhythmic, antiinflammatory, analgesic, antithrombotic, antiemetic, immunomodulator, antidiabetic, lipid- or cholesterol-lowering (e.g., statin), anticonvulsant, anticoagulant, antianxiety, hypnotic (sleep-inducing), hormonal, or antihormonal drug, etc. In some embodiments, a compound is one that has undergone at least some preclinical or clinical development or has been determined or predicted to have "drug-like" properties. For example, the test compound may have completed a Phase I trial or at least a preclinical study in non-human animals and shown evidence of safety and tolerability.

In some embodiments, a test compound is substantially non-toxic to cells of an organism to which the compound may be administered and/or to cells with which the compound may be tested, at the concentration to be used or, in some embodiments, at concentrations up to 10-fold, 100-fold, or 1,000-fold higher than the concentration to be used. For example, there may be no statistically significant effect on cell viability and/or proliferation, or the reduction in viability or proliferation can be no more than 1%, 5%, or 10% in various embodiments. Cytotoxicity and/or effect on cell proliferation can be assessed using any of a variety of assays. For example, a cellular metabolism assay such as AlamarBlue, MTT, MTS, XTT, and CellTitre Glo assays, a cell membrane integrity assay, a cellular ATP-based viability assay, a mitochondrial reductase activity assay, a BrdU, EdU, or H3-Thymidine incorporation assay could be used. In some embodiments, a test compound is not a compound that is found in a cell culture medium known or used in the art, e.g., culture medium suitable for culturing vertebrate, e.g., mammalian cells or, if the test compound is a compound that is found in a cell culture medium known or used in the art, the test compound is used at a different, e.g., higher, concentration when used in a method of the present invention.

Aspects of Assay Implementation and Controls

Various inventive screening assays described above involve determining whether a test compound modulates release of a GPI-anchored protein from a membrane by NOTUM. In most embodiments of the invention, the membrane is a plasma membrane of an intact cell (typically a viable cell), as described above. In certain of these embodiments, the reporter molecule is a recombinant polypeptide expressed by the cell, as described above, wherein the recombinant polypeptide comprises a detectable polypeptide and is attached to the cell membrane via a GPI anchor. Suitable cells for expression of a reporter molecule are described above. When produced by a cell, the precursor polypeptide is processed to generate a mature reporter polypeptide, which is attached to the cell membrane by the GPI anchor. The detectable moiety is located outside the cell, N-terminal to the GPI anchor. Release of the reporter polypeptide from the cell membrane following cleavage of the GPI anchor releases the detectable moiety from its attachment to the cell. (It will be understood that following such cleavage a portion of the GPI anchor may remain attached to the cell membrane.) In various embodiments of the invention the released detectable moiety is detected in the medium and/or the detectable moiety that remains tethered to the cell surface is detected.

In performing an inventive assay, assay components (e.g., cells, NOTUM polypeptide, and test compounds) are typically dispensed into multiple vessels or other containers. Any type of vessel or article capable of containing cells can be used. In many embodiments of the invention, the vessels are wells of a multi-well plate (also called a "microwell plate", "microtiter plate", etc. For purposes of description, the term "well" will be used to refer to any type of vessel or article that can be used to perform an inventive screen, e.g., any vessel or article that can contain the assay components. It should be understood that the invention is not limited to use of wells or to use of multi-well plates. In some embodiments, any article of manufacture in which multiple physically separated cavities (or other confining features) are present in or on a substrate can be used. For example, assay components can be confined in fluid droplets, which may optionally be arrayed on a surface and, optionally, separated by a water-resistant substance that confines the droplets to discrete locations, in channels of a microfluidic device, etc.

In general, assay components can be added to wells in any order. For example, cells can be added first and maintained in culture for a selected time period (e.g., between 6 and 48 hours) prior to addition of a test compound and NOTUM to a well. In some embodiments, compounds are added to wells prior to addition of NOTUM. In some embodiments, expression of a reporter polypeptide is induced after plating the cells, optionally after addition of a test compound and/or NOTUM to a well. In some embodiments, expression of the reporter molecule is achieved by transfecting the cells with an expression vector that encodes the reporter polypeptide. In some embodiments, the cells have previously been genetically engineered to express the reporter polypeptide. In some embodiments, expression of the reporter molecule is under control of regulatable expression control elements, and induction of expression of the reporter molecule is achieved by contacting the cells with an agent that induces (or derepresses) expression.

The assay composition comprising cells, test compound, and NOTUM is maintained for a suitable time period during which NOTUM may (in the absence of a test compound that inhibits its activity) cause release of the reporter polypeptide from the cell membrane. The number of cells, amount of NOTUM polypeptide, and amount of test compound to be added will depend, e.g., on factors such as the size of the vessel, cell type, and can be determined by one of ordinary skill in the art. In some embodiments, the ratio of the molar concentration of NOTUM polypeptide to test compound is between 1:10 and 10:1. In some embodiments, the number of cells, amount of NOTUM polypeptide, and length of time for which the composition is maintained can be selected so that a readily detectable level of soluble detectable moiety would be present in the medium after a selected time period in the absence of a test compound. In some embodiments, cells are at a confluence of about 25%-75%, e.g., about 50%, at the time of addition of compounds. In some embodiments, between 1,000 and 10,000 cells/well (e.g., about 5,000 cells/well) are plated in about 100 µl medium per well in 96-well plates. In other exemplary embodiments, cells are seeded in about 30 µl-50 µl of medium at between 500 and 2,000 (e.g., about 1000) cells per well into 384-well plates. In some embodiments, compounds are tested at multiple concentrations (e.g., 2-10 different concentrations) and/or in multiple replicates (e.g., 2-10 replicates). Multiple replicates of some or all different concentrations can be performed. In some embodiments, NOTUM is used at a concentration between 0.1 µg/ml and 100 µg/ml, e.g., 1 µg/ml and 10 µg/ml. In some embodiments, NOTUM is used at multiple concentrations. In some embodiments, compounds and NOTUM are added to cells between 6 hours and one day (24 hr) after seeding.

In some aspects of any of the inventive compound screening and/or characterization methods, a test compound is added to an assay composition in an amount sufficient to achieve a predetermined concentration. In some embodiments the concentration is up to about 1 nM. In some embodiments the concentration is between about 1 nM and about 100 nM. In some embodiments the concentration is between about 100 nM and about 10 µM. In some embodiments the concentration is at least 10 µM, e.g., between 10 µM and 100 µM. The assay composition can be maintained for various periods of time following addition of the last component thereof. In certain embodiments the assay composition is maintained for between about 10 minutes and about 4 days, e.g., between 1 hour and 3 days, e.g., between 2 hours and 2 days, or any intervening range or particular value, e.g., about 4-8 hours, after addition of all components. Multiple different time points can be tested. Additional aliquots of test compound can be added to the assay composition within such time period. In some embodiments, cells are maintained in cell culture medium appropriate for culturing cells of that type. In some embodiments, a serum-free medium is used. In some embodiments, the assay composition comprises a physiologically acceptable liquid that is compatible with maintaining integrity of the cell membrane and, optionally, cell viability, instead of cell culture medium. Any suitable liquid could be used provided it has the proper osmolarity and is otherwise compatible with maintaining reasonable integrity of the cell membrane and, optionally, cell viability, for at least a sufficient period of time to perform an assay. One or more measurements indicative of the amount of release of a reporter molecule and/or the amount of GPI anchor cleavage can be made during or following the incubation period.

In some embodiments, individual compounds, each typically of known identity (e.g., structure and/or sequence), are added to each of a multiplicity of wells. In some embodiments, two or more compounds may be added to one or more wells. In some embodiments, one or more compounds of unknown identity may be tested. The identity may be determined subsequently using methods known in the art.

In some embodiments of the invention, (a) a decrease in the amount of soluble detectable moiety (i.e., detectable moiety in the medium) in a test well as compared with a control well indicates that the test compound used in that well is a candidate NOTUM inhibitor; (b) an increase in the amount of cell-bound detectable moiety in a test well as compared with a control well indicates that the test compound used in that well is a candidate NOTUM inhibitor; (c) both a decrease in the amount of soluble detectable moiety in a test well as compared with a control well and an increase in the amount of cell-bound detectable moiety in a test well as compared with a control well indicates that the test compound used in that well is a candidate NOTUM inhibitor; or (d) an increase in the ratio of soluble to cell-bound detectable moiety in a test well as compared with a control well indicates that the test compound used in that well is a candidate NOTUM inhibitor. A suitable control well could be, e.g., a well lacking a test compound (optionally containing an equivalent amount of vehicle as used in the test well) or containing a test compound known not to significantly inhibit NOTUM.

In some embodiments, a non-cleavable reporter molecule is used as a control, e.g., to ensure that the identified compounds do not simply cause a lack of available reporter polypeptide. The non-cleavable reporter molecule typically comprises a different detectable moiety to that of the reporter molecule. The non-cleavable reporter molecule may lack a GPI anchor or may comprise a GPI anchor that is non-cleavable by NOTUM. In some embodiments, the sequence of a non-cleavable reporter polypeptide is generated by (i) mutating, deleting, or replacing the GPI anchor attachment sequence of the precursor of a reporter polypeptide; and (ii) replacing the sequence of the detectable polypeptide with that of a different detectable polypeptide (referred to hereafter as "control detectable polypeptide"). In some embodiments, the control detectable polypeptide is secreted. In some embodiments, the non-cleavable reporter polypeptide is attached to the cell membrane by a means other than a GPI anchor so that the control detectable polypeptide is attached to the cell surface but is not released by NOTUM. For example, the non-cleavable reporter polypeptide may contain a transmembrane domain. In some embodiments, the noncleavable reporter molecule is an intracellular polypeptide. The amount of detectable polypeptide released from the cell membrane in a given well in the presence of NOTUM may be normalized (typically based on detection of control detectable polypeptide on cells or in medium of the same well) to (i) the amount of control detectable polypeptide that is secreted (in the case of a secreted control polypeptide); (ii) the amount of control detectable polypeptide present at the cell surface (in the case of a cell-bound control detectable polypeptide); and/or (iii) the amount of control detectable polypeptide in cells and/or in the medium in the case of an intracellular control detectable polypeptide. In some embodiments, two or more non-cleavable reporter polypeptides (typically comprising different detectable polypeptides) are used. Test compounds that specifically affect the activity of NOTUM would alter the amount of detectable polypeptide detected but would typically have little or no effect on the amount of control detectable polypeptide detected. Test compounds that affect one or more processes such as transcription, translation, or ER translocation, would typically alter the amount of control detectable polypeptide. For example, test compounds that cause a lack of available reporter polypeptide, e.g., by inhibiting transcription, translation, ER translocation, etc., would cause a reduction in the amount of control detectable polypeptide that is secreted (in the case of a secreted control polypeptide) and/or the amount of control detectable polypeptide present at the cell surface (in the case of a cell-bound control detectable polypeptide). Test compounds that are cytotoxic would cause an increase in the amount of intracellular polypeptides present in the medium. Thus a variety of test compounds that would potentially be "false positives" could be identified as such and distinguished from genuine modulators of NOTUM.

In embodiments of the invention that utilize non-cellular lipid layers, the assay components can be dispensed into wells and assay performed in a generally similar manner as described above for assays involving living cells. Appropriate adjustments can be made. For example, assay compositions would typically not include cell culture medium but could instead use any liquid suitable for performing an in vitro enzyme assay. In other embodiments, a non-cellular lipid layer may be assembled on a surface that undergoes a change in one or more properties as a result of release of the reporter molecule. In some embodiments, a change in weight, reflectance, fluorescence, light scattering, index of refraction, polarization, or other parameter occurs as a result of release of a reporter molecule and can be measured using appropriate detection apparatus. In some embodiments, the surface comprises a sensing element that detects weight, reflectance, light scattering, index of refraction, or a change in any of these parameters.

In some embodiments, an inactive NOTUM polypeptide (e.g., a NOTUM polypeptide that has mutation in an active site residue), is used as a control in an inventive screening assay. An inactive NOTUM polypeptide may, for example, have a mutation at Ser 237 and/or at other amino acid(s) important for NOTUM activity. In one embodiment, Ser 237 is replaced by alanine. Such a control can be useful to assess whether a test compound that affects cleavage of the GPI anchor does so by modulating NOTUM activity or by a different mechanism. For example, if a test compound alters cleavage of the GPI anchor (as compared with cleavage that occurs in the absence of a test compound) to a greater extent in the presence of active NOTUM polypeptide than in the presence of inactive NOTUM polypeptide (under the same or similar assay conditions), the test compound is identified a modulator of NOTUM. If the test compound does not alter cleavage of the GPI anchor (as compared with cleavage that occurs in the absence of a test compound) to a greater extent in the presence of active NOTUM than in the presence of inactive NOTUM polypeptide (under the same or similar assay conditions), then the compound is not identified as a modulator of NOTUM activity (though it may still be useful as a modulator of GPI anchor cleavage). For example, if the test compound alters cleavage of the GPI anchor to approximately the same extent in the presence of active NOTUM as in the presence of inactive NOTUM, then the compound is not identified as a modulator of NOTUM activity. However, if significant cleavage occurs, as compared with cleavage in the absence of the test compound, the test compound is a potential modulator of a different protein (i.e., a protein other than NOTUM) that is capable of cleaving GPI anchors.

In various embodiments, foregoing assay methods of the invention are amenable to high-throughput screening (HTS) implementations. In some embodiments, the screening assays of the invention are high throughput or ultra high throughput (see, e.g., Fernandes, P. B., Curr Opin Chem. Biol. 1998, 2:597; Sundberg, S A, Curr Opin Biotechnol. 2000, 11:47). High throughput screens often involve testing large numbers of compounds with high efficiency, e.g., in parallel. For example, tens or hundreds of thousands of compounds can be routinely screened in short periods of time, e.g, hours to days. In some embodiments, HTS refers to testing of between 1,000 and 100,000 compounds per day. In some embodiments, ultra high throughput refers to screening in excess of 100,000 compounds per day, e.g., up to 1 million or more compounds per day. The screening assays of the invention may be carried out in a multi-well format, for example, a 96-well, 384-well format, 1,536-well format, or 3,456-well format and are suitable for automation. In some embodiments, each well of a microwell plate can be used to run a separate assay against a different test compound, or, if concentration or incubation time effects are to be observed, a plurality of wells can contain test samples of a single compound, with at least some wells optionally being left empty or used as controls or replicates. Typically, HTS implementations of the assays disclosed herein involve the use of automation. In some embodiments, an integrated robot system including one or more robots transports assay microwell plates between multiple assay stations for compound, cell and/or reagent addition, mixing, incubation, and readout or detection. In some aspects, an HTS system of the invention may prepare, incubate, and analyze many plates simultaneously. Suitable data processing and control software may be employed. High throughput screening implementations are well known in the art. Without limiting the invention in any way, certain general principles and techniques that may be applied in embodiments of a HTS of the present invention are described in Macarrón R & Hertzberg R P. Design and implementation of high-throughput screening assays. Methods Mol Biol., 565:1-32, 2009 and/or An W F & Tolliday N J., Introduction: cell-based assays for high-throughput screening. Methods Mol Biol. 486:1-12, 2009, and/or references in either of these. Exemplary methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jorg Hüser.

Detection of release of the detectable moiety can be performed using any suitable method known in the art. A laser scanner, fluorescence plate reader, or luminescence plate reader can be used. In some embodiments, fluorescence microscopy is used to gather an image of a plate. In some embodiments, a spectroscopy-based method or scintillation counting is used. In some embodiments, some or all of the liquid medium is removed from the wells and analyzed to detect a signal generated by the detectable moiety. Optionally, the medium is concentrated prior to analysis. In some embodiments, medium is transferred to wells of a different multiwell plate, which wells may contain one or more reagent(s) useful for detecting the detectable moiety (e.g., enzyme substrates, signal amplifiers, etc.), or to which one or more such reagent(s) are subsequently added. In some embodiments, medium is analyzed while remaining in the well. In some embodiments, a well contains a substance that amplifies a signal generated by released detectable moiety and does not amplify (or amplifies to a lesser extent), detectable moiety that remains associated with cells. In some embodiments, a well contains a substance that immobilizes a released reporter molecule. The substance may be, e.g., an antibody or a moiety that binds to a tag contained in the reporter molecule. Cells may be removed from the well, and the reporter molecule remaining in wells is then detected. In some embodiments, cells are analyzed by flow cytometry to detect reporter molecule that remains attached to the cell surface. In some embodiments, image processing is used, e.g., to distinguish between soluble detectable moiety and detectable moiety that remains attached to cells so as to allow specific detection of soluble and/or membrane-bound detectable moiety.

One or more additional test(s) can be performed in vitro or in vivo to confirm that a candidate NOTUM inhibitor inhibits NOTUM, if desired. For example, the effect of the compound on release of a GPI-anchored reporter molecule by NOTUM and/or on GPI anchor cleavage by NOTUM can be assessed using multiple different test cell populations, optionally comprising different reporter molecules, and/or the effect of the compound on GPI anchor cleavage of a NOTUM substrate, e.g., a naturally occurring NOTUM substrate, by NOTUM can be assessed. Another confirmatory test would be to show that the effect of the test compound depends on the presence of NOTUM, e.g., by showing that the test compound does not significantly affect release of the reporter molecule when an inactive variant of NOTUM is used in place of active NOTUM.

The effect of a test compound on the ability of NOTUM to inhibit Wnt expression can be assessed, wherein if the test compound inhibits the ability of NOTUM to inhibit Wnt expression, the test compound is a NOTUM inhibitor.

The effect of a test compound on Wnt signaling can be assessed, wherein in if the test compound inhibits the ability of NOTUM to inhibit Wnt signaling, the test compound is a NOTUM inhibitor. As noted above, the Wnt signaling pathway results in translocation of β-catenin to the nucleus where it forms a complex with TCF/LEF and directs expression of target genes. Wnt signaling may be assessed, e.g., using a β-catenin reporter plasmid comprising an element responsive to β-catenin/TCF/LEF, e.g., a reporter plasmid containing multimerized TCF/LEF DNA-binding sites. In some embodiments, if a candidate compound results in increased transcription of a β-catenin reporter in the presence of Wnt (e.g., Wnt3a) and NOTUM, as compared with transcription of the reporter in the presence of Wnt and NOTUM but in the absence of the test compound, the test compound is a NOTUM inhibitor. In some embodiments, this assay is performed using cells that express a glypican that is NOTUM substrate, e.g., glypican 3. A variety of Wnt/β-catenin reporter systems are known in the art and can be used to characterize candidate NOTUM modulators in vitro or in vivo. See, e.g., Biechele T L, Moon R T. Assaying beta-catenin/TCF transcription with beta-catenin/TCF transcription-based reporter constructs. Methods Mol Biol. 2008; 468: 99-110; Biechele, T., et al., Transcription-Based Reporters of Wnt/β-Catenin Signaling Cold Spring Harb Protoc; 2009; doi:10.1101/pdb.prot5223.

Additional compounds that modulate NOTUM can be identified or designed based on initial compounds ("hits") identified in a screen such as those described above. Such additional compounds and methods of designing or synthesizing them are an aspect of the invention. In some embodiments, structures of hit compounds are examined to identify a scaffold or pharmacophore, which can be used to design additional compounds.

An additional compound may, for example, have one or more improved pharmacokinetic and/or pharmacodynamic properties as compared with an initial hit or may simply have a different structure. An "improved property" may, for example, render a compound more effective or more suitable for one or more purposes described herein. In some embodiments, for example, a compound may have higher affinity for the molecular target of interest (e.g., NOTUM), lower affinity for a non-target molecule, greater solubility (e.g., increased aqueous solubility), increased stability (e.g., in blood, plasma, and/or in the gastrointestinal tract), increased half-life in the body, increased bioavailability, and/or reduced side effect(s), etc. Optimization can be accomplished through empirical modification of the hit structure (e.g., synthesizing compounds with related structures and testing them in cell-free or cell-based assays or in non-human animals) and/or using computational approaches. Such modification can in some embodiments make use of established principles of medicinal chemistry to predictably alter one or more properties. In some embodiments, one or more compounds that are "hit" are identified and subjected to systematic structural alteration to create a second library of compounds (e.g., refined lead compounds) structurally related to the hit. The second library can then be screened using any of the methods described herein.

In some embodiments, a NOTUM modulator is modified or incorporates a moiety that enhances cstability (e.g., in serum), increases half-life, reduces toxicity or immunogenicity, or otherwise confers a desirable property on the compound.

Additional Embodiments

Identification of NOTUM modulators is of particular interest, e.g., in regard to regeneration. The invention further provides methods and compositions relating to other polypeptides that release one or more GPI-anchored proteins from cell surfaces. Such a polypeptide may be referred to as a GPI-anchored protein releasing polypeptide ("GRP"). Compounds identified using the inventive methods can be used, e.g., to modulate the biological activity of the GPI-anchored proteins that are natural substrates of the GRP.

The invention provides methods for identifying modulators using (a) a reporter molecule comprising a GPI anchor and a second moiety; (b) a membrane; and (c) a GPI-anchored protein releasing polypeptide (GRP), wherein the GPI anchor is attached to a membrane, e.g., the plasma membrane of a cell. In some embodiments, the second moiety comprises a detectable moiety. In some embodiments, the membrane is the plasma membrane of a cell, e.g., a cell that produces the reporter molecule. The GRP releases at least a portion of the reporter molecule comprising the detectable moiety from the membrane, e.g., by cleaving the GPI anchor. The invention provides screening assays that involve determining whether a test compound affects the ability of a GRP to release a GPI-anchored reporter molecule from a membrane, wherein release is assessed based on the amount of soluble reporter molecule detected after maintaining the membrane in the presence of the GRP for an appropriate time period. In some embodiments, the invention provides screening assays that involve determining whether a test compound affects the ability of the GRP to cleave GPI anchors, wherein cleavage of the GPI anchor is assessed based on the amount of soluble reporter molecule detected after maintaining the membrane in the presence of the GRP for an appropriate time period. The invention further provides reporter molecules and compositions useful for practicing the methods.

In one aspect, the invention provides a composition comprising (a) a reporter molecule comprising a GPI anchor and a detectable moiety; (b) a membrane; and (c) a GRP, wherein the reporter molecule is attached to the membrane via the GPI anchor. The invention also provides a composition comprising (a) a reporter molecule comprising a GPI anchor and a detectable moiety; (b) a membrane; (c) a GRP; and (d) a test compound, wherein the reporter molecule is attached to the membrane via the GPI anchor. The invention further provides a method comprising (i) providing (a) a reporter molecule comprising a GPI anchor and a detectable moiety; (b) a membrane; (c) a GRP; (d) a test compound; and (ii) preparing a composition comprising the reporter molecule, membrane, GRP, and test compound, wherein the reporter molecule is attached to the membrane via the GPI anchor.

In another aspect, the invention provides a method comprising (i) providing a composition comprising (a) a reporter molecule comprising a GPI anchor and a detectable moiety; (b) a membrane; (c) a GRP; and (d) a test compound, wherein the reporter molecule is attached to the membrane via the GPI anchor; and (ii) determining whether the test compound modulates activity of the GRP. For example, the method can comprise determining whether the compound enhances or inhibits release of the reporter molecule from the membrane. According to certain of the inventive methods, the composition is maintained under suitable conditions for release of the reporter molecule by the GRP (e.g., by cleavage of the GPI anchor) to occur (i.e., conditions under which at least some release would occur in the absence of the test compound). In some embodiments, suitable conditions include a physiologically acceptable pH, temperature, and osmolarity for maintaining cells in tissue culture. The ability of the test compound to modulate (e.g., increase or decrease) release of the reporter molecule is assessed and, optionally, quantified and/or compared with a suitable reference value. The reference value may be a control value that represents, for example, the amount or rate of release that would occur in the absence of the test compound (under the same or similar assay conditions). A control assay may be performed in parallel or a historical control value may be used. Embodiments of the invention in which the GRP is NOTUM are described above. The invention provides additional embodiments in which the GRP is any GRP (e.g., a GRP from yeast, protozoa, plants, or mammals). In such embodiments, where the discussion above pertains to a NOTUM substrate, a substrate of the relevant GRP can be used, and where the discussion above pertains to a NOTUM polypeptide, the relevant GRP can be used.

IV. Uses of NOTUM Modulators

Pharmaceutical Compositions

NOTUM modulators have a variety of different uses. Non-limiting examples of such uses are discussed herein. In some embodiments, a NOTUM inhibitor is used to enhance regeneration of an organ or tissue. In some embodiments, a NOTUM inhibitor is used to enhance regeneration of a limb, digit, cartilage, heart, blood vessel, bone, esophagus, stomach, liver, gallbladder, pancreas, intestines, rectum, anus, endocrine gland (e.g., thyroid, parathyroid, adrenal, endocrine portion of pancreas), skin, hair follicle, thymus, spleen, skeletal muscle, smooth muscle, brain, spinal cord, peripheral nerve, ovary, fallopian tube, uterus, vagina, mammary gland, testes, vas deferens, seminal vesicle, prostate, penis, pharynx, larynx, trachea, bronchi, lungs, kidney, ureter, bladder, urethra, eye (e.g., retina, cornea), or ear (e.g., organ of Corti). In some embodiments, a NOTUM inhibitor is used to enhance regeneration of an epithelial layer, e.g., an epithelial layer lining the interior of a hollow organ. In some embodiments, a NOTUM inhibitor is used to enhance regeneration following surgery, e.g., surgery that entails removal of at least a portion of a diseased or damaged tissue, organ, or other structure such as a limb, digit, etc. For example, such surgery might remove at least a portion of a liver, lung, kidney, stomach, pancreas, intestine, mammary gland, ovary, testis, bone, limb, digit, muscle, skin, etc. In some embodiments, the surgery is to remove a tumor.

Enhancing regeneration can include any one or more of the following, in various embodiments: (a) increasing the rate of regeneration; (b) increasing the extent of regeneration; (c) promoting establishment of appropriate structure (e.g., shape, pattern, tissue architecture, tissue polarity) in a regenerating tissue or organ or other body structure; (d) promoting growth of new tissue in a manner that retains and/or restores function. While use of NOTUM inhibitors to enhance regeneration is of particular interest, the invention encompasses use of NOTUM inhibitors, to enhance repair or wound healing in general, without necessarily producing a detectable enhancement of regeneration. Thus, the invention provides methods of enhancing repair or wound healing, wherein a NOTUM inhibitor is administered to a subject in need thereof according to any of the methods described herein.

In some embodiments, the invention provides a method of enhancing regeneration in a subject in need thereof, the method comprising administering an effective amount of a NOTUM inhibitor to the subject. In some embodiments, an effective amount of a compound (e.g., a NOTUM inhibitor) is an amount that results in an increased rate or extent of regeneration of damaged tissue as compared with a reference value (e.g., a suitable control value). In some embodiments, the reference value is the expected (e.g., average or typical) rate or extent of regeneration in the absence of the compound (optionally with administration of a placebo). In some embodiments, an effective amount of a NOTUM inhibitor is an amount that results in an improved structural and/or functional outcome as compared with the expected (e.g., average or typical) structural or functional outcome in the absence of the compound. In some embodiments, an effective amount of a compound, e.g., a NOTUM inhibitor, results in enhanced blastema formation and/or reduced scarring. Extent or rate of regeneration can be assessed based on dimension(s) or volume of regenerated tissue, for example. Structural and/or functional outcome can be assessed based on, e.g., visual examination (optionally including use of microscopy or imaging techniques such as X-rays, CT scans, MRI scans, PET scans) and/or by evaluating the ability of the tissue, organ, or other body part to perform one or more physiological processes or task(s) normally performed by such tissue, organ, or body part. Typically, an improved structural outcome is one that more closely resembles normal structure (e.g., structure that existed prior to tissue damage or structure as it exists in a normal, healthy individual) as compared with the structural outcome that would be expected (e.g., average or typical outcome) in the absence of treatment with a NOTUM inhibitor. One of ordinary skill in the art can select an appropriate assay or test for function. In some embodiments, an increase in the rate or extent of regeneration as compared with a control value is statistically significant (e.g., with a p value of <0.05, or with a p value of <0.01) and/or clinically significant. In some embodiments, an improvement in structural and/or functional outcome as compared with a control value is statistically significant and/or clinically significant. "Clinically significant improvement" refers to an improvement that, within the sound judgement of a medical or surgical practitioner, confers a meaningful benefit on a subject (e.g., a benefit sufficient to make the treatment worthwhile). It will be appreciated that in many embodiments a NOTUM modulator, e.g., a NOTUM inhibitor, administered to a subject of a particular species (e.g., for therapeutic purposes) is a compound that modulates, e.g., inhibits, the endogenous NOTUM polypeptide expressed in subjects of that species. For example, if a subject is human, a compound that inhibits human NOTUM would typically be administered. The compound may also be an inhibitor of non-human NOTUM as well.

In some embodiments, a NOTUM inhibitor is used to enhance skin regeneration, e.g., after a burn (thermal or chemical), scrape injury, or other situations involving skin loss, e.g., infections such as necrotizing fasciitis or purpura fulminans. In some embodiments, a burn is a second or third degree burn. In some embodiments a region of skin loss has an area of at least 10 cm². In one aspect, a NOTUM inhibitor enhances regeneration of grafted skin. In one aspect, a NOTUM inhibitor reduces excessive and/or pathological wound contraction or scarring.

In some embodiments, a NOTUM inhibitor is used to enhance bone regeneration, e.g., in a situation such as non-union fracture, implant fixation, periodontal or alveolar ridge augmentation, craniofacial surgery, or other conditions in which generation of new bone is considered appropriate. In some embodiments, a NOTUM inhibitor is applied to a site where bone regeneration is desired. In some embodiments, a NOTUM inhibitor is incorporated into or used in combination with a bone graft material. Bone graft materials include a variety of ceramic and proteinaceous materials. Bone graft materials include autologous bone (e.g., bone harvested from the iliac crest, fibula, ribs, etc.), allogeneic bone from cadavers, and xenogeneic bone. Synthetic bone graft materials include a variety of ceramics such as calcium phosphates (e.g. hydroxyapatite and tricalcium phosphate), bioglass, and calcium sulphate, and proteinaceous materials such as demineralized bone matrix (DBM). DBM can be prepared by grinding cortical bone tissues (generally to 100-500 μm sieved particle size), then treating the ground tissues with hydrochloric acid (generally 0.5 to 1 N). In some embodiments, a NOTUM inhibitor is administered to a subject together with one or more bone graft materials. The NOTUM inhibitor may be combined with the bone graft material (in a composition comprising a NOTUM inhibitor and a bone graft material) or administered separately, e.g., after placement of the graft. In some embodiments, the invention provides a bone paste comprising a NOTUM inhibitor. Bone pastes are products that have a suitable consistency and composition such that they can be introduced into bone defects, such as voids, gaps, cavities, cracks etc., and used to patch or fill such defects, or applied to existing bony structures. Bone pastes typically have sufficient malleability to permit them to be manipulated and molded by the user into various shapes. The desired outcome of such treatments is that bone formation will occur to replace the paste, e.g., retaining the shape in which the paste was applied. The bone paste provides a supporting structure for new bone formation and may contain substance(s) that promote bone formation. Bone pastes often contain one or more components that impart a paste or putty-like consistency to the material, e.g., hyaluronic acid, chitosan, starch components such as amylopectin, in addition to one or more of the ceramic or proteinaceous bone graft materials (e.g., DBM, hydroxyapatite) mentioned above.

In some embodiments, a NOTUM inhibitor enhances the formation and/or recruitment of osteoprogenitor cells from undifferentiated mesechymal cells and/or enhances the differentiation of osteoprogenitor cells into cells that form new bone (osteoblasts).

In some embodiments, a NOTUM inhibitor is administered to a subject with osteopenia or osteoporosis, e.g., to enhance bone regeneration in the subject.

In some embodiments, a NOTUM inhibitor is used to enhance regeneration of a joint (e.g., a fibrous, cartilaginous, or synovial joint). In some embodiments, the joint is an intervertebral disc. In some embodiments, a joint is a hip, knee, elbow, or shoulder joint. In some embodiments, a NOTUM inhibitor is used to enhance regeneration of dental and/or periodontal tissues or structures (e.g., pulp, periodontal ligament, teeth, periodontal bone).

In some embodiments, a NOTUM inhibitor is used to enhance liver regeneration. As known in the art, the mammalian liver possesses significant regeneration potential after physical, biological, or chemical injury. For example, liver regeneration occurs commonly after liver damage caused by ischaemia or hepatitis (liver inflammation caused by insults such as toxins, viral infection or immune-mediated injury) and after surgical procedures such as removal of portions of the liver containing tumors. Without wishing to be bound by any theory, liver regeneration in many instances may occur mainly through the replication of mature functioning cells in the remaining viable liver. However, if a liver is too badly damaged or a liver remnant is too small, such regeneration may be insufficient or too slow to meet the needs of the individual. Furthermore, humans with certain hepatic conditions, including cirrhosis (fibrosis of the liver), steatosis (fatty liver), and sometimes aged individuals have impaired liver regeneration. In some embodiments, a NOTUM inhibitor enhances the formation and/or recruitment of liver progenitor cells (e.g., oval cells) and/or enhances the differentiation of liver progenitor cells into hepatocytes and/or cholangiocytes, thereby enhancing liver regeneration.

In some aspects, enhancing liver regeneration reduces the risks associated with partial liver resection and/or allow larger resections to be performed (potentially increasing the likelihood of cure). In some aspects, enhancing liver regeneration reduces the risks associated with living donor liver transplants (in which a portion of a liver is transplanted from one living person to another) and/or make it possible to perform a greater number of liver transplant procedures using a given amount of liver tissue (e.g., a cadaveric liver). A NOTUM inhibitor may be administered to a living liver donor or a recipient of a transplant of a partial or complete liver, or to a subject suffering from hepatic damage, e.g., due to viral infection (e.g., hepatitis A, B, C virus infection), chronic alcohol consumption, toxins, surgery, trauma, immune-mediated mechanisms, etc. In some embodiments, a subject has acute liver failure, e.g., due to ingestion of a hepatotoxic agent. Many pharmaceutical agents and non-pharmaceutical compounds can result in liver injury. For example, acetaminophen toxicity is one of the most common causes of poisoning worldwide and the most common cause of acute liver failure in the U.S. (Fontana, R., Acute liver failure including acetaminophen overdose. Med Clin North Am. 92(4):761-94 (2008)), and drug-induced hepatotoxicity is one of the most common reasons for withdrawal of previously approved drugs from the market.

In some embodiments, a NOTUM inhibitor is administered to a subject in combination with cells. The NOTUM inhibitor and the cells may be administered separately or in the same composition. If administered separately, they may be administered at the same or different locations. The cells can be autologous, allogeneic, or xenogeneic in various embodiments. The cells can comprise progenitor cells, e.g., stem cells, e.g., adult stem cells. As used herein, a stem cell is a cell that possesses at least the following properties: (i) self-renewal, i.e., the ability to go through numerous cycles of cell division while still maintaining an undifferentiated state; and (ii) multipotency or multidifferentiative potential, i.e., the ability to generate progeny of several distinct cell types (e.g., many, most, or all of the distinct cell types of a particular tissue or organ). An adult stem cell is a stem cell originating from non-embryonic tissues (e.g., fetal, post-natal, or adult tissues). As used herein, the term "progenitor cell" encompasses stem cells and cells that are more differentiated than stem cells but not fully differentiated. Such more differentiated cells (which may arise from stem cells) may, for example, have reduced capacity for self-renewal as compared with stem cells. For example, they may be unable to self-renew and/or may be able to undergo only up to about 5-10 cell divisions and/or they may give rise to a more limited set of differentiated cell types than stem cells (e.g., they may be oligopotent or unipotent). In some embodiments, a NOTUM inhibitor is administered in combination with mesenchymal progenitor cells, neural progenitor cells, endothelial progenitor cells, hair follicle progenitor cells, neural crest progenitor cells, mammary stem cells, lung progenitor cells (e.g., bronchioalveolar stem cells), muscle progenitor cells (e.g., satellite cells), adipose-derived progenitor cells, epithelial progenitor cells (e.g., keratinocyte stem cells), and/or hematopoietic progenitor cells (e.g., hematopoietic stem cells). In some embodiments, the cells comprise induced pluripotent stem cells (iPS cells), or cells that have been at least partly differentiated from iPS cells. In some embodiments, the progenitor cells comprise adult stem cells. In some embodiments, at least some of the cells are differentiated cells, e.g., chondrocytes, osteoblasts, keratinocytes, hepatocytes. In some embodiments, the cells comprise myoblasts.

In some embodiments, a NOTUM inhibitor is administered in a composition (e.g., a solution) comprising one or more compounds that polymerizes or becomes cross-linked or undergoes a phase transition in situ following administration to a subject, typically forming a hydrogel. The composition may comprise monomers, polymers, initiating agents, cross-linking agents, etc. The composition may be applied (e.g., using a syringe) to an area where regeneration is needed, where it forms a gel in situ, from which the NOTUM inhibitor is released over time. Gelation may be triggered, e.g., by contact with ions in body fluids or by change in temperature or pH, or by light, or by combining reactive precursors (e.g., using a multi-barreled syringe). See, e.g., U.S. Pat. No. 6,129,761; Yu L, Ding J. Injectable hydrogels as unique biomedical materials. Chem Soc Rev. 37(8):1473-81 (2008)). In some embodiments, the composition further comprises cells.

Other inventive methods comprise use of a NOTUM modulator in the ex vivo production of living, functional tissues, organs, or cell-containing compositions to repair or replace a tissue or organ lost due to damage. For example, cells or tissues removed from an individual (either the future recipient, an individual of the same species, or an individual of a different species) may be cultured in vitro, optionally with an matrix, scaffold (e.g., a three dimensional scaffold) or mold (e.g., comprising a biocompatible, optionally biodegradable, material, e.g., a polymer), and their development into a functional tissue or organ can be promoted by contacting with a NOTUM inhibitor. The scaffold, matrix, or mold may be composed at least in part of naturally occurring proteins such as collagen, hyaluronic acid, or alginate (or chemically modified derivatives of any of these), or synthetic polymers or copolymers of lactic acid, caprolactone, glycolic acid, etc., or self-assembling peptides, or decellularized matrices derived from tissues such as heart valves, intestinal mucosa, blood vessels, and trachea. In some embodiments, the scaffold comprises a hydrogel. The scaffold may, in certain embodiments, be coated or impregnated with a NOTUM inhibitor, which may diffuse out from the scaffold over time. After production ex vivo, the tissue or organ is grafted into or onto a subject. For example, the tissue or organ can be implanted or, in the case of certain tissues such as skin, placed on a body surface. The tissue or organ may continue to develop in vivo. In some embodiments, the tissue or organ to be produced at least in part ex vivo is a bladder, blood vessel, bone, fascia, liver, muscle, skin patch, etc. Suitable scaffolds may, for example, mimic the extracellular matrix (ECM). Optionally a NOTUM inhibitor is administered to the subject prior to, during, and/or following grafting of the ex vivo generated tissue or organ. In some aspects, a biocompatible material is a material that is substantially non-toxic to cells in vitro at the concentration used or, in the case of a material that is administered to a living subject, is substantially nontoxic to the subject's cells in the quantities and at the location used and does not elicit or cause a significant deleterious or untoward effect on the subject, e.g., an immunological or inflammatory reaction, unacceptable scar tissue formation, etc. It will be understood that certain biocompatible materials may elicit such adverse reactions in a small percentage of subjects, typically less than about 5%, 1%, 0.5%, or 0.1%.

In some embodiments, a matrix or scaffold coated or impregnated with a NOTUM inhibitor is implanted, optionally in combination with cells, into a subject in need of regeneration. The matrix or scaffold may be in the shape of a tissue or organ whose regeneration is desired. The cells may be stem cells of one or more type(s) that gives rise to such tissue or organ and/or of type(s) found in such tissue or organ.

In some embodiments, a NOTUM inhibitor is administered directly to or near a site of tissue damage. "Directly to a site of tissue damage" encompasses injecting a compound or composition into a site of tissue damage or spreading, pouring, or otherwise directly contacting the site of tissue damage with the compound or composition. In some embodiments, administration is considered "near a site of tissue damage" if administration occurs within up to about 10 cm away from a visible or otherwise evident edge of a site of tissue damage or to a blood vessel (e.g., an artery) that is located at least in part within the damaged tissue or organ. Administration "near a site of tissue damage" is sometimes administration within a damaged organ, but at a location where damage is not evident. In some embodiments, following damage or loss of a tissue, organ, or other structure, a NOTUM inhibitor is applied to the remaining portion of the tissue, organ, or other structure. In some embodiments, a NOTUM inhibitor is applied to the end of a severed digit or limb) that remains attached to the body, to enhance regeneration of the portion that has been lost. In some embodiments, the severed portion is reattached surgically, and a NOTUM inhibitor is applied to either or both faces of the wound. In some embodiments, a NOTUM inhibitor is administered to enhance engraftment or healing or regeneration of a transplanted organ or portion thereof. In some embodiments, a NOTUM inhibitor is used to enhance nerve regeneration. For example, a NOTUM inhibitor may be infused into a severed nerve, e.g., near the proximal and/or distal stump. In some embodiments, a NOTUM inhibitor is placed within an artificial nerve conduit, a tube composed of biological or synthetic materials within which the nerve ends and intervening gap are enclosed.

In some embodiments, a NOTUM inhibitor is used to promote production of hair follicles and/or growth of hair. In some embodiments a NOTUM inhibitor triggers regeneration of hair follicles from epithelial cells that do not normally form hair. In some embodiments, a NOTUM inhibitor is used to treat hair loss, hair sparseness, partial or complete baldness in a male or female. In some embodiments, baldness is the state of having no or essentially no hair or lacking hair where it often grows, such as on the top, back, and/or sides of the head. In some embodiments, hair sparseness is the state of having less hair than normal or average or, in some embodiments, less hair than an individual had in the past or, in some embodiments, less hair than an individual considers desirable. In some embodiments, a NOTUM inhibitor is used to promote growth of eyebrows or eyelashes. In some embodiments, a NOTUM inhibitor is used to treat androgenic alopecia or "male pattern baldness" (which can affect males and females). In some embodiments, a NOTUM inhibitor is used to treat alopecia greata, which involves patchy hair loss on the scalp, alopecia totalis, which involves the loss of all head hair, or alopecia universalis, which involves the loss of all hair from the head and the body. In some embodiments, a NOTUM inhibitor is applied to a site where hair growth is desired, e.g., the scalp or eyebrow region. In some embodiments, a NOTUM inhibitor is applied to or near the edge of the eyelid, to promote eyelash growth. In some embodiments, a NOTUM inhibitor is applied in a liquid formulation. In some embodiments a NOTUM inhibitor is applied in a cream, ointment, paste, or gel. In some embodiments, a NOTUM inhibitor is used to enhance hair growth after a burn, surgery, chemotherapy, or other event causing loss of hair or hear-bearing skin.

In some embodiments, a NOTUM inhibitor is administered to enhance replacement of cells that have been lost or damaged due to insults such as chemotherapy, radiation, or toxins. In some embodiments such cells are epithelial cells (e.g., cells lining the intestinal tract) or hematopoietic cells.

Inventive methods of treatment can include a step of identifying or providing a subject suffering from or at risk of a disease or condition in which in which enhancing regeneration would be of benefit to the subject. In some embodiments, the subject has experienced injury (e.g., physical trauma) or damage to a tissue or organ. In some embodiments the damage is to a limb or digit. In some embodiments, a subject suffers from a disease affecting the cardiovascular, digestive, endocrine, musculoskeletal, gastrointestinal, hepatic, integumentary, nervous, respiratory, or urinary system. In some embodiments, tissue damage is to a tissue, organ, or structure such as cartilage, bone, heart, blood vessel, esophagus, stomach, liver, gallbladder, pancreas, intestines, rectum, anus, endocrine gland, skin, hair follicle, tooth, gum, lip, nose, mouth, thymus, spleen, skeletal muscle, smooth muscle, joint, brain, spinal cord, peripheral nerve, ovary, fallopian tube, uterus, vagina, mammary gland, testes, vas deferens, seminal vesicle, prostate, penis, pharynx, larynx, trachea, bronchi, lungs, kidney, ureter, bladder, urethra, eye (e.g., retina, cornea), or ear (e.g., organ of Corti).

In some embodiments a compound or composition is administered to a subject at least once within approximately 2, 4, 8, 12, 24, 48, 72, or 96 hours after a subject has suffered tissue damage (e.g., an injury or an acute disease-related event such as a myocardial infarction or stroke) and, optionally, at least once thereafter. In some embodiments a compound or composition is administered to a subject at least once within approximately 1-2 weeks, 2-6 weeks, or 6-12 weeks, after a subject has suffered tissue damage and, optionally, at least once thereafter.

In some embodiments of the invention, it may useful to stimulate or facilitate regeneration or de novo development of a missing or hypoplastic tissue, organ, or structure by, for example, removing the skin, removing at least some tissue at a site where regeneration or de novo development is desired, abrading a joint or bone surface where regeneration or de novo development is desired, and/or inflicting another type of wound on a subject. In the case of regeneration after tissue damage, it may be desirable to remove (e.g., by surgical excision or debridement) at least some of the damaged tissue. In some embodiments, a NOTUM inhibitor is administered at or near the site of such removal or abrasion.

In some embodiments, a NOTUM inhibitor is used to enhance generation of a tissue or organ in a subject in whom such tissue or organ is at least partially absent as a result of a congenital disorder, e.g., a genetic disease. Many congenital malformations result in hypoplasia or absence of a variety of tissues, organs, or body structures such as limbs or digits. In other instances a developmental disorder resulting in hypoplasia of a tissue, organ, or other body structure becomes evident after birth. In some embodiments, a NOTUM inhibitor is administered to a subject suffering from hypoplasia or absence of a tissue, organ, or other body structure, in order to stimulate growth or development of such tissue, organ, or other body structure. In some aspects, the invention provides a method of enhancing generation of a tissue, organ, or other body structure in a subject suffering from hypoplasia or congenital absence of such tissue, organ, or other body structure, the method comprising administering a NOTUM inhibitor to the subject. In some embodiments, a NOTUM inhibitor is administered to the subject prior to birth, i.e., in utero. The various aspects and embodiments of the invention described herein with respect to regeneration are applicable to such de novo generation of a tissue, organ, or other body structure and are encompassed within the invention.

In some aspects, a NOTUM inhibitor is used to enhance generation of tissue in any of a variety of situations in which new tissue growth is useful at locations where such tissue did not previously exist. For example, generating bone tissue between joints is frequently useful in the context of fusion of spinal or other joints.

NOTUM modulators may be tested in a variety of animal models of regeneration. In one aspect, a modulator of planarian NOTUM is tested in planarians. For example, planarians can be wounded (e.g., by incision, amputation, transection, or removal of a tissue fragment). A NOTUM inhibitor is applied to the site of the wound and/or to a removed tissue fragment and its effect on regeneration is assessed. The effect of a modulator of vertebrate NOTUM can be tested in a variety of vertebrate models for tissue or organ regeneration. For example, fin regeneration can be assessed in zebrafish, e.g., as described in (Mathew L K, Unraveling tissue regeneration pathways using chemical genetics. J Biol Chem. 282(48): 35202-10 (2007)), and can serve as a model for limb regeneration. Rodent, canine, equine, caprine, fish, amphibian, and other animal models useful for testing the effects of treatment on regeneration of tissues and organs such as heart, lung, limbs, skeletal muscle, bone, etc., are widely available. For example, various animal models for musculoskeletal regeneration are discussed in Tissue Eng Part B Rev. 16(1) (2010). A commonly used animal model for the study of liver regeneration involves surgical removal of a larger portion of the rodent liver. Other models for liver regeneration include acute or chronic liver injury or liver failure caused by toxins such as carbon tetrachloride. In some embodiments, a model for hair regeneration or healing of skin wounds involves excising a patch of skin, e.g., from a mouse. Regeneration of hair follicles, hair growth, re-epithelialization, gland formation, etc., can be assessed.

In other aspects of the invention a NOTUM inhibitor is used to enhance Wnt signaling for purposes other than promoting regeneration. In some embodiments, such purposes are therapeutic purposes, e.g., to enhance Wnt signaling in disorders in which reduced Wnt signaling plays a causative or contributing role, or in which enhanced Wnt signaling is useful to treat a disease. In other embodiments, enhancing Wnt signaling is useful for research purposes in vivo or in vitro, e.g., to gather additional information regarding the Wnt pathway and its effects. In some embodiments, a NOTUM modulator is used to generate an animal model for a condition associated with altered Wnt signaling. In some embodiments, a NOTUM inhibitor is used for any purpose for which Wnt administration is contemplated to be useful.

In some embodiments, a NOTUM inhibitor is contacted with cells ex vivo, optionally together with one or more additional compounds, to alter their differentiation state and/or promote their expansion. In some embodiments, the cells comprise cells that express NOTUM and a GPI-anchored protein that is cleaved by NOTUM, e.g., a glypican, e.g., glypican 3. In some embodiments, enhancement of Wnt signaling using a NOTUM inhibitor is useful to enhance reprogramming a somatic cell to a less differentiated state, e.g., to a pluripotent state, e.g., in combination with one or more proteins such as Oct4, Sox2, Klf4, c-Myc, or Nanog or compounds such as small molecules that can replace such factor(s) in reprogramming. In some embodiments, a NOTUM inhibitor is used in the ex vivo expansion of progenitor cells, e.g., stem cells. In some embodiments, the expanded cells or differentiated descendants thereof are administered to a subject. In other embodiments the expanded cells are used in vitro, e.g., in screening of compounds.

In another aspect, the invention provides a method of enhancing regeneration comprising administering a soluble glypican polypeptide to a subject in need thereof. In some aspects, a soluble glypican polypeptide lacks a GPI anchor and/or is not attached to a membrane. In some embodiments, a soluble glypican is produced by contacting a cell that expresses a GPI-anchored glypican with a NOTUM polypeptide. The NOTUM polypeptide cleaves the GPI-anchored glypican, thereby releasing it from the cell membrane into the culture medium. The soluble glypican is then isolated from the medium. In some embodiments, a soluble glypican is produced by a cell that lacks at least one component of the GPI anchor synthesis and attachment machinery. As a result, the glypican polypeptide is produced without a functional GPI anchor and, in at least some embodiments, is secreted by the cell. The cell may, for example, have a mutation in a gene required for GPI anchor synthesis or attachment. The soluble glypican is then isolated from the medium. In some embodiments, a soluble glypican is produced from a precursor polypeptide that lacks a GPI attachment sequence. For example, a nucleic acid sequence encoding the glypican can be modified by deleting the GPI anchor attachment sequence or altering the GPI anchor attachment sequence such that it no longer functions as a GPI anchor attachment sequence. A cell may express a glypican polypeptide naturally or as a result of genetic engineering. In some embodiments, a glypican polypeptide has the sequence of a naturally occurring glypican polypeptide. A naturally occurring glypican polypeptide can be from any species whose genome encodes a glypican, in various embodiments of the invention. For example, a glypican polypeptide can be of vertebrate origin, e.g., of human, non-human primate, or rodent origin. In some embodiments, a glypican polypeptide can be any glypican polypeptide that binds to a Wnt ligand. In some embodiments, a glypican polypeptide is glypican 3. In some embodiments, a glypican polypeptide comprises a variant or fragment of a naturally occurring glypican polypeptide, e.g., glypican 3. For example, a glypican polypeptide can comprise a polypeptide at least 70%, 75%, 80%, 85%, 90%, 91%, 02%, 93%, 94%, 95%, 96%, 97%, 98%, 99%, or more identical to at least that portion of a naturally occurring glypican polypeptide that is released from the cell membrane by NOTUM. In some embodiments, a glypican polypeptide comprises a sequence at least 90%, 91%, 92%, 93%, 94%, 95%, 96%, 97%, 98%, 99%, or more identical to a sequence that occurs naturally in the organism to which the glypican polypeptide is administered. For example, if the subject is human a polypeptide at least 90%, 91%, 92%, 93%, 94%, 95%, 96%, 97%, 98%, 99%, or more identical to at least that portion of a naturally occurring human glypican polypeptide that is released from the cell membrane by NOTUM can be administered.

NOTUM enhancers may be identified using inventive assays described herein. Such compounds have a variety of uses. In some embodiments, a NOTUM enhancer is useful to antagonize Wnt signaling. In some embodiments, a NOTUM enhancer is used to treat a disorder associated with increased bone volume, abnormally elevated bone density (hyperostosis) and/or pathological thickening of bone. In one embodiment, the disorder is a sclerosing bone dysplasia, which term refers collectively to a group of genetic disorders characterized by the creation of abnormally dense and overgrown bones. In some embodiments, the sclerosing bone dysplasia is endosteal hyperostosis, sclerosteosis, van Buchem disease, high bone-mass syndrome, or osteopathia striata. In some embodiments, the sclerosing bone dysplasia is caused by a mutation in a Wnt pathway component, which mutation results in increased Wnt signaling. In some embodiments, the mutation is in the gene encoding Low Density Lipoprotein-Related Protein (LRP5). In some embodiments, the disorder is a tumor, e.g., a tumor associated with excessive Wnt signaling. In some embodiments, the tumor is a malignant neoplasm. In certain embodiments, the tumor is a cancer. In certain embodiments the cancer is a solid tumor. Exemplary cancers include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, gallbladder cancer, laryngeal cancer, oral cancer, penile cancer, glandular tumors, rectal cancer, small intestine cancer, sarcoma, melanoma, urethral cancer, vaginal cancer. In some embodiments, the cancer is a hematological malignancy. In some embodiments, the hematological malignancy is a lymphoma. In some embodiments, the hematological malignancy is a leukemia. Examples of hematological malignancies include, but are not limited to, acute lymphoblastic leukemia, acute myelogenous leukemia, chronic myelogenous leukemia, chronic lymphocytic leukemia, hairy cell leukemia, Hodgkin's lymphoma, non-Hodgkin's lymphoma, cutaneous T-cell lymphoma, peripheral T-cell lymphoma, mantle cell lymphoma, B-cell lymphoma, acute lymphoblastic T cell leukemia, acute promyelocyte leukemia, and multiple myeloma.

The compounds and compositions disclosed herein and/or identified using a method and/or assay system described herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or by inhalation, e.g., as an aerosol. The particular mode selected will depend, of course, upon the particular compound selected, the particular condition being treated and the dosage required for therapeutic efficacy. The methods of this invention, generally speaking, may be practiced using any mode of administration that is medically or veterinarily acceptable, meaning any mode that produces acceptable levels of efficacy without causing clinically unacceptable (e.g., medically or veterinarily unacceptable) adverse effects. Suitable preparations, e.g., substantially pure preparations, of one or more compound(s) may be combined with one or more pharmaceutically acceptable carriers or excipients, etc., to produce an appropriate pharmaceutical composition suitable for administration to a subject. Such pharmaceutically acceptable compositions are an aspect of the invention. The term "pharmaceutically acceptable carrier or excipient" refers to a carrier (which term encompasses carriers, media, diluents, solvents, vehicles, etc.) or excipient which does not significantly interfere with the biological activity or effectiveness of the active ingredient(s) of a composition and which is not excessively toxic to the host at the concentrations at which it is used or administered. Other pharmaceutically acceptable ingredients can be present in the composition as well. Suitable substances and their use for the formulation of pharmaceutically active compounds are well-known in the art (see, for example, "Remington's Pharmaceutical Sciences", E. W. Martin, 19th Ed., 1995, Mack Publishing Co.: Easton, Pa., and more recent editions or versions thereof, such as Remington: The Science and Practice of Pharmacy. 21st Edition. Philadelphia, Pa. Lippincott Williams & Wilkins, 2005, for additional discussion of pharmaceutically acceptable substances and methods of preparing pharmaceutical compositions of various types). Furthermore, compounds and compositions of the invention may be used in combination with any compound or composition used in the art for treatment of a particular disease or condition of interest.

A pharmaceutical composition is typically formulated to be compatible with its intended route of administration. For example, preparations for parenteral administration include sterile aqueous or non-aqueous solutions, suspensions, and emulsions. Aqueous carriers include water, alcoholic/aqueous solutions, emulsions or suspensions, including saline and buffered media, e.g., sodium chloride solution, Ringer's dextrose, dextrose and sodium chloride, lactated Ringer's. Examples of non-aqueous solvents are propylene glycol, polyethylene glycol, vegetable oils such as olive oil, and injectable organic esters such as ethyl oleate. fixed oils, polyethylene glycols, glycerine, propylene glycol or other synthetic solvents; preservatives, e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. pH can be adjusted with acids or bases, such as hydrochloric acid or sodium hydroxide. Such parenteral preparations can be enclosed in ampoules, disposable syringes or multiple dose vials made of glass or plastic.

For oral administration, compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like. Suitable excipients for oral dosage forms are, e.g., fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP).

For administration by inhalation, inventive compositions may be delivered in the form of an aerosol spray from a pressured container or dispenser which contains a suitable propellant, e.g., a gas such as carbon dioxide, a fluorocarbon, or a nebulizer. Liquid or dry aerosol (e.g., dry powders, large porous particles, etc.) can be used. The present invention also contemplates delivery of compositions using a nasal spray or other forms of nasal administration.

For topical applications, pharmaceutical compositions may be formulated in a suitable ointment, lotion, gel, or cream containing the active components suspended or dissolved in one or more pharmaceutically acceptable carriers suitable for use in such comporisition.

For local delivery to the eye, the pharmaceutically acceptable compositions may be formulated as solutions or micronized suspensions in isotonic, pH adjusted sterile saline, e.g., for use in eye drops, or in an ointment, or for intra-ocularly administration, e.g., by injection.

Pharmaceutical compositions may be formulated for transmucosal or transdermal delivery. For transmucosal or transdermal administration, penetrants appropriate to the barrier to be permeated may be used in the formulation. Such penetrants are generally known in the art. Inventive pharmaceutical compositions may be formulated as suppositories (e.g., with conventional suppository bases such as cocoa butter and other glycerides) or as retention enemas for rectal delivery.

In some embodiments, a composition includes one or more agents intended to protect the active agent(s) against rapid elimination from the body, such as a controlled release formulation, implants, microencapsulated delivery system, etc. Compositions may incorporate agents to improve stability (e.g., in the gastrointestinal tract or bloodstream) and/or to enhance absorption. Compounds may be encapsulated or incorporated into particles, e.g., microparticles or nanoparticles. Biodegradable, biocompatible polymers can be used, such as ethylene vinyl acetate, polyanhydrides, polyglycolic acid, PLGA, collagen, polyorthoesters, polyethers, and polylactic acid. Methods for preparation of such formulations will be apparent to those skilled in the art. For example, and without limitation, a number of particle, lipid, and/or polymer-based delivery systems are known in the art for delivery of siRNA. The invention contemplates use of such compositions. Liposomes or other lipid-based particles can also be used as pharmaceutically acceptable carriers.

Pharmaceutical compositions and compounds for use in such compositions may be manufactured under conditions that meet standards, criteria, or guidelines prescribed by a regulatory agency. For example, such compositions and compounds may be manufactured according to Good Manufacturing Practices (GMP) and/or subjected to quality control procedures appropriate for pharmaceutical agents to be administered to humans and can be provided with a label approved by a government regulatory agency responsible for regulating pharmaceutical, surgical, or other therapeutically useful products.

Pharmaceutical compositions of the invention, when administered to a subject for treatment purposes, are preferably administered for a time and in an amount sufficient to treat the disease or condition for which they are administered. Therapeutic efficacy and toxicity of active agents can be assessed by standard pharmaceutical procedures in cell cultures or experimental animals. The data obtained from cell culture assays and animal studies can be used in formulating a range of dosages suitable for use in humans or other subjects. Different doses for human administration can be further tested in clinical trials in humans as known in the art. The dose used may be the maximum tolerated dose or a lower dose. A therapeutically effective dose of an active agent in a pharmaceutical composition may be within a range of about 0.001 mg/kg to about 100 mg/kg body weight, about 0.01 to about 25 mg/kg body weight, about 0.1 to about 20 mg/kg body weight, about 1 to about 10 mg/kg. Other exemplary doses include, for example, about 1 µg/kg to about 500 mg/kg, about 100 µg/kg to about 5 mg/kg. In some embodiments a single dose is administered while in other embodiments multiple doses are administered. Those of ordinary skill in the art will appreciate that appropriate doses in any particular circumstance depend upon the potency of the agent(s) utilized, and may optionally be tailored to the particular recipient. The specific dose level for a subject may depend upon a variety of factors including the activity of the specific agent(s) employed, the particular disease or condition and its severity, the age, body weight, general health of the subject, etc. It may be desirable to formulate pharmaceutical compositions, particularly those for oral or parenteral compositions, in unit dosage form for ease of administration and uniformity of dosage. Unit dosage form, as that term is used herein, refers to physically discrete units suited as unitary dosages for the subject to be treated; each unit containing a predetermined quantity of active agent(s) calculated to produce the desired therapeutic effect in association with an appropriate pharmaceutically acceptable carrier. It will be understood that a therapeutic regimen may include administration of multiple doses, e.g., unit dosage forms, over a period of time, which can extend over days, weeks, months, or years. A subject may receive one or more doses a day, or may receive doses every other day or less frequently, within a treatment period. For example, administration may be biweekly, weekly, etc. Administration may continue, for example, until appropriate structure and/or function of a tissue or organ has been at least partially restored and/or until continued administration of the compound does not appear to promote further regeneration or improvement. In some embodiments, a subject administers one or more doses of a composition of the invention to him or herself.

In some embodiments, two or more compounds or compositions are administered in combination, e.g., for purposes of enhancing regeneration. Compounds or compositions administered in combination may be administered together in the same composition, or separately. In some embodiments, administration "in combination" means, with respect to administration of first and second compounds or compositions, administration performed such that (i) a dose of the second compound is administered before more than 90% of the most recently administered dose of the first agent has been metabolized to an inactive form or excreted from the body; or (ii) doses of the first and second compound are administered within 48, 72, 96, 120, or 168 hours of each other, or (iii) the agents are administered during overlapping time periods (e.g., by continuous or intermittent infusion); or (iv) any combination of the foregoing. In some embodiments, two or more NOTUM modulators, e.g., NOTUM inhibitors, are administered. In some embodiments, a NOTUM modulator, e.g., NOTUM inhibitor, is administered in combination with a Wnt ligand, e.g., any of human WNT1, WNT2, WNT2B, WNT3, WNT3A WNT4, WNT5A, WNT5B, WNT6, WNT7A, WNT7B, WNT8A, WNT8B, WNT9A, WNT9B, WNT10A WNT10B, WNT11, WNT16, or non-human homologs thereof. In some embodiments a NOTUM modulator, e.g., a NOTUM inhibitor, is administered in combination with a soluble glypican. In some embodiments, a NOTUM modulator, e.g., NOTUM inhibitor, is administered in combination with one or more growth factors, growth factor receptor ligands (e.g., agonists), hormones (e.g., steroid or peptide hormones), or signaling molecules, useful to promote regeneration. In some embodiments, a growth factor is an epidermal growth factor family member (e.g., EGF, a neuregulin), a fibroblast growth factor (e.g., any of FGF1-FGF23), a hepatocyte growth factor (HGF), a nerve growth factor, a bone morphogenetic protein (e.g., any of BMP1-BMP), a vascular endothelial growth factor (VEGF), etc.

EXAMPLES

Example 1

Notum is Induced by Wounding and Promotes Proper Regeneration

A central but poorly understood feature of regeneration in animals is the restoration of appropriate missing structures. Injuries occur in unpredictable ways, so that regenerating animals must employ robust mechanisms to re-establish proper tissue pattern after wounding. However, the mechanisms that explain restoration of pattern after injury are unknown. Planarians are freshwater flatworms that dramatically illustrate this phenomenon, as they can regenerate from nearly any type of injury despite possessing a complex anatomy (1).

The head-versus-tail regeneration decision in planarian flatworms is a striking example of pattern re-establishment through regeneration. Planarians regenerate a head from any anterior-facing amputation removing the head, and a tail from any posterior-facing amputation removing the tail; this property is known as regeneration polarity (2, 3). Wnt signaling controls the head-versus-tail regeneration decision, with beta-catenin-1 (4-6) and wnt1 (formerly known as wntP-1) (7-9) required to prevent head regeneration and promote tail regeneration at posterior-facing wounds. Overactivation of Wnt signaling by RNAi of the APC gene, which encodes an intracellular inhibitor of beta-catenin, resulted in tail regeneration at anterior-facing wounds, indicating that activation of Wnt signaling targets at anterior-facing wounds is sufficient to lead to tail formation (5). These observations suggest a switch-like behavior for the regeneration polarity decision, with high beta-catenin activity resulting in tail formation and low beta-catenin activity resulting in head formation. wnt1 function is required after wounding to establish posterior blastema polarity and wnt1 is induced to be expressed rapidly following wounding (7). Surprisingly, wnt1 expression is upregulated near both anterior- and posterior-facing wounds (7, 9, 10). Therefore, how wnt1 and beta-catenin act to promote tail formation only at appropriate wounds has remained unknown.

Figures 9A, 9B, 9C:
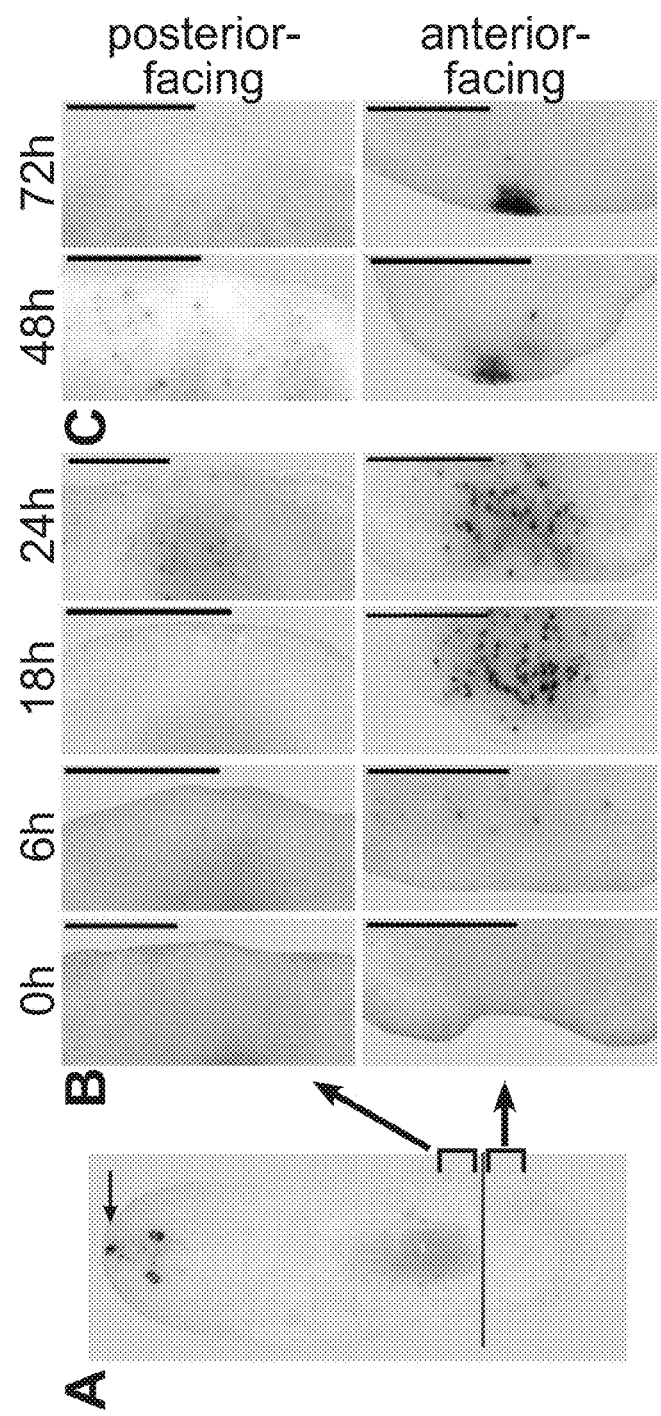
FIGS. 9A, 9B and 9C demonstrate that notum is expressed at anterior-facing wounds. (A-C) notum in situ hybridizations in intact animals (A) and in regenerating trunk and tail fragments (B, C) at time points (h) after amputation. Brackets, magnified regions at anterior- or posterior-facing wounds as indicated. Anterior, left (B-C) or top (A). Ventral view (all panels except 72 h), or dorsal view (72 h). Scale bars 200 microns.

We therefore sought to identify secreted inhibitors of Wnt signaling that might act at anterior-facing wounds, thereby promoting head regeneration. We identified a planarian homolog of *Drosophila* notum, and named the gene Smednotum (FIG. 8). In intact planarians, notum expression was detected prominently at the anterior pole (FIG. 1A). wnt1, by contrast, is expressed in intact planarians oppositely, at the posterior pole (4, 7). To determine whether notum is dynamically expressed during regeneration, we detected notum mRNA by in situ hybridization with a notum RNA probe in a series of regenerating fragments fixed at several times after head and tail amputation. At early times following amputation (6-24 hours, h), notum expression was observed to be highly upregulated in disperse cells preferentially near anterior-facing wounds and not posterior-facing wounds (FIG. 1B, FIG. 9). Low levels of expression were also detected at posterior-facing wounds initiated at later timepoints than the anterior-facing expression. At later times following wounding, anterior expression of notum coalesced to the new anterior pole while expression at posterior-facing wounds remained low (FIG. 1C, FIG. 9). These results indicate that wounding induces notum expression preferentially near anterior-facing wounds.

To test whether anterior-facing, wound-specific, notum expression is induced only as a response to head amputation, we performed incisions into the sides of animals. These small incisions were allowed to seal, and did not remove a fragment of the body. Strikingly, notum expression was detected on the anterior-facing, but not the posterior-facing, side of these incisions (FIG. 1D). Therefore, asymmetric notum expression following wounding does not require the loss of large tissue regions or loss of the anterior pole. In animals in which an oblique triangle of tissue was removed such that the sealed injury site involved a wound running diagonally to the main body axis, notum expression was observed throughout the anterior-facing side of the wound, indicating notum is not simply activated at wounds in a region perpendicular to the head-tail axis, but rather on the anterior-facing side of many types of wounds (FIG. 1D). Additionally, anterior-facing notum expression at side incisions was independent of the presence of the anterior or posterior poles of the animal, indicating that the polarity of notum expression is not controlled by signals from the poles, but in contrast, locally (FIG. 1D). These results indicate that wounding elicits notum expression in a manner that depends on orientation of a wound edge with respect to local tissue direction.

In principle, posterior-facing wounds could be non-permissive for high levels of notum expression, and/or anterior-facing wounds could be specifically instructive for notum expression. We therefore asked whether notum would be expressed between two closely opposed wound sites—with the tissue flanked by both an anterior-facing and a posterior-facing wound edge. In such animals, regions neighboring a wound to the anterior had a greater number of notum-expressing cells than did regions that bordered both anterior- and posterior-facing wounds (FIG. 1E). These data suggest that posterior-facing wounds suppress expression of notum presenting an environment that is less permissive for notum activation. notum expression at the anterior pole in intact animals and at anterior-facing wounds was detected in sub-epidermal cells (FIG. 1F) that resembled in size and location the cells expressing wnt1 near wounds (7). Indeed, notum and wnt1 were coexpressed in some cells at anterior-facing wounds (FIG. 1G).

Example 2

Notum Expression is Required for Regeneration Polarity after Wounding

Figures 2A, 2B, 2C, 2D, 2E, 2F, 2G:
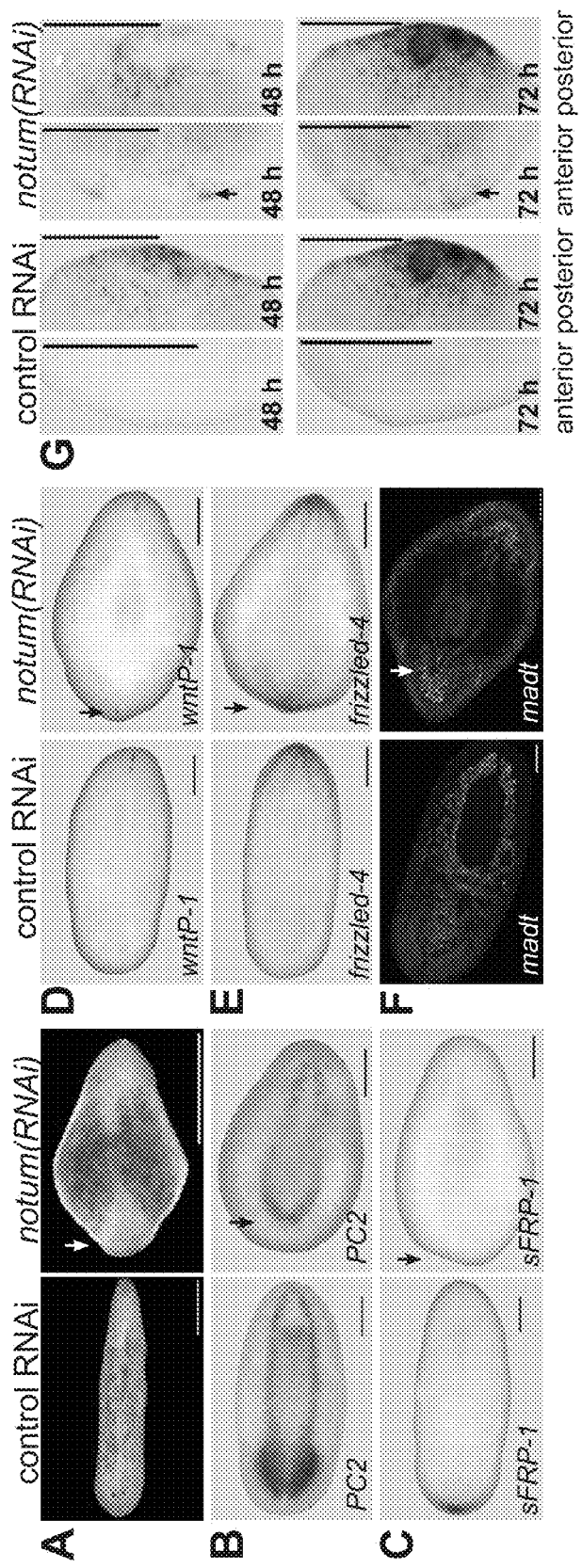
FIGS. 2A, 2B, 2C, 2D, 2E, 2F and 2G demonstrate that notum is required for head-tail regeneration polarity. (A) Animals were injected with control or notum dsRNA for two days prior to amputation of a prepharyngeal transverse fragment and allowed to regenerate for 14 days. Control fragments regenerated normally (100%, n=101) whereas notum (RNAi) fragments failed to regenerate a head (47%, n=133). (B-F) In situ hybridizations of control or notum(RNAi) regenerating animals fixed 14 days after amputation and probed for expression of (B) PC2 (CNS marker), (C) sFRP-1 (anterior pole marker), (D) wnt1 and (E) fzd-4 (posterior markers), and (F) madt (gut marker) as indicated. Arrows indicate lack of anterior marker expression (B-C), presence of posterior marker expression (D-E), or presence of posterior gut morphology (F), in notum(RNAi) animals. Images are representatives: PC2-stained notum(RNAi), 9 of 11 animals; wnt1-stained notum(RNAi), 8 of 25 animals; fzd-4-stained notum(RNAi), 7 of 24 animals; madt-stained notum(RNAi), 11 of 38 animals; other panels ≥7 of 7 animals. (G) Regenerating fragments were fixed at 48 hours or 72 hours following amputation and probed for wntP-2 expression by in situ hybridization. wntP-2 has been proposed to be a member of the Wnt11 subfamily of Wnt genes (9). Top panel shows the anterior-facing wound, A, and the bottom panel shows the posterior-facing wound, P, for each treatment. Arrows indicate wntP-2 expression at anterior-facing wounds in notum (RNAi) animals. Images are representatives depicting ≥5 of 6 animals for each panel. Anterior, left (A-F), or top (G-H). Scale bars, 500 microns (top left), 100 microns (madt-probed animals), or 200 microns (all others).
Figures 10A, 10B, 10C:
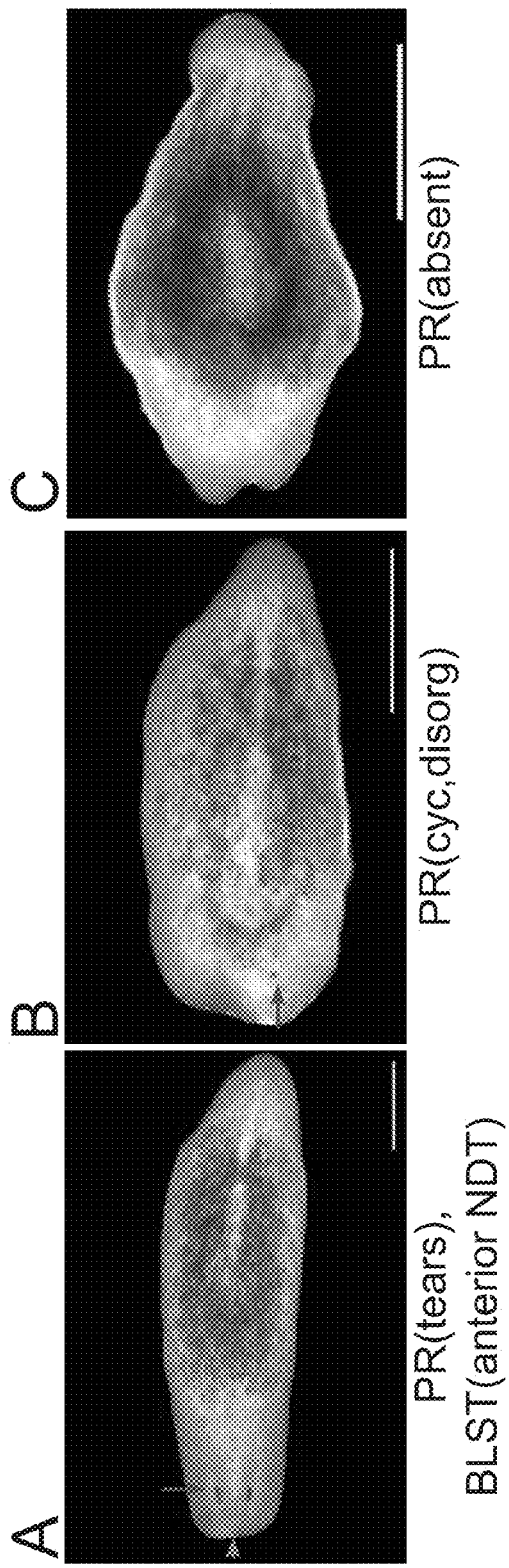
FIGS. 10A, 10B and 10C demonstrate the range of defects during anterior regeneration in notum(RNAi) animals. Transversely amputated prepharyngeal fragments were injected with 13×3 nl notum dsRNA 1 hour and 3 hours after surgery and allowed to regenerate. Animals regenerated with a range of anterior defects: (A) regeneration of two elongated photoreceptors (red arrow) and indented anterior blastema (green arrowhead), (B) regeneration of a single photoreceptor which was located medially or elsewhere along the mediolateral axis (shown, red arrow), (C) regeneration of an anterior blastema that lacked photoreceptors. Diluting the notum dsRNA with control dsRNA decreased the penetrance of the PR(absent) phenotype (as shown in C) and increased the penetrance of one or two photoreceptors (as shown in A and B) observed in notum(RNAi) animals (notum(RNAi): 82% PR(absent), 18% PR(cyc or abnormal), 0% normal, n=11; compare to notum (RNAi); control(RNAi): 13% PR(absent), 67% PR(cyc or abnormal), 20% normal, n=15). Therefore, we interpret the PR(absent) phenotype to be the strongest notum(RNAi) phenotype.

The specificity of high levels of notum expression for anterior-facing wounds suggested that this gene might function in the control of regeneration polarity, so we inhibited notum by RNA interference (RNAi) and assayed for defects in head and tail regeneration. notum(RNAi) animals regenerated a posterior-facing tail apparently normally, but failed to regenerate an anterior-facing head with photoreceptors (47%, n=113) (FIG. 2A). Decapitated notum(RNAi) animals that succeeded in regenerating at least one photoreceptor did so aberrantly (53%, n=113; see FIG. 10); such phenotypes may reflect a weakly expressive version of the notum(RNAi) phenotype (FIG. 10). Control RNAi animal fragments regenerated normally (100%, n=101). These data demonstrate that notum is required for head regeneration. To characterize the nature of notum(RNAi) anterior blastemas that lack photoreceptors, we assessed for expression of a variety of axial markers with RNA probes (FIG. 2A). The anterior blastema of notum(R-NAi) animals lacked a clear cephalic ganglia or expression of a marker of the anterior pole (sFRP-1) (FIGS. 2B-C). By contrast, notum(RNAi) anterior blastemas expressed the posterior markers wnt1 and frizzled-4 (FIGS. 2D-E). Furthermore, notum(RNAi) animals regenerated an anterior gut with the posterior-specific morphology of two rather than one main branches (FIG. 2F). We conclude that notum inhibition causes regeneration of an anterior-facing tail.

Figure 11:
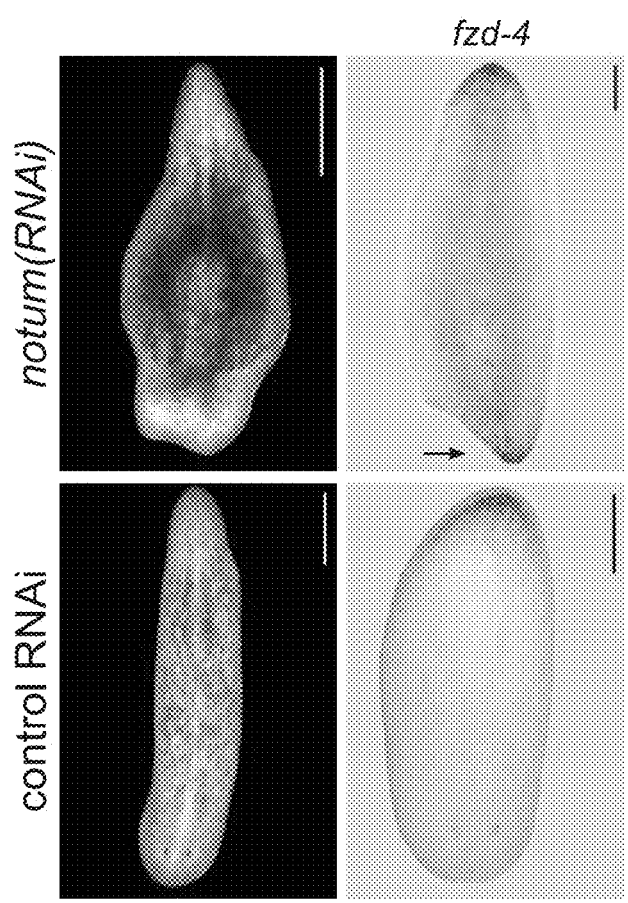
FIG. 11 demonstrates that regeneration polarity requires wound-induced expression of notum. Freshly amputated prepharygeal transverse fragments were injected with control or notum dsRNA twice and allowed to regenerate for 15 days. (Upper) Control fragments regenerated normally (100%, n=6) whereas notum(RNAi) fragments failed to regenerate two photoreceptors (23%, n=22). (Lower) In situ hybridizations of control or notum(RNAi) animals probed for fzd-4 expression. Images are representatives: control RNAi, 5 of 5 animals; notum RNAi, 8 of 12 animals. Scale bars, 200 microns.
Figure 12:
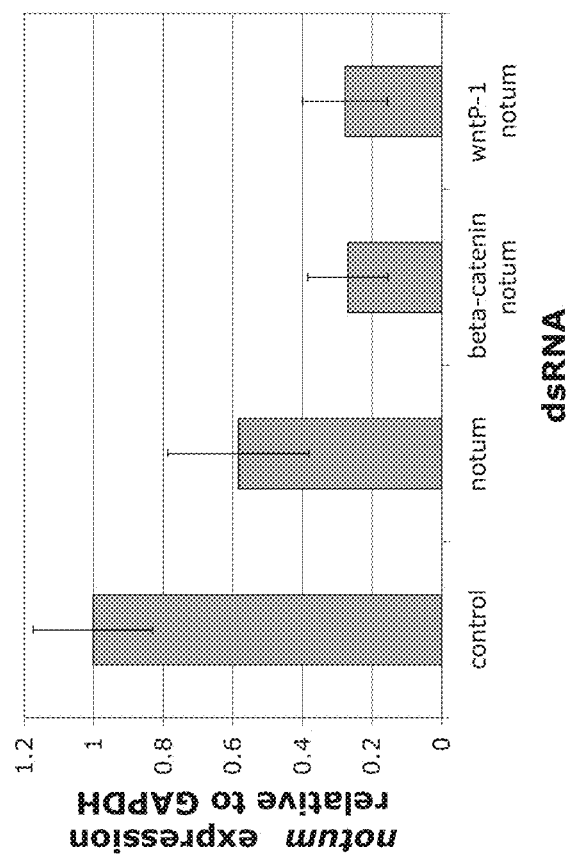
FIG. 12 illustrates quantitation of notum mRNA in epistasis tests with beta-catenin-1 and wnt1. Total RNA was prepared from 18-hour regenerating fragments prepared as in FIG. 3A and subjected to realtime PCR analysis to quantitate notum mRNA versus a GAPDH control. Values show means of three biological replicates; error bars are standard-deviations.

Because notum mRNA is expressed at the anterior pole of intact animals and also near anterior-facing wounds, we sought to determine whether wound-induced notum expression contributes to regeneration polarity. Previous work showed that there is a requirement for beta-catenin-1 (4) and wnt1 (7) after wounding for caudal blastema regeneration. To test for a role for notum after injury, freshly amputated wild-type planarian fragments were injected with notum dsRNA and scored for polarity defects after several days of regeneration. These RNAi animals also displayed a reversal in regeneration polarity (FIG. 11), similar to animals in which notum had been inhibited for three days prior to amputation (FIGS. 2A, E). We cannot exclude a possible additional role in regeneration polarity of NOTUM protein present in intact animals prior to amputation; however, these data indicate that there is a requirement for new expression of notum following wounding.

wntP-2 expression is upregulated following wounding at posterior- and not anterior-facing wounds, and this process requires wnt1 and beta-catenin-1 (7). Therefore, selective wntP-2 expression at posterior-facing wounds reflects an early readout (i.e., prior to significant tissue formation) of wnt1 and beta-catenin-mediated polarity specification. notum(RNAi) fragments expressed wntP-2 ectopically at anterior-facing wounds by 48 hours after wounding (FIGS. 2G-H). Therefore, new expression of notum mRNA following wounding acts to promote polarity at anterior-facing wounds and is required to prevent the activation of beta-catenin targets that are normally specific to posterior-facing wounds.

Example 3

Notum does not Appear to Act Via Hedgehog Signaling in Regeneration Polarity

Figures 14A, 14B:
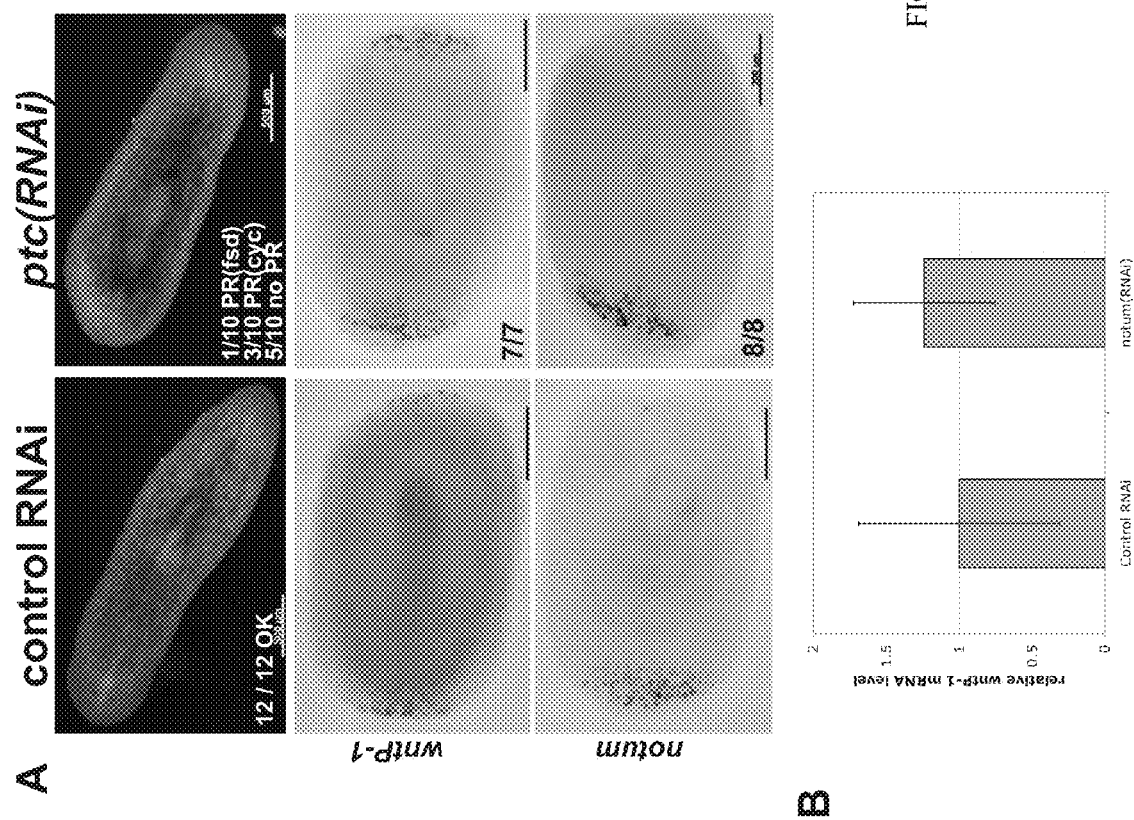
FIGS. 14A and 14B demonstrate that patched RNAi results in tail regeneration without affecting notum expression. (A) Animals were administered control or patched dsRNA for three days prior to amputation of heads and tails, and either fixed at 18-hours or allowed to regenerate for 14 days and scored for regeneration defects. Regenerated patched(RNAi) animals displayed a range of defects (50% PR(absent), 30% PR(cyc), 10% PR(fsd), n=10) by 12 days after amputation. Additionally, patched(RNAi) animals had excess wnt1 expression at 18 hours of regeneration (100%, n=7), as reported. However, notum expression at 18 hours appeared normal, as it was highly expressed at anterior-facing wounds but weakly expressed or absent at posterior-facing wounds (100%, n=8). (B) Animals were administered control or notum dsRNA for three days prior to amputation of a prepharyngeal transverse fragment. Total RNA was prepared from 18-hour regenerating fragments and from three biological replicates of wnt1 mRNA versus a GAPDH control. Values show means of three biological replicates normalized such that the control dsRNA treated samples have a wnt1-to-GAPDH abundance ratio of 1; error bars are standard-deviations.

Overactivation of Hedgehog signaling in planarians, by inhibition of Smed-patched, can result in anterior tail regeneration (10, 17). This likely involves an increase in wnt1 expression at anterior- and posterior-facing amputation sites in patched(RNAi) animals (10, 17). Because patched and notum inhibition had similar effects on regeneration polarity, we tested the possibility that patched functions in regeneration polarity to promote notum expression at anterior-facing wounds. patched(RNAi) animals regenerated anterior tails (3/10 animals) and had elevated wnt1 levels at anterior- and posterior-facing wounds in 18-hour regenerating fragments (7/7 animals) (FIG. 14A). However, notum expression was apparently normal near anterior- and posterior-facing wounds in 18-hour regenerating fragments taken from the same cohort (8/8 animals, FIG. 14A). Therefore, patched likely does not function in regeneration polarity to drive the asymmetric expression of notum at anterior- versus posterior-facing wounds. Additionally, mutations in notum can affect Hedgehog signaling in *Drosophila* (18). Therefore, in principle, notum could act in regeneration polarity either by regulating Hedgehog signaling or Wnt signaling. Inhibition of Hedgehog signaling causes a reduction in wound-induced wnt1 expression whereas overactivation of Hedgehog signaling causes excess wnt1 expression after wounding (10). Using realtime PCR, we could not detect any difference in wnt1 expression between notum(RNAi) and control RNAi regenerating fragments at 18 hours after amputation (FIG. 14B). Taken together, these results suggest that in regeneration polarity, Hedgehog signaling does not control notum expression and that notum does not act by modulating Hedgehog signaling.

Example 4

Notum Acts as Feedback Inhibitor of Wnt Signaling in Regeneration

Figures 3A, 3B, 3C:
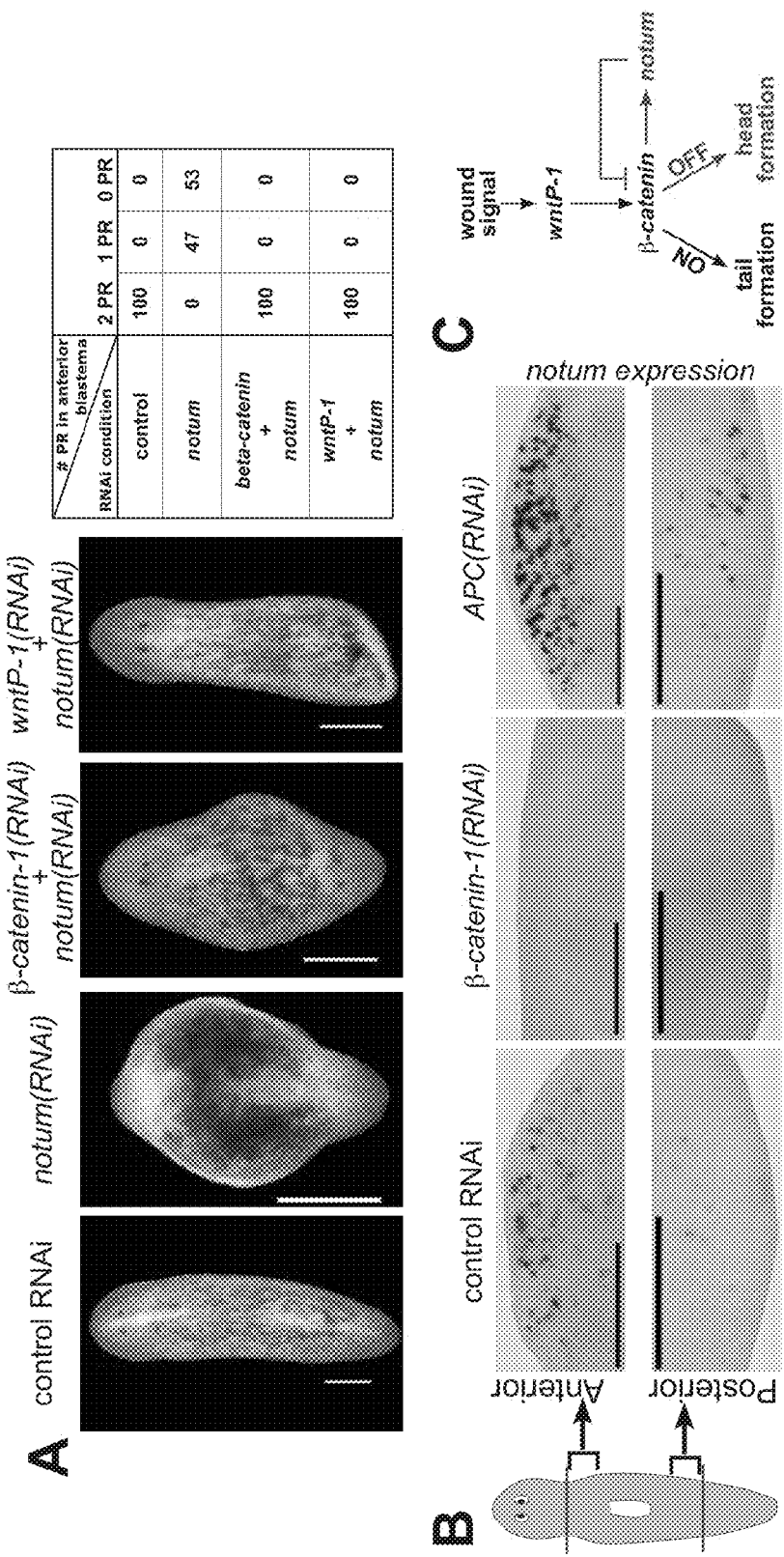
FIGS. 3A, 3B and 3C demonstrate that notum is a Wnt signaling-dependent Wnt inhibitor that controls regeneration polarity. (A) Epistasis test between notum and Wnt signaling components. Animals were injected with control dsRNA, notum dsRNA, or a mixture of beta-catenin-1, wnt1, and notum dsRNA for two days prior to amputation of prepharyngeal transverse fragments and scored after 10 days of regeneration. Chart shows scoring of animals as percentages. wnt1 RNAi can cause a failure of tail regeneration and/or head regeneration at posterior-facing wounds (7-9). Without wishing to be bound by any theory, the observation of tail regeneration failure rather than head regeneration at the posterior-facing wounds in wnt1(RNAi); notum(RNAi) animals is likely due to a reduction in wnt1 RNAi efficacy by competition from the notum dsRNA. (B) Animals were fed bacteria expressing control, beta-catenin-1, or APC dsRNA for 21 days prior to amputation of heads and tails, fixed 18 hours after surgery, and probed for notum expression by in situ hybridization. Brackets show region near anterior or posterior-facing wound as indicated. Images are representatives. Number of notum-expressing cells at anterior-facing wounds: control animals, 102+/−17 cells; beta-catenin-1 (RNAi) animals, 17+/−23 cells (p=6.5×10$^{-8}$); APC(RNAi) animals, 186+/−37 cells (p=8.1×10$^{-6}$). Number of notum-expressing cells at posterior-facing wounds: control animals, 9+/−5 cells; beta-catenin-1 (RNAi) animals, 1+/−3 cells (p=0.003); APC(RNAi) animals, 30+/−24 cells (p=0.014). Errors are standard deviations and p-values are calculated from a 2-tailed T-test. Anterior top (A), or left (B). Scale bars, 200 microns.
Figure 4:
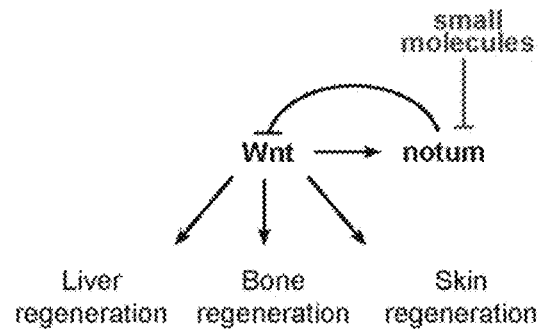
FIG. 4 illustrates therapeutic uses for an inhibitor of NOTUM. Wnt signaling through β-catenin causes expression of NOTUM, which in turn attenuates Wnt signaling. Small molecules inhibiting NOTUM (red) would be expected to upregulate Wnt signaling specifically at cell types and sites at which Wnt signaling is normally engaged, such as liver, bone and skin.

The polarity transformation in notum(RNAi) animals is similar to the phenotype caused by inhibition of APC, which encodes an intracellular inhibitor of beta-catenin protein (5). Additionally, notum in *Drosophila* acts to inhibit Wnt signaling in imaginal discs (11, 12). Therefore, we performed double RNAi experiments to assess the candidate pathway of action involving notum, beta-catenin-1, and wnt1. Double RNAi of beta-catenin-1 and notum resulted in a polarity phenotype identical to that caused by inhibition of beta-catenin-1 alone—regeneration of an anterior- and a posterior-facing head (FIG. 3A). Similarly, inhibition of wnt1 suppressed the polarity phenotype caused by notum RNAi (FIG. 3A). The efficiency of notum RNAi was not reduced in the double RNAi animals (Figure S5), which verified that suppression of the notum phenotype by wnt1 and beta-catenin-1 dsRNA is unlikely to be simply due to competition with notum dsRNA for RNAi. These data suggest that the notum(RNAi) phenotype requires the action of wnt1 and beta-catenin genes and support a model in which notum normally inhibits wnt1 and beta-catenin-1 function to allow regeneration of a head at anterior-facing wounds.

Figures 13A, 13B, 13C:
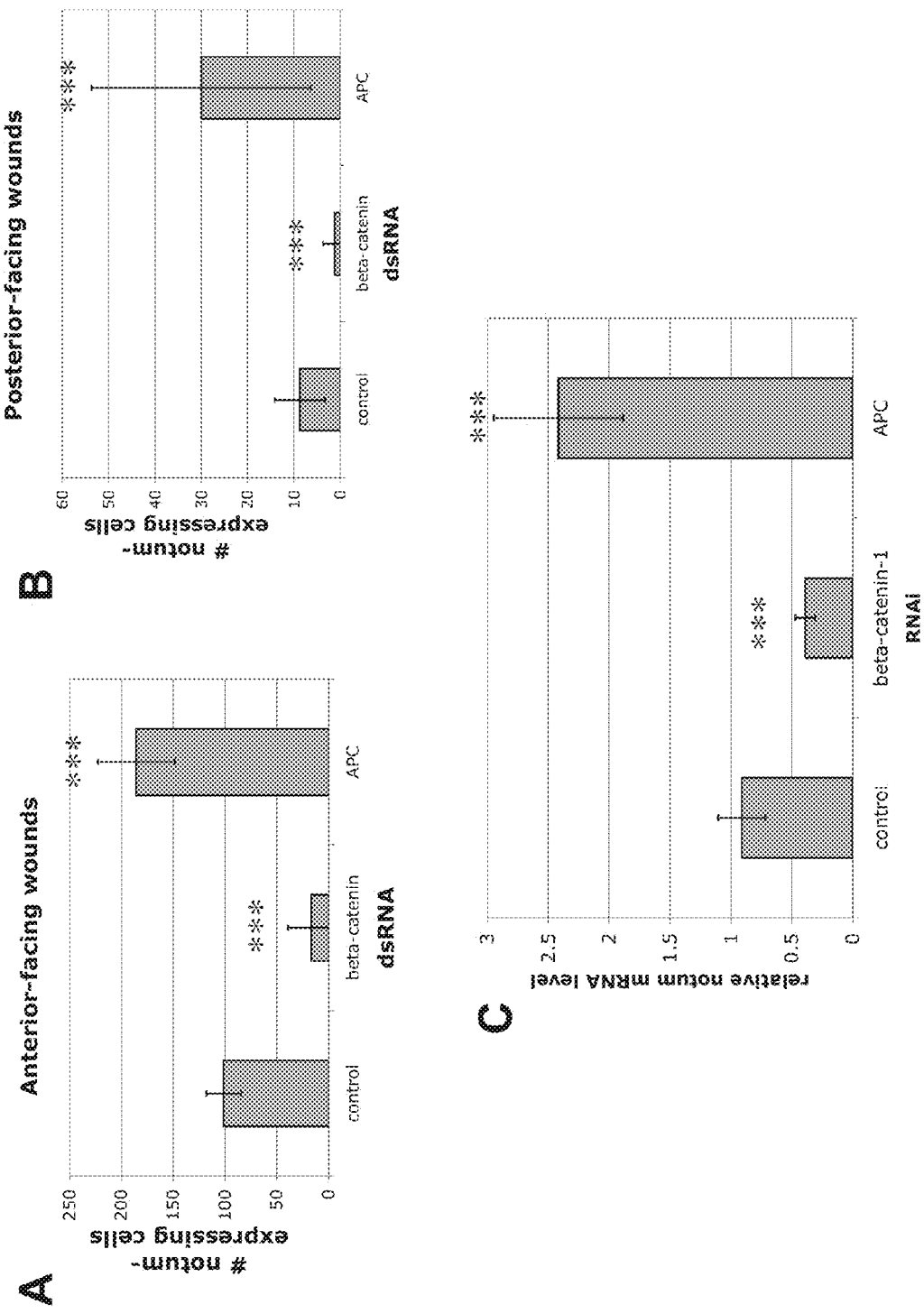
FIGS. 13A, 13B and 13C demonstrate that Wnt signaling is necessary and sufficient for wound-induced notum expression. (A, B) Quantitation of experiment shown in FIG. 4A. Animals were fed bacteria expressing control, wnt1, beta-catenin-1, or APC dsRNA for 21 days prior to amputation of heads and tails, fixed 18 hours after surgery, and probed for notum expression by in situ hybridization. Fixed fragments were scored for their number of notum-expressing cells on the ventral surface near the anterior- (A) or posterior-facing (B) wounds. Values show means of ≥9 animals examined for each condition, and error bars show standard deviations. (C) Quantitation of notum mRNA versus gapdh mRNA control by realtime PCR. Values shown are means of total RNA extracted from 8 individual trunk fragments prepared as described in (A,B) above. Error bars are standard deviations. p-values, two-tailed T-test (*, $p<0.05$; , $p<0.01$; *, $p<0.001$).

We tested the influence of Wnt signaling on notum expression in planarians. Inhibition of beta-catenin-1 caused a robust reduction of notum expression (FIGS. 3B, 13A, 13C). There existed very few notum-expressing cells near both anterior- and posterior-facing wounds of beta-catenin(RNAi) animals. Conversely, inhibition of APC caused an upregulation of notum expression near wounds (FIGS. 3B, 13B, 13C). Therefore, Wnt signaling is necessary and can be sufficient at wound sites for notum expression. Perturbation of Wnt signaling impacted the number of notum-expressing cells regardless of the direction the wound faced (FIGS. 13A-13B), so we propose that some other process might normally ensure an asymmetric notum expression at anterior- versus posterior-facing wounds. Because Smed-notum acts to inhibit beta-catenin-1 and requires beta-catenin-1 for its effects, these results suggest that regulation of feedback inhibition controls the regeneration polarity decision (FIG. 3C).

Development of the primary body axis involves anterior inhibition of Wnt signaling in many animals and developmental contexts (22). For example, anterior inhibition of Wnt signaling by Dickkopf is required for head formation in *Xenopus* (23). notum acts as a Wnt signaling inhibitor in *Drosophila* development (11, 12). notum is an ancient gene present in cnidarians and bilaterians (Fig S1). Human Notum can cause cleavage of GPI-anchored proteins in cultured mammalian cells (13), and *Drosophila* notum signals through the GPI-anchored glypican family of cell surface Heparan Sulfate Proteoglycans (HSPGs) (12, 14, 15). Wnt signaling is used broadly in regeneration (24-28). Our results suggest that cleavage of glypicans by Notum proteins can be an important determinant of the outcome of Wnt expression in regeneration.

REFERENCES

1. P. W. Reddien, A. Sánchez Alvarado, *Ann. Rev. Cell Dev. Bio.* 20, 725-57 (2004).
2. T. H. Morgan, *Arch. Entw. Mech. Org.* 7, 364-397 (1898).
3. T. H. Morgan, *J. Exp. Zool.* 2, 495-506 (1905).
4. C. P. Petersen, P. W. Reddien, *Science* 319, 327-30 (Jan. 18, 2008).
5. K. A. Gurley, J. C. Rink, A. Sánchez Alvarado, *Science* 319, 323-7 (Jan. 18, 2008).
6. M. Iglesias, J. L. Gomez-Skarmeta, E. Saló, T. Adell, *Development* 135, 1215-21 (April 2008).
7. C. P. Petersen, P. W. Reddien, *Proc Natl Acad Sci USA* 106, 17061-6 (Oct. 6, 2009).
8. T. Adell, E. Saló, M. Boutros, K. Bartscherer, *Development* 136, 905-10 (March, 2009).
9. K. A. Gurley et al., *Dev Biol* 347, 24-39 (Nov. 1, 2010).
10. J. C. Rink, K. A. Gurley, S. A. Elliott, A. Sanchez Alvarado, *Science* 326, 1406-10 (Dec. 4, 2009).
11. O. Gerlitz, K. Basler, *Genes Dev* 16, 1055-9 (May 1, 2002).
12. A. J. Giraldez, R. R. Copley, S. M. Cohen, *Dev Cell* 2, 667-76 (May, 2002).
13. A. Traister, W. Shi, J. Filmus, *Biochem J* (Oct. 30, 2007).
14. C. Han, D. Yan, T. Y. Belenkaya, X. Lin, *Development* 132, 667-79 (February, 2005).
15. J. Kreuger, L. Perez, A. J. Giraldez, S. M. Cohen, *Dev Cell* 7, 503-12 (October, 2004).
16. D. Yan, X. Lin, *Cold Spring Harb Perspect Biol* 1, a002493 (September, 2009).
17. S. Yazawa, Y. Umesono, T. Hayashi, H. Tarui, K. Agata, *Proc Natl Acad Sci USA* 106, 22329-34 (Dec. 29, 2009).
18. K. L. Ayers, A. Gallet, L. Staccini-Lavenant, P. P. Therond, *Dev Cell* 18, 605-20 (Apr. 20, 2010).

19. Y. I. Liu et al., *Dev Biol* 323, 41-52 (Nov. 1, 2008).
20. M. V. Chang, J. L. Chang, A. Gangopadhyay, A. Shearer, K. M. Cadigan, *Curr Biol* 18, 1877-81 (Dec. 9, 2008).
21. Y. Torisu et al., *Cancer Sci* 99, 1139-46 (June, 2008).
22. C. P. Petersen, P. W. Reddien, *Cell* 139, 1056-68 (Dec. 11, 2009).
23. A. Glinka et al., *Nature* 391, 357-62 (Jan. 22, 1998).
24. H. Yokoyama, H. Ogino, C. L. Stoick-Cooper, R. M. Grainger, R. T. Moon, *Dev Biol* 306, 170-8 (Jun. 1, 2007).
25. C. L. Stoick-Cooper et al., *Development* 134, 479-89 (February, 2007).
26. W. Goessling et al., *Dev Biol* 320, 161-74 (Aug. 1, 2008).
27. G. Lin, J. M. Slack, *Dev Biol* 316, 323-35 (Apr. 15, 2008).
28. J. B. Kim et al., *J Bone Miner Res* 22, 1913-23 (December, 2007).
29. M. Golembo, R. Schweitzer, M. Freeman, B. Z. Shilo, *Development* 122, 223-30 (January, 1996).
30. M. Starz-Gaiano, M. Melani, X. Wang, H. Meinhardt, D. J. Montell, *Dev Cell* 14, 726-38 (May, 2008).
31. O. Brandman, T. Meyer, *Science* 322, 390-5 (Oct. 17, 2008).
32. H. K. MacWilliams, *Dev Biol* 96, 239-57 (March, 1983).
33. H. K. MacWilliams, *Dev Biol* 96, 217-38 (March, 1983).
34. M. Broun, H. R. Bode, *Development* 129, 875-84 (February, 2002).

Methods and Materials
Gene Sequences.

Smed-notum was identified by BLAST searches on an assembly of the *S. mediterranea* genome (available via the world wide web). 5' and 3' RACE was performed to identify the full-length sequence of Smed-notum using the FirstChoice RLM-Race kit (Ambion). Complete sequences for Smed-notum are being deposited with NCBI and are shown in FIG. 6. Unless otherwise noted, dsRNA and riboprobes were made from a 1969-bp fragment of notum (primers 5'-AAAATTTCTGAGGATCGAAAAA-3' (SEQ ID NO: 1), 5'-TGAAGCTAGATTTATGTGAAAAACCA-3' (SEQ ID NO: 2); nucleotides 43-2012). In FIGS. 3B-C, notum dsRNA was prepared from a 1438-bp fragment (primers 5'-TCGAGTGATTTGTGGTCTGG-3' (SEQ ID NO: 3), 5'-TGAAGCTAGATTTATGTGAAAAACCA-3' (SEQ ID NO: 4), nucleotides 575-2012). Unless otherwise noted, control dsRNA was synthesized from a 1527-bp fragment of Photinus pyralis luciferase from the pGL3-control vector (Promega) (primers 5'-TATCCGCTGGAAGATGGAAC-3 (SEQ ID NO: 5), 5'-CGGTACTTCGTCCACAAACA-3' (SEQ ID NO: 6)).

wntP-1 (1), wntP-2 (1), sFRP-1 (1), frizzled-4 (1), PC2 (1), and madt (2) riboprobes were described previously.

Fixations, In Situ Hybridizations, and Immunostainings

Fixations and in situ hybridizations were performed as described previously (3). Animals were killed in 5% N-acetyl-cysteine in 1×PBS for 5 minutes at room temperature followed by fixation in formaldehyde. Animals were bleached in 6% hydrogen peroxide overnight and stored in methanol. Digoxigenin- or fluorescein-labeled riboprobes were synthesized as previously described (4). NBT/BCIP colorimetric or fluorescence in situ hybridizations were performed as previously described (3). For double labeling, HRP-inactivation was performed between labelings in 4% formaldehyde.

RNAi

For RNAi by injection, dsRNA was prepared from in vitro transcription reactions (Promega) using PCR-generated templates with flanking T7 promoters, purified by phenol extraction and ethanol precipitation, and annealed after resuspension in water. Unless noted otherwise, intact animals were injected with 4×30 nL dsRNA on three consecutive days, amputated transversely to create a prepharyngeal fragment, and this fragment was injected with 2×13 nL dsRNA two hours after surgery. In FIG. 10, freshly amputated prepharyngeal transverse fragments were injected with 3×13 nL dsRNA 1 hour and 3 hours after surgery.

Realtime PCR

Notum mRNA was detected by realtime PCR using SYBR Green and quantified using the standard curve method. For FIG. 3C, total RNA was isolated from three biological replicates of three regenerating fragments each. For FIG. 10, total RNA was separately isolated from 8 individual prepharyngeal fragments. Total RNA was isolated by mechanical homogenization in Trizol (invitrogen). RNA samples were DNAse-treated using DNA-free (Ambion), and cDNA was synthesized using Superscript III reverse transcriptase (Invitrogen). Notum mRNA was detected with primers 5'-TATTTGGTTTTTATTCCAGGATCA-3' (SEQ ID NO: 7) and 5'-ATCCATTGATCTTCAATAGGCTCA-3'(SEQ ID NO: 8), and gapdh mRNA was detected with primers described previously (5).

REFERENCES FOR MATERIALS AND METHODS

1. C. P. Petersen, P. W. Reddien, *Proc Natl Acad Sci USA* 106, 17061-6 (Oct. 6, 2009).
2. D. Wenemoser, P. W. Reddien, *Dev Biol* 344, 979-91 (Aug. 15, 2010).
3. B. J. Pearson et al., *Dev Dyn* 238, 443-50 (February, 2009).
4. P. W. Reddien, N. J. Oviedo, J. R. Jennings, J. C. Jenkin, A. Sánchez Alvarado, *Science* 310, 1327-1330 (Nov. 25, 2005).
5. G. T. Eisenhoffer, H. Kang, A. Sánchez Alvarado, *Cell Stem Cell* 3, 327-39 (Sep. 11, 2008).

Those skilled in the art will recognize, or be able to ascertain using no more than routine experimentation, many equivalents to the specific embodiments of the invention described herein. The scope of the present invention is not intended to be limited to the Description or the details set forth therein. Articles such as "a", "an" and "the" may mean one or more than one unless indicated to the contrary or otherwise evident from the context. Certain of the inventive methods are often practiced using populations of cells, e.g., in vitro or in vivo. Thus references to "a cell" should be understood as including embodiments in which the cell is a member of a population of cells, e.g., a population comprising or consisting of cells that are substantially genetically identical. However, the invention encompasses embodiments in which inventive methods is/are applied to an individual cell. Thus, references to "cells" should be understood as including embodiments applicable to individual cells within a population of cells and embodiments applicable to individual isolated cells.

Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. It is contemplated that all embodiments described herein are applicable to all different aspects of the invention.

It is also contemplated that any of the embodiments can be freely combined with one or more other such embodiments whenever appropriate. Furthermore, it is to be understood that the invention encompasses all variations, combinations, and permutations in which one or more limitations, elements, clauses, descriptive terms, etc., from one or more of the claims (whether original or subsequently added claims) is introduced into another claim (whether original or subsequently added). For example, any claim that is dependent on another claim can be modified to include one or more elements or limitations found in any other claim that is dependent on the same base claim, and any claim that refers to an element present in a different claim can be modified to include one or more elements or limitations found in any other claim that is dependent on the same base claim as such claim. Furthermore, where the claims recite a composition, the invention provides methods of making the composition, e.g., according to methods disclosed herein, and methods of using the composition, e.g., for purposes disclosed herein. Where the claims recite a method, the invention provides compositions suitable for performing the method, and methods of making the composition. Also, where the claims recite a method of making a composition, the invention provides compositions made according to the inventive methods and methods of using the composition, unless otherwise indicated or unless one of ordinary skill in the art would recognize that a contradiction or inconsistency would arise. Where elements are presented as lists, e.g., in Markush group format, each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where phrases such as "less than X", "greater than X", or "at least X" is used (where X is a number or percentage), it should be understood that any reasonable value can be selected as the lower or upper limit of the range. It is also understood that where a list of numerical values is stated herein (whether or not prefaced by "at least"), the invention includes embodiments that relate to any intervening value or range defined by any two values in the list, and that the lowest value may be taken as a minimum and the greatest value may be taken as a maximum. Furthermore, where a list of numbers, e.g., percentages, is prefaced by "at least", the term applies to each number in the list. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% or in some embodiments 10% of a number in either direction (greater than or less than the number) unless otherwise stated or otherwise evident from the context (e.g., where such number would impermissibly exceed 100% of a possible value). A "composition" as used herein, can include one or more than one component unless otherwise indicated. For example, a "composition comprising a NOTUM inhibitor" can consist or consist essentially of a NOTUM inhibitor or can contain one or more additional components. It should be understood that, unless otherwise indicated, a NOTUM inhibitor (or other compound referred to herein) in any embodiment of the invention may be used or administered in a composition that comprises one or more additional components.

In addition, any particular embodiment(s), aspect(s), element(s), feature(s), etc., of the present invention, e.g., any compound, composition, cell type, cell line, reporter molecule, detectable moiety, subject, disease, etc., may be explicitly excluded.

We claim:

1. A method of identifying a candidate modulator of NOTUM activity comprising: (a) providing a composition comprising: (1) an isolated NOTUM polypeptide; (2) a reporter molecule comprising a GPI anchor and a detectable moiety; and (3) a test compound, wherein the reporter molecule is attached to a membrane via the GPI anchor; (b) maintaining the composition for a suitable time period; (c) and measuring the amount of detectable moiety released from the membrane during the time period, wherein release of a greater amount of detectable moiety than would occur in the absence of the test compound indicates that the test compound is a candidate enhancer of NOTUM activity, and release of a lower amount of the detectable moiety as compared with the amount that would occur in the absence of the test compound indicates that the test compound is a candidate inhibitor of NOTUM activity.

2. The method of claim 1, wherein the GPI anchor is a GPI anchor of a NOTUM substrate polypeptide.

3. The method of claim 1, wherein the GPI anchor is a vertebrate glypican GPI anchor.

4. The method of claim 1, wherein the GPI anchor is a vertebrate glypican 3 GPI anchor.

5. The method of claim 1, wherein the GPI anchor is a human glypican GPI anchor.

6. The method of claim 1, wherein the GPI anchor is a human glypican 3 GPI anchor.

7. The method of claim 1, wherein the reporter molecule is a fusion protein comprising at least a portion of a mature NOTUM substrate polypeptide, a GPI anchor of the mature NOTUM substrate polypeptide, and a detectable polypeptide.

8. The method of claim 1, wherein the reporter molecule comprises a fusion protein comprising a GPI anchor of a human glypican 3 polypeptide, at least a portion of a human glypican polypeptide, and a detectable polypeptide.

9. The method of claim 1, wherein the reporter molecule comprises a fusion protein comprising a GPI anchor of a human glypican 3 polypeptide, at least a portion of a human glypican 3 polypeptide, and a detectable polypeptide.

10. The method of claim 1, wherein the reporter molecule is a polypeptide, the composition comprises a cell that produces the polypeptide, and at least some of the polypeptide is attached to the cell membrane of the cell via the GPI anchor so that cleavage of the GPI anchor releases the detectable moiety from the cell.

11. The method of claim 10, wherein the cell is in a liquid medium and step (c) comprises detecting the detectable moiety released from the cell.

12. The method of claim 1, wherein the detectable moiety comprises a fluorescent polypeptide.

13. The method of claim 1, wherein the NOTUM polypeptide is a vertebrate NOTUM polypeptide.

14. The method of claim 1, wherein the NOTUM polypeptide is a human NOTUM polypeptide.

15. The method of claim 1, wherein the test compound is a small molecule.

16. The method of claim 1, comprising (i) comparing the amount of detectable moiety released from the membrane during the time period with a reference value; and (ii) determining whether the test compound is a candidate enhancer or inhibitor of NOTUM activity based at least in part on the result of step (i).

17. The method of claim 1, further comprising: (d) providing a second composition substantially similar to the first composition but lacking active NOTUM polypeptide; and determining whether the test compound affects the amount of detectable moiety of the second composition released from the membrane, wherein if the test compound affects the amount of detectable moiety released in the composition comprising active NOTUM polypeptide but has little or no effect on the amount of detectable moiety released in the second composition, then the test compound is confirmed as a modulator of NOTUM activity, and if the test compound affects the amount of detectable moiety released in both compositions to approximately the same extent, the test compound is not confirmed as a modulator of NOTUM activity.

18. The method of claim 1, wherein the membrane is in contact with a liquid medium and steps (c) comprises detecting the detectable moiety in the medium.

* * * * *